US010695410B2

(12) United States Patent
Seavey et al.

(10) Patent No.: US 10,695,410 B2
(45) Date of Patent: Jun. 30, 2020

(54) COMPOSITIONS COMPRISING ANGIOGENIC FACTORS AND METHODS OF USE THEREOF

(71) Applicant: THE TRUSTEES OF THE UNIVERSITY OF PENNSYLVANIA, Philadelphia, PA (US)

(72) Inventors: Matthew Seavey, Secane, PA (US); Yvonne Paterson, Philadelphia, PA (US); Paulo Maciag, Long Grove, IL (US); Duane Sewell, Cheltenham, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/990,790

(22) Filed: May 28, 2018

(65) Prior Publication Data

US 2019/0117750 A1 Apr. 25, 2019

Related U.S. Application Data

(60) Division of application No. 15/225,205, filed on Aug. 1, 2016, now Pat. No. 9,981,024, which is a continuation of application No. 14/304,689, filed on Jun. 13, 2014, now Pat. No. 9,408,898, which is a division of application No. 13/254,607, filed as application No. PCT/US2010/026257 on Mar. 4, 2010, now Pat. No. 8,778,329.

(60) Provisional application No. 61/157,367, filed on Mar. 4, 2009.

(51) Int. Cl.
*A61K 39/02* (2006.01)
*A61K 39/00* (2006.01)
*C07K 14/47* (2006.01)
*C07K 14/71* (2006.01)
*A61K 45/06* (2006.01)
*C07K 14/195* (2006.01)
*C12N 15/74* (2006.01)

(52) U.S. Cl.
CPC .......... *A61K 39/0011* (2013.01); *A61K 45/06* (2013.01); *C07K 14/195* (2013.01); *C07K 14/4748* (2013.01); *C07K 14/71* (2013.01); *C12N 15/74* (2013.01); *A61K 2039/522* (2013.01); *A61K 2039/523* (2013.01); *A61K 2039/53* (2013.01); *A61K 2039/57* (2013.01); *A61K 2039/585* (2013.01); *A61K 2039/6037* (2013.01); *A61K 2039/6068* (2013.01); *C07K 2319/55* (2013.01)

(58) Field of Classification Search
CPC ................................................ A61K 39/0011
See application file for complete search history.

(56) References Cited

U.S. PATENT DOCUMENTS

| | | |
|---|---|---|
| 4,458,066 A | 7/1984 | Caruthers et al. |
| 4,521,382 A | 6/1985 | Kessick et al. |
| 4,567,041 A | 1/1986 | Likhite |
| 4,683,195 A | 7/1987 | Arnheim et al. |
| 4,777,239 A | 10/1988 | Schoolnik et al. |
| 4,816,253 A | 3/1989 | Likhite et al. |
| 4,879,213 A | 11/1989 | Fox et al. |
| 4,945,050 A | 7/1990 | Sanford et al. |
| 8,038,356 B2 | 3/1993 | Paterson et al. |
| 5,262,177 A | 11/1993 | Brown et al. |
| 8,192,857 B2 | 2/1994 | Paterson et al. |
| 5,342,774 A | 8/1994 | Boon et al. |
| 5,369,008 A | 11/1994 | Arlinghause et al. |
| 5,681,570 A | 10/1997 | Yang et al. |
| 5,824,538 A | 10/1998 | Branstrom et al. |
| 5,830,702 A | 11/1998 | Portnoy et al. |
| 5,858,682 A | 1/1999 | Gruenwald et al. |
| 5,876,735 A | 3/1999 | Reed |
| 5,877,159 A | 3/1999 | Powell et al. |
| 6,015,567 A | 1/2000 | Hudziak et al. |
| 6,051,237 A | 4/2000 | Paterson |
| 6,267,690 B1 | 7/2001 | Salmon |
| 6,306,404 B1 | 10/2001 | LaPosta et al. |
| 6,333,169 B1 | 12/2001 | Hudziak et al. |
| 6,479,258 B1 | 11/2002 | Short |
| 6,521,449 B1 | 2/2003 | Polack et al. |
| 6,565,852 B1 | 5/2003 | Paterson |
| 6,767,542 B2 | 7/2004 | Paterson et al. |
| 6,773,900 B2 | 8/2004 | Short et al. |
| 6,855,320 B2 | 2/2005 | Paterson |
| 7,094,410 B2 | 8/2006 | Reisfield et al. |
| 7,135,188 B2 | 11/2006 | Paterson |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,700,344 B2 | 4/2010 | Paterson et al. |
| 8,241,636 B2 | 8/2012 | Paterson et al. |
| 8,268,326 B2 | 9/2012 | Paterson et al. |
| 8,337,861 B2 | 12/2012 | Paterson et al. |

(Continued)

FOREIGN PATENT DOCUMENTS

| | | |
|---|---|---|
| CA | 2 109 176 | 4/1995 |
| EP | 0 902 086 | 3/1999 |

(Continued)

OTHER PUBLICATIONS

Maciag et al (Cancer Research vol. 68, No. 19, pp. 8066-8075) (Year: 2008).*

(Continued)

*Primary Examiner* — Albert M Navarro
(74) *Attorney, Agent, or Firm* — Mark S. Cohen; Pearl Cohen Zedek Latzer Baratz LLP

(57) ABSTRACT

The present invention provides recombinant *Listeria* strains comprising an angiogenic factor, recombinant polypeptides comprising an angiogenic factor operatively linked to a polypeptide comprising a PEST-like sequence, recombinant nucleotide molecules encoding same, related vaccines, and immunogenic and therapeutic methods utilizing same.

20 Claims, 31 Drawing Sheets

Specification includes a Sequence Listing.

(56) References Cited

U.S. PATENT DOCUMENTS

| | | |
|---|---|---|
| 2003/0028206 A1 | 2/2003 | Shiber |
| 2003/0202985 A1 | 10/2003 | Paterson |
| 2004/0033493 A1 | 2/2004 | Tchernev et al. |
| 2004/0228877 A1 | 11/2004 | Dubensky et al. |
| 2005/0118184 A1 | 6/2005 | Paterson et al. |
| 2005/0129715 A1 | 6/2005 | Paterson et al. |
| 2005/0175624 A1 | 8/2005 | Romero et al. |
| 2005/0281783 A1 | 10/2005 | Kinch et al. |
| 2006/0051380 A1 | 3/2006 | Schulick et al. |
| 2006/0093582 A1 | 5/2006 | Paterson et al. |
| 2006/0121053 A1 | 6/2006 | Sweeney et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2006/0269561 A1 | 11/2006 | Paterson et al. |
| 2007/0154953 A1 | 7/2007 | Brunner et al. |
| 2007/0207171 A1 | 9/2007 | Dubensky et al. |
| 2007/0253976 A1 | 11/2007 | Paterson et al. |
| 2007/0264279 A1 | 11/2007 | Gravekamp et al. |
| 2008/0050390 A1 | 2/2008 | Shoenfeld et al. |
| 2008/0124354 A1 | 5/2008 | Paterson et al. |
| 2008/0131456 A1 | 6/2008 | Paterson |
| 2009/0081248 A1 | 3/2009 | Paterson et al. |
| 2009/0081250 A1 | 3/2009 | Paterson et al. |
| 2009/0202587 A1 | 8/2009 | Paterson et al. |
| 2011/0129499 A1 | 6/2011 | Maciag et al. |
| 2011/0223187 A1 | 9/2011 | Shahabi et al. |

FOREIGN PATENT DOCUMENTS

| | | |
|---|---|---|
| EP | 1408048 | 4/2004 |
| JP | 63-173594 A | 7/1988 |
| JP | 01-178592 | 7/1989 |
| WO | WO 1992/09300 | 6/1992 |
| WO | WO 1992/020356 | 11/1992 |
| WO | WO 1993/015212 | 8/1993 |
| WO | WO 1994/017192 A2 | 8/1994 |
| WO | WO 1996/14087 | 5/1996 |
| WO | WO 1996/034631 A1 | 11/1996 |
| WO | WO 1997/013855 A1 | 4/1997 |
| WO | WO 1998/048026 A1 | 10/1998 |
| WO | WO 1999/006544 A1 | 2/1999 |
| WO | WO 1999/007861 A1 | 2/1999 |
| WO | WO 1999/010496 A1 | 3/1999 |
| WO | WO 2001/027295 A1 | 4/2001 |
| WO | WO 2001/072329 A1 | 10/2001 |
| WO | WO 2003/073995 | 9/2003 |
| WO | WO 2003/092600 A2 | 11/2003 |
| WO | WO 2004/006837 A2 | 1/2004 |
| WO | WO 2004/062597 A2 | 7/2004 |
| WO | WO 2003/073826 | 4/2005 |
| WO | WO 2005/037233 | 4/2005 |
| WO | WO 2006/017856 | 2/2006 |
| WO | WO 2006/045750 | 5/2006 |
| WO | WO 2006/036550 | 6/2006 |
| WO | WO 2007/004060 | 1/2007 |
| WO | WO 2007/061848 A2 | 5/2007 |
| WO | WO 2007/106476 | 9/2007 |
| WO | WO 2007/130455 | 11/2007 |
| WO | WO 2008/079172 | 7/2008 |
| WO | WO 2008/109155 | 9/2008 |
| WO | WO 2008/140812 | 11/2008 |
| WO | WO 2010/008782 | 1/2010 |
| WO | WO 2010/027827 | 3/2010 |
| WO | WO 2010/040135 | 4/2010 |
| WO | WO 2010/102140 | 9/2010 |

OTHER PUBLICATIONS

U.S. Pat. No. 8,038,356 dated Mar. 26, 1993, Paterson et al.
U.S. Pat. No. 8,192,857 dated Feb. 7, 1994, Paterson et al.
Adams et al. (1992) "Cre-lox recombination in *Escherichia coli* cells Mechanistic diffrences from the in vitro reaction" J. Mol. Biol. 226:661-673.
Adelman et al. "In vitro deletional mutagenesis for bacterial production of the 20,000-dalton form of human pituitary growth hormone" DNA.; 2(3):183-93. (1983).
Aggarwal et al., "Oral *Salmonella*: Malaria Circumsporozoite Recombinants Induce Specific CD8+ Cytotoxic T Cells", J. Exp. Med. 1990, 172, 1083-1090.
Allison et al. (1997) "Cloning and characterization of a *Prevotella melaninogenica* hemolysin" Infect. Immun. 65(7):2765-71.
Amici et al., "DNA vaccination with full-length or truncated Neu induces protective immunity against the development of spontaneous mammary tumors in HER-2/neu transgenic mice", Gene Therapy (2000) 7, 703-706.
An et al (1996) "A recombinant minigene vaccine containing a nonameric cytoxic-T Lymphocyte epitope confers limited protection against *Listeria monocytogenes* infection." Infect. Immun, vol. 64, No. 5, pp. 1685-1693.
Anderson (1998) "Human gene therapy" Nature, Apr. 30, 392 (6679 Suppl.): 25-30.
Angelakopoulos et al. (2002) "Safetly and shedding of an attenuated strain of *Listeria monocytogenes* with a deletion of actA/plcB in adult volunteers: a dose escalation study of oral inoculation" Infect. Immun. 70(7):3592-601.
Angelov et al., "Therapeutic vaccine for acute and chronic motor neuron disease: implaction for amyotrophic lateral sclerosis" PNAS Apr. 15, 2003, vol. 100, No. 8, 4790-4795.
Ashkenazi et al. "Immunoadhesins" Int Rev Immunol.; 10(2-3):219-27. (1993).
Attwood, et al (2000) "The Babel of Bioinformatics" Science, vol. 290, No. 5491, 471-473.
Awwad (1989) "Cyclophosphamide-induced immunologically meditated regression of a cyclophosphamide-resistant murine tumor: a consequence of eliminating precursor L3T4+ suppressor T-cells" Cancer Res. 49(7):1649-1654.
Baloglu et al., "Immune responses of mice to vaccinia virus recombinants expressing either *Listeria monocytogenes* partial listeriolysin or *Brucella abortus* ribosomal L7/L12 protein" Vet Microbiol 2005, 109(1-2):11-7.
Bargmann CI et al., "The neu oncogene encodes an epidermal growth factor related protein", Nature 319: 226, 1986.
Barry et al. (1992) "Pathogenicity and immunogenicity of *Listeria monocytogenes* small-plaque mutants defective for intracellular growth and cell-to-cell spread" Infection and Immunity 60 (4): 1625-32.
Bast et al. (1975) "Antitumor activity of bacterial infection II effect of *Listeria monocytogenes* on growth of a guinea pig hepatoma" J. Natl. Cancer Inst., 54(3):757-761.
Bear (1986) "Tumor-specific suppressor T-cells which inhibit the in vitro generation of cytolytic T-cells from immune and early tumor-bearing host spleens" Cancer Res. Apr.; 46(4 Pt 1):1805-12.
Beatty, "A dual role for IFN-gamma in resolving the balance between tumor progression and regression" Dissertation Abstracts International, 2000, 61/10B: 5224 Abstract Only.
Beatty et al. "IFN-gamma-dependent inhibition of tumor angiogenesis by tumor-infiltrating CD4+ T cells requires tumor responsiveness to IFN-gamma" J Immunol. 15;166(4):2276-82. Feb. 2001.
Beaucage et al., "deoxynucleoside phosphoramidites-a new class of key intermediates for deoxypolynucleotide synthesis" 1981, Tetra. Lett., 22:1859-1862.
Becker et al., "Gene therapy of prostate cancer with the soluble vascular endothelial growth factor receptor Flkl", Cancer Biology and Therapy, 2002, vol. 1, issue 5, pp. 548-553.
Berche et al., "Intracellular Growth of *Listeria monocytogenes* as a Prerequisite for in vivo Induction of T Cell-Mediated Immunity", J. Immunol. 1987, 138, 2266-2271.
Bergmann CI et al., "The neu oncogene encodes an epidermal growth factor receptor-related protein", Nature 319: 226, 1986.
Bernhard et al. (2002) "Vaccination against the HER-2/neu oncogenic protein" Endocrine-Related Cancer, 9:33-44.
Bielecki et al (1990) "*Bacillus subtilis* expressing a haemolysin gene from *Listeria monocytogenes* can grow in mammalian cells" Nature, vol. 354, pp. 175-176.

(56) References Cited

OTHER PUBLICATIONS

Billington et al. (1997) "The *Arcanobacterium* (*Actinomyces*) pyogenes hemolysin, pyolysin, is a novel member of the thiol-activated cytolysin family" J Bacteriol. Oct.; 179(19): 6100-6.
Bodmer et al. (1988) "Enhanced recognition of a modified peptide antigen by cytotoxic T cells specific for influenza nucleoprotein" Cell 52:253-258.
Boon, et al (2006) "Human T cell responses against melanoma." Annu Rev Immunol. 2006; 24:175-208.
Boon et al., "Tumor Antigens Recognized by T Lymphocytes", Annu. Rev. Immunol. 1994, 12, 337-365.
Botstein et al. "Strategies and applications of in vitro mutagenesis" Science.; 229(4719):1193-201. Sep. 20, 1985.
Bourquin, et al (2000) "Myelin oligodendrocyte glycoprotein-DNA vaccination induces antibody-mediated autoaggression in experimental autoimmune encephalomyelitis." Eur J Immunol 30: 3663-3671.
Bouwer H. et al., "Listeriolysin O is a target of the immune response to *listeria monocytogenes*", J. of Experimental Medicine 1992, 175, 1467-1471.
Bowie et al. "Deciphering the Message in Protein Sequences: Tolerance to Amino Acid Substitutions" Science 247:1306-1310, 1990.
Boyer et al. (2005) "DNA prime *Listeria* boost induces a cellular immune response to SIV antigens in the rhesus macaque model that is capable of limited suppression of SIV239 viral replication" Virology, Mar. 1; 333(1):88-101.
Brake et al. "Alpha-factor-directed synthesis and secretion of mature foreign proteins in Saccharomyces cerevisiae" Proc Natl Acad Sci U S A. 81(15): 4642-4646. Aug. 1984.
Brasseur et al. (1992) "Human gene MAGE-1, which codes for a tumor-rejection antigen, is expressed by some breast tumors" Int. J. Cancer 52(5):839-841.
Brett et al, "Comparison of Antigen Presentation of Influenza A Nucleoprotein Expressed in Attenuated AroA- *Salmonella typhimurium* with That of Live Virus" 1993, J. Immunol. 150:2869-2884.
Brockstedt et al., (2004) "*Listeria*-based cancer vaccines that segregate immunogenicity from toxicity" Proc. Natl. Acad. Sci. USA 101(38):13832-7.
Bron et al. (2004) "Identification of *Lactobacillus plantarum* genes that are induced in the gastrointestinal tract of mice" J Bacteriol. Sep.; 186(17):5721-9.
Brown et al. (1988) "Site-specific integration in *Sccharopolyspora erythraea* and multisite integration in Sterptomyces lividans of antinomycete plasmid pSE101" J. Bacteriology 170: 2287-2295.
Brown , T. et al., "An attenuated aroA *salmonella typhimurium* vaccine elicits humoral and cellular immunity to cloned β-galactosidase in mice", J. of Infectious Diseases 1987, 155(1), 86-92.
Brown et al., "Chemical synthesis and cloning of a tyrosine tRNA gene", 1979, Meth. Enzymol. 68:109-151.
Bruhn et al. (2005) "Characterization of anti-self CD8 T-cell responses stimulated by recombinant *Listeria monocytogenes* expressing the melanoma antigen TRP-2" Vaccine Jul. 21; 23(33):4263-72.
Brundage et al. (1993) "Expression and phosphorylation of the *Listeria monocytogenes* ActA protein in mammalian cells" Proc. Natl. Acad. Sci. USA 90:11890-11894.
Bubert et al. (1997) "The *Listeria monocytogenes* iap gene as an indicator gene for the study of PrfA-dependent regulation" Mol. Gen. Genet. Sep.; 256(1):54-62.
Burnham (2003) "Bad bugs: good for cancer therapy?" Drug Discovery Today 8(2):54-55.
Calendar et al., "Comparative genomics of *Listeria Bacteriophages*" Poster presentation at the ISOPOL XIV meetings, p. 45, May 13-16, 2001 Mannheim, FRG.
Camilli et al. (1993) "Daul roles pf plcA in *Listeria monocytogenes* pathogenesis" Mol. Microbiol. 8:143-157.
Camilli et al., "Intracellular Methicillin Selection of *Listeria monocytogenes* Mutants Unable to replicate in a Macrophage Cell Line", PNAS USA 1989, 86, 5522-5526.
Camili et al., "Insertional Mutagenesis of *Listeria monocytogenes* with a Novel Tn917 Derivative That Allows Direct Cloning of DNA Flanking Transposon Insertions", J. of Bacteriology 172:3738-3744 (1990).
Carbone (1989) "Induction of ovalbumin-specific cytotoxic T cells by in vivo peptide immunization" J Exp Med 169:603-612.
Carbone (1990) "Class I-restricted processing and presentation of exogenous cell-associated antigen in vivo" J Exp Med 171:377-387.
Caudy et al. "Fragile X-related protein and VIG associate with the RNA interference machinery" Genes Dev. 16:2491-96, (2002).
Carter et al. "Site Directed Mutagenesis", Nucl. Acids Res. 13:4331, (1986).
Chamberlain et al. (2000) "Innovations and strategies for the development of anticancer vaccines" Expert Opinion on Pharmacotherapy 1(4):603-614.
Charoenvit et al. "Inability of Malaria Vaccine to Induce Antibodies to a Protective Epitope Within Its Sequence", 1991 Sciences 251:668-671.
Cheever et al., "T-Cell Immunity to Oncogenic Proteins Including Mutated RAS and Chimeric BCR-ABL", Ann. N.Y. Acad. Sci. 1993, 690:101-112.
Chen et al., "DNA Vaccines Encoding Full-Length or Truncated Neu Induce Protective Immunity against Neu-expressing Mammary Tumors" Cancer Research 58, 1965-1971, May 1, 1998.
Cheon et al. "High-affinity binding sites for related fibroblast growth factor ligands reside within different receptor immunoglobulin-like domains" Proc Natl Acad Sci U S A. 1;91(3):989-993. Feb. 1994.
Cohen, J. "Cancer Vaccines Get a Shot in the Arm" Science 262:841-843 (1993).
Concetti et al., "Autoantibody to p185erbB2/neu oncorprotein by vaccination with xenogenic DNA", Cancer Immunol. Immunother., Dec. 1996; 43(5):307-15.
Connell et al., "Old microbes with new faces: molecular biology and the design of new vaccines", 1992 Current Opinion Immunol., 4:442-48.
Cossart et al., "Listeriolysin O is Essential for Virulence of *Listeria Monocytogenes*: Direct Evidence Obtained by Gene Complementation", Infection and Immunity 57:3629-3636 (1989).
Courvalin et al. (1995) "Gene transfer from bacteria to mammalian cells" C R Acad Sci III, Dec.; 318(12):1207-12.
Coussens et al. (1985) "Tyrosine Kinase Receptor with Extensive Homology to EGF Receptor Shares Chromosomal Location with neu Oncogene" Science, vol. 230, 1132-1139.
Cox "Malaria vaccines—progress and problems", 1991 TIB TECH 9:389-394.
Cunto-Amesty et al. (2003) "Strategies in cancer vaccines development" Int J Parasitol, 33(5-6):597-613.
Dakappagari et al. (2000) "Prevention of mammary tumors with a chimeric HER-2 B-cell epitope peptide vaccine" Cancer Res. Jul. 15; 60(14):3782-9.
Darji et al. (2003) "Induction of immune responses by attenuated isogenic mutant strains of *Listeria monocytogenes*" Vaccine 1; 21 Suppl 2:S102-9.
Darji et al. (1995) "Hyperexpression of listeriolysin in the non-pathogenic species *Listeria innocua* and high yield purification" J Biotechnol. Dec. 15; 43(3): 205-12.
Darji et al. (1995) "Listeriolysin generates a route for the presentation of exogenous antigens by major histocompatibility complex class I" Eur J Immunol. Oct.; 25(10):2967-71.
Darji et al. (1997) "TAP-dependent major histocompatibility complex class I presentation of soluble proteins using listeriolysin" Eur J Immunol. Jun; 27(6): 13539.
Darji, et al (1997) "Oral Somatic Transgene Vaccination Using Attenuated S. Typhimuurium." vol. 91, 765-775.
De Boer et al., "A Division Inhibitor and a Topological Specificity Factor Coded for by the Minicell Locus Determine Proper Placement of the Division Septum in *E. coli*" 1989, Cell 56:641-649.
Decatur, et al (2000) "A PEST-like sequence in listeriolysin O essential for *Listeria monocytogenes* pathogenicity." Science, vol. 290, No. 5493, pp. 992-995.

(56) References Cited

OTHER PUBLICATIONS

Delibero et al, "antigen-specific lyt-2+ cytolytic t lymphocytes from mice infected with the intracellular bacterium *listeria monocytogenes*" 1986, J. Immunol. 137(8):2688-2694.
Derbinski J.A., Schulte B. Kyewski and C. Klein, 2001, "Promiscuous gene expression in medullary thymic epithelial cells mirrors the peripheral self", Nat. Immunol. 2:1032.
Dermime et al. (2004) "Vaccine and antibody-directed T cell tumour immunotherapy", Biochim. Biophys. Acta. 1704(1):11-35.
Deshpande et al. (1997) "Isolation of a contact-dependent haemolysin from *Mycobacterium tuberculosis*" J. Med. Microbiol. Mar; 46(3):233-8.
Di Carlo et al., "Inhibition of mammary carcinogenesis by systemic interleukin 12 or p185neu DNA vaccination in HER-2/neu transgenic BALB/c mice" Clin. Cancer Res. Mar. 2001; 7(3 Suppl):830s-837s.
Dietrich et al. (1998) "Delivery of antigen-encoding plasmid DNA into the cytosol of macrophages by attenuated suicide *Listeria monocytogenes*" Nature Biotechnology 15:181-185.
Dietrich et al. (2001) "From evil to good: a cytolysin in vaccine development" Trends Microbiol. Jan.; 9(1):23-8.
Disis et al. (1996) Peptide-Based, but Not Whole Protein, Vaccines Elicit Immunity to HER-2/neu, an Oncogenic Self Protein, The Journal of Immunology, vol. 156, 3151-3158.
Disis et al., "Immunity to the HER-2/neu oncogenic protein", Ciba Found. Symp. 1994 187:198-211.
Disis et al., "Generation of T-Cell Immunity to the HER-2/neu Protein After Active Immunization with HER-2/neu Peptide-Based Vaccines" J Clin Oncol 20:2624-2632, 2002.
Disis et al. "Generation of immunity to the HER-2/neu oncogenic protein in patients with breast and ovarian cancer using a peptide-based vaccine" Clinical Cancer Research, vol. 5, No. 6, pp. 1289-1297 Jun. 1999.
Disis et al., "Humoral epitope-spreading following immunization with a HER-2/neu peptide based vaccine in cancer patients", J. Clin. Immunol., 2004, 24(5): 571-578.
Domenech et al. "Identification of an HLA-A11-restricted epitope from the tandem repeat domain of the epithelial tumor antigen mucin" The Journal of Immunology, Nov. 15, vol. 155 No. 10 4766-4774, (1995).
Dominiecki et al. "Tumor sensitivity to IFN-gamma is required for successful antigen specific immunotherapy of a transplantable mouse tumor model for HPV-transformed tumors" Cancer Immunol Immunother. 54(5):477-88. May 2005.
Dramsi et al. (1995) "Entry of *Listeria monocytogenes* into hepatocytes requires expression of inIB, a surface protein of the internalin multigene family" Mol Microbiol 16(2):251-61.
Dumitrescu et al., "Understanding breast cancer risk- where do we stand in 2005?" J. Cell. Mol. Med. vol. 9, No. 1, 2005, pp. 208-221.
Dunn et al. (1991) "Selective radiation resistance of immunologically induced T cells as the basis for irradiation-induced T-cell-mediated regression of immunogenic tumor" J Leukoc Biol. 49(4):388-396.
Düwel et al. "Reduced tumor growth and angiogenesis in endoglin-haploinsufficient mice" Tumor Biology. 2007:28(1):1-8.
Ebert et al. (1990) "Selective immunosuppressive action of a factor produced by colon cancer cells" Cancer Res. 50(19):6158-6161.
Edelson et al. "Intracellular antibody neutralizes *Listeria* growth." Immunity 14.5 (2001): 503-512.
Eisenlohr et al., "Flanking Sequences Influence the Presentation of an Endogenously Synthesized Peptide to Cytotoxic T Lymphocytes" The Journal of Experimental Medicine 175:481-487 (1992).
Esserman et al., "Vaccination with the extracellular domain of p185neu prevents mammary tumor development in neu transgenic mice", Cancer Immunol. Immunother. Feb. 1999; 47(6):337-42.
European Search Report for European Application No. 10749350.4 dated Nov. 5, 2013.
European Search Report for European Application No. 17159666.1 dated Dec. 14, 2017.
European Search Report for European Application No. 07872167.7 dated Mar. 31, 2011.
European Search Report for European Application No. 15172620.5 dated Oct. 8, 2015.
Evan et al. "Isolation of monoclonal antibodies specific for human c-myc proto-oncogene product" 5(12):3610-6. Dec. 1985.
Ezzel et al., "Cancer "Vaccines": An idea whose time has come?" The Journal of NIH Research, vol. 7, 1995 pp. 46-49.
Falk et al. (1991) "Identification of naturally processed viral nonapeptides allows their quantification in infected cells and suggests an allele-specific T cell epitope forecast" J Exp Med. 174(2):425-434.
Field et al. "Purification of a RAS-responsive adenylyl cyclase complex from *Saccharomyces cerevisiae* by use of an epitope addition method." Molecular and cellular biology 8.5 (1988): 2159-2165.
Finn, et al (2003) "Cancer vaccines: between the idea and the reality." Nature Reviews Immunology, 3: 630-641.
Finn et al., MUC-1 Epithelial Tumor Mucin-Based Immunity and Cancer Vaccines, Immuno. Rev. 1995 145:61-89.
Flamm et al. "Introduction of pAMβ1 into *Listeria Monocytogenes* by Conjugation and Homology Between Native *L. Monocytogenes* Plasmids", Infection and Immunity 44:157-161(1984).
Foy et al., "Vaccination with HER-2/neu DNA or protein subunits protects against growth of a HER-2/neu-expressing murine tumor" Vaccine, Mar. 21, 2001; 19(1719):2598-606.
Frankel et al. (1995) "Induction of cell-mediated immune responses to human immunodeficiency virus type 1 Gag protein by using *Listeria monocytogenes* as a live vaccine vector" J. Immunol. 155:4775-4782.
Frey (1993) "Rat adenocarcinoma 13762 expresses tumor rejection antigens but tumor-bearing animals exhibit tumor-specific immunosuppression" Clin. Immunol. Immunopathol. 69(2):223-233.
Friedman et al. (2000) "Induction of human immunodeficiency virus (HIV)-specific CD8 T-cell responses by *Listeria monocytogenes* and a hyperattenuated *Listeria* strain engineered to express HIV antigens" J. Virology 74 9987-9993.
Fu et al. (1990) "Expansion of Immunoregulatory macrophages by granulocyte-macrophage colony-stimulating factor derived from a murine mammary tumor" Cancer Res. 50(2):227-234.
Fuji (1987) "Significance of suppressor macrophages for immunosurveillance of tumor-bearing mice" J Natl Cancer Inst 78(3):509-517.
Furukawa (1993) "Nude mouse metastatic models of human stomach cancer constructed using orthotopic implantation of histologically intact tissue" Cancer Res. 53(5):1204-1208.
Gaillard et al., "Transposon Mutagenesis as a Tool to Study the Role of Hemolysin in the Virulence of *Liestria Monocytogenes*", Infection and Immunology 52:50-55 (1986).
Gaillard et al, "In Vitro model of Penetration and Intracellular Growth of *Listeria monocytgenes* in the Human Enterocyte-Like Cell Line Caco-2", Infect. Immun. 1987, 55,2822-2829.
Galen et al. (2001) "Can a 'flawless' live vector vaccine strain be engineered?" Trends Microbiol. 9(8):372-6.
Gansbacher et al., "Interleukin 2 Gene Transfer into Tumor Cells Abrogates Tumorigenicity and Induces Protective Immunity" J. Exp. Med. 1990, 172, 1217-1224.
Gao et al, "Recombinant *Salmonella typhimurium* Strains That Invade Nonphagocytic Cells Are Resistant to Recognition by Antigen-Specific Cytotoxic T Lymphocytes" 1992, Inf. & Imm., 60(9):3780-3789.
Garay-Malpartida et al., "CaSPredictor: a new computer-based tool for caspase substrate prediction", Bioinformatics. Jun. 2005;21 Suppl 1:i169-76.
Gentschev et al. (1996) "Development of antigen-delivery systems, based on the *Escherichia coli*hemolysin secreatiohn pathway" Gene 179:133-140.
Gentschev et al (1995) "*Salmonella* Strain Secreting Active Listeriolysin Changes Its Intracellular Localization" Infect. Immun., vol. 63: 4202-4205.
Gillespie et al. "The potential of melanoma antigen expression in cancer therapy", Cancer Treat. Rev. 1999 25(4):219-27.
Gilman et al., "Isolation of sigma-2%specific promoters from *Bacillus subtilis* DNA" 1984, Gene 32:11-20.

(56) References Cited

OTHER PUBLICATIONS

Gilmore et al. (1989) "A *Bacilius cereus* cytolytic determinant, cereolysin AB, which comprieses the phospholipase C and sphingomyelinase genes: nucleotide sequence and genetic linkage" J Bacteriol. Feb; 171(2): 744-53.
Glomski et al. (2002) "The *Listeria monocytogenes* hemolysin has an acidic pH optimum to compartmentalize activity and prevent damage to infected host cells" J Cell Biol. Mar. 18; 156(6):1029-38.
Goebel et al. (1993) "*Listeria monocytogenes*-a model system for studying the pathomechanisms of an intracellular microorganism" Zbl. Bakt. 278:334-347.
Golumbek et al., "Treatment of Established Renal Cancer by Tumor Cells Engineered to Secrete Interleukin-4", Science 1991, 254, 713-716.
Goossens et al. (1992) "Induction of protective CD8+ T lymphocytes by an attenuated *Listeria monocytogenes* actA mutant" Int Immunol. Dec; 4(12):1413-8.
Goossens et al. (1995) "Attenuated *Listeria monocytogenes* as a live vector for induction of CD8+ T cells in vivo: a study with the nucleoprotein of the lymphocytic choriomeningitis virus" Int Immunol. May; 7(5):797-805.
Gregory et al. (1997) "Internalin B promotes the replication of *Listeria monocytogenes* in mouse hepatocytes" Infect. Immun. 65(12):5137-41.
Gunn et al. (2002) "Recombinant Intra-cellular Bacteria as Carries for Tumor Antigens" In Vaccine Delivery Strategies, Chapter 14, Eds. Guido Dietrich and Werner Goebel, Horizon Scientific Press, UK.
Gunn, "Recombinant *Listeria monocytogenes* as a tumor therapeutic" Dissertation Abstracts International, 2001, 62/5B:2244 Abstract Only.
Gunn et al. (2001) "Listeriolysin- a useful cytolysin" Trends Microbiol. 9(4):161-162.
Gunn et al. "Two *Listeria Monocytogenes* Vaccine Vectors That Express Different Molecular Forms of Human Papilloma Virus-16 E7 Induce Qualitatively Different T Cell Immunity That Correlated With Their Ability to Induce Regression of Established Tumors Immortalized by HPV-16", Journal of Immunology, vol. 167, No. 11, 2001, pp. 6471-6479.
Guzman, et al (1998) "Attenuated *Listeria monocytogenes* carrier strains can deliver an HIV-1 gp120 T helper epitope to MHC class II-restricted human CD4+ T cells." European Journal of Immunology 28: 1807-1814.
Harty et al. (1996) "Primary and secondary immune responses to *Listeria monocytogenes*" Curr. Opin. Immunol. 8:526-530.
Hassan et al. (2004) "Mesothelin: a new target for immunotherapy" Clin. Cancer Res. 10 (12 Pt 1):3937-42.
Hatfield et al. "Antiangiogenic therapy in acute myelogenous leukemia: targeting of vascular endothelial growth factor and interleukin 8 as possible antileukemic strategies" Curr Cancer Drug Targets; 5:229-48. (2005).
Hauf et al. (1997) "*Listeria monocytogenes* infection of P388D1 macrophages results in a biphasic NF-kappaB (RelA/p50) activation induced by lipoteichoic acid and bacterial phospholipases and mediated by IkappaBalpha and IkappaBbeta degradation" Proc. Natl. Acad. Sci. USA Aug. 19; 94(17):9394-9.
Haynes, "Scientific and Social Issues of Human Immunodeficiency Virus Vaccine Development" 1993 Science 260:1279-1286.
Heidaran et al. "Beta PDGFR-IgG chimera demonstrates that human beta PDGFR Ig-like domains 1 to 3 are sufficient for high affinity PDGF BB binding" The FASEB Journal vol. 9 No. 1 140-145 Jan. 1995.
Hess et al. (1995) "*Listeria monocytogenes* p60 supports host cell invasion by and in vivo survival of attenuated *Salmonella typhimurium*" Infect. Immun. May; 63(5):2047-53.
Hess et al. (1996) "*Salmonella typhimurium* aroA- infection in gene-targeted immunodeficient mice: major role of CD4+ TCR-alpha beta cells and IFN-gamma in bacterial clearance independent of intracellular location" J Immunol. May 1; 156(9):3321-6.

Hess et al. (1996) "Superior efficacy of secreted over somatic antigen display in recombinant *Salmonella* vaccine induced protection against listeriosis" Proc. Nat. Acad. Sci. 93:1458-1463.
Hess et al. (1997) "Protection against murine listeriosis by an attenuated recombinant *Salmonella typhimurium* vaccine strain that secretes the naturally somatic antigen superoxide dismutase" Infect. Immun. Apr.; 65(4):1286-92.
Hess et al. (1998) "*Mycobacterium bovis bacilli* Calmette-Guerin strains secreting listeriolysin of *Listeria monocytogenes*" Proc. Natl. Acad. Sci. 95:5299-5304.
Higgins et al. (1998) "Bacterial delivery of DNA evolves" Nat. Biotechnol. Feb.; 16(2):138-9.
Hodgson (2000) "Generalized transduction of serotype 1/2 and Serotype 4b strains of *Listeria monocytogenes*" Mol. Microbiol. 35(2):312-23.
Hoffman et al. "Naturally Acquired Antibodies to Sporozoites Do Not Prevent Malaria: Vaccine Development Implications" 1987 Science 237:639-642.
Hoffman et al. "Preerythrocytic malaria vaccine development", 1993 Mol. Immunological Considerations in Mal. Vaccine Dev. Ed. Good & Saul. pp. 149-167.
Hoogenboom and Winter, "By-passing Immunisation Human Antibodies from Synthetic Repertoires of Germline VH Gene Segments Rearranged in Vitro" J. Mol. Biol. 227:381 (1991).
Hopp et al. "A short polypeptide marker sequence useful for recombinant protein identification and purification". Bio/Technology 6, 1204-1210, (1988).
Hu et al. (2004) "*Escherichia coli* expressing recombinant antigen and listeriolysin O stimulate class I-restricted CD8+ T cells following uptake by human APC" J. Immunology 172:1595-1601.
Huang et al. (1994) "Role of bone marrow-derived cells in presenting MHC class I-restricted tumor antigens" Sceince 264 961-965.
Hussain et al. (2004) "CD4+CD25+ regulatory T cells that secrete TGFbeta and IL-10 are preferentially induced by a vaccine vector" J Immunother Sep.-Oct.; 27(5):339-46.
Ikonomidis et al. (1994) Abstract E-90, Abstracts, 94th General Meeting of the American Society for Microbiology, May 23-27.
Ikonomidis, et al (1994) "Delivery of a viral antigen to the class I processing and presentation oathway by *Listeria monocytogenes*." Journal of Experimental Medicine, vol. 180, No. 6, pp. 2209-2218.
Ikonomidis, "Development of *Listeria Monocytogenes* as a vaccine vector for the delivery of a model antigen to the immune system (drug delivery)", 1996 Dissertation Abs. Int'l 57(4B) p. 2462 Abstract only.
International Search Report Application No. PCT/US10/26257 dated Aug. 19, 2010.
International Written Opinion Application No. PCT/US10/26257 dated Sep. 15, 2011.
International Search Report and Written Opinion Application No. PCT/US07/18091 dated Sep. 8, 2008.
International Search Report and Written Opinion Application No. PCT/US09/59582 dated Dec. 15, 2009.
International Search Report of Application No. PCT/US07/10635 dated Sep. 11, 2008.
International Search Report of Application No. PCT/US08/03067 dated Aug. 29, 2008.
International Search Report of Application No. PCT/US07/06292 dated Jun. 17, 2008.
International Search Report of Application No. PCT/US01/09736 dated Jul. 27, 2001.
International Search Report of Application No. PCT/US05/32682 dated Jun. 1, 2006.
International Search Report of Application No. PCT/US95/14741 dated Feb. 15, 1996.
International Search Report of Application No. PCT/US07/18091 dated Sep. 8, 2008.
Jensen (1997) "Recombinant *Listeria monocytogenes* vaccination eliminates papillomavirus-induced tumors and prevents papiloma formation from viral DNA" J Virol. 71(11):8467-8474.
Jensen et al. (1997) "Recombinant *Listeria monocytogenes* as a live vaccine vehicle and a probe for studying cell-mediated immunity" Immunological Review 158:147-157.

(56) References Cited

OTHER PUBLICATIONS

Jiang et al., Characterization of a mutant *Listeria monocytogenes* strain expressing green fluorescent protein, Acta Bio Chim Biophys Sin (Shanghai) 2005, 37(1), 19-24.

Jiang C et al., Mutations that decrease DNA binding of the processivity factor of the herpes simplex virus DNA polymerase reduce viral yield, alter the kinetics of viral DNA replication and decrease the fidelity of DNA replication, J. Virol. Apr. 2007, 81(7):3495-502.

Jiao et al. A plasmid DNA vaccine encoding the extracellular domain of porcine endoglin induces anti-tumour immune response against self-endoglin-related.

Jones et al. (1994) "Charcterization of *Listeria monocytogenes* pathogeneis in a strain expressing perfringolysin O in place of listeriolysin O" Infect. Immun. 62:56085613.

Kaufman, et al. (1999) "Impact of intracellular location of and antigen display by intracellular bacteria: implications for vaccine development", J Immunol. Lett, 65 (12):81-84.

Kawashima et al., "The Multi-epitope Approach for Immunotherapy for Cancer: Identification of Several CTL Epitopes from Various Tumor-Associated Antigens Expressed on Solid Epithelial Tumors", Hum. Immunol. 1998 59:1-14.

Kerksiek (1999) "T cell responses to bacterial infection." Curr Opin. Immunol., vol. 1, No. 4, pp. 400-405.

King CR et al., "Amplification of a novel v-erbB-related gene in a human mammary carcinoma", Science 229:974, 1985.

Knutson, K. L. et al., "Immunization with a HER-2/neu helper peptide vaccine generates HER-2/neu CD8 T-cell immunity in cancer patients" The Journal of Clinical Investigation, 107:477-484, 2001.

Kocks et al. (1992) "*L. monocytogenes*-induced actin assembly requires the actA gene product." Cell, vol. 68, No. 3, pp. 521-531.

Kovacsovics-Bankowski et al. (1993) "Efficient major histocompatibility complex class I presentation of exogenous antigen upon phagocytosis by macrophages" Proc. Natl. Acad. Sci. USA 90:4942-4946.

Krieg AM et al., 1995, "CpG motifs in bacterial DNA trigger direct B-cell activation", Nature 374:546.

Kruisbeek, A. "In Vivo Depletion of CD4- and CD8-specific T cells" Current Protocols in Immunology, John Wiley & Sons, Inc., eds., 1994, V. 1, 4.1.1-4.1.2.

Kumar et al. "Amino acid variations at a single residue in an autoimmune peptide profoundly affect its properties: T-cell activation, major histocompatability complex binding, and ability to block experimental allergic encephalomyelitis", PNAS 87:1337-1341, 1990.

Kunkel et al. "Rapid and Efficient Site-Specific Mutagenesis Without Phenotypic Selection" Methods Enzymol.; 154:367-82 (1987).

Kyte et al. "A Simple Method for Displaying the Hydropathic Character of a Protein" J. Mol. Biol. 157, 105-132, (1982).

Lacey et al., "Phase IIa Safety and Immunogenicity of a Therapeutic Vaccine, TA-GW, in Persons with Genital Warts", The Journal of Infectious Diseases 1999; 179:612-618.

Lambiase et al., Topical Ereatmert with nerve growth factor in the animal model of herpetic keratitis Graefes Arch Clin. Exp. Ophthalmol. May 4, 2007.

Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site" J. Virology 75(20):9654-9664.

Lampson et al. (1993) "Exploiting the IacZ reporter gene for quantitative analysis of disseminated tumor growth within the brain: use of the IacZ gene product as a tumor antigen, for evaluation of antigen modulation, and to facilitate image analysis of tumor growth in situ" Cancer Research 53:176-182.

Lara-Tejero et al. (2004) "T cell responses to *Listeria monocytogenes*" Curr. Opin. Microbiol. 7(1):45-50.

Larochelle et al. "Specific receptor detection by a functional keratinocyte growth factor-immunoglobulin chimera." The Journal of cell biology 129.2 (1995): 357-366.

Lasa, et al (1997) "Identification of two regions in the N-terminal domain of ActA involved in the actin comet tail formation by *Listeria monocytogenes*." EMBO 16(7): 1531-40.

Lauer et al., "Systematic mutational analysis of the amino-terminal domain of the *Listeria monocytogenes* ActA protein reveals novel functions in actin-based motility" Molecular Microbiology 42(5): 1163-1177, 2001.

Lauer et al. (2002) "Construction, characterization, and use of two *Listeria monocytogenes* site-specific phage integration vectors" J. Bacteriology 184:41774186.

Lauer et al. "Characterization of the Attachment Site of Bacteriophage U153 within the *Listeria monocytogenes* comK Gene" ASM Meeting, Abstract 1999.

Leao et al. (1995) "A species-specific nucleotide sequence of Mycobacterium tuberculosis encodes a protein that exhibits hemolytic activity when expressed in *Escherichia coli*" Infect. Immun. Nov.; 63(11):4301-6.

Lebrun, et al (1996) "Internalin must be on the bacterial surface to mediate entry of *Listeria monocytogenes* into epithelial cells." Molecular Microbiology 21(3): 579592.

Lee et al. (1991) "Construction of single-copy integration vectors for *Staphylococcus aureus*" Gene 103:101-5.

Lee et al., "Endoglin (CD105) is a target for an oral DNA vaccine against breast cancer", Cancer Immunol. Immunother. 2006, vol. 55, pp. 1565-1574.

Lehner et al. (1996) "Processing and delivery of peptides presented by MHC class I molecules" Curr. Opin. Immunol. 8(1):59-67.

Lejeune (1994) "Nitric oxide involvement in tumor-induced immunosuppression" J Immunol. 152(10):5077-5083.

Liau et al. (2002) "Tumor immunity within the central nervous system stimulated by recombinant *Listeria monocytogenes* vaccination" Cancer Res. 62(8):2287-93.

Lin et al. (1996) Treatment of establishment tumors with a novel vaccine that enhances Major Histocompatibility Class II presentation of tumor antigen Cancer Res. 56: 21-26.

Lin et al. (2002) "Oral vaccination with recombinant *Listeria monocytogenes* expressing human papillomavirus type 16 E7 can cause tumor growth in mice to regress" Int. J. Cancer Dec. 20; 102(6):629-37.

Lin, et al (1996) "Treatment of Established Tumors with a Novel Vaccine That Enhances Major Histocompatibility Class II Presentation of Tumor Antigen" Cancer Res. 1996 56:21-56: 21-26.

Lingnau et al. (1995) "Expression of the *Literia monocytogenes* EGD inlA and inlB genes, whose products mediate bacterial entry into tissue culture cell lines, by PrfA-dependent and independent mechanisms" Infect. Immun. Oct.; 63(10):3896-903.

Loeffler et al. (2006) "Comparison of different live vaccine strategies in vivo for delivery of protein antigen or antigen-encoding DNA and mRNA by virulence-attenuated *Listeria monocytogenes*" Infect. Immun. Jul.; 74(7):3946-57.

Loessner et al. (1995) "Heterogeneous endolysins in *Listeria monocytogenes* bacteriophages: a new class of enzymes and evidence for conserved holin genes within the siphoviral lysis cassettes" Mol. Microbiol. Jun.; 16(6):1231-41.

Loessner et al. (2000) "Complete nucleotide sequence, molecular analysis and genome structure of bacteriophage A118 of *Listeria monocytogenes*: implications for phage evolution" Molecular Microbiology 35(2):324-40.

Lutz-Freyermuth et al. "Quantitative determination that one of two potential RNA-binding domains of the a protein component of the U1 small nuclear ribonucleoprotein complex binds with high affinity to stem-loop II of U1 RNA." *Proceedings of the National Academy of Sciences* 87.16 (1990): 6393-6397.

Maciag et al. "Cancer Immunotherapy Targeting the High Molecular Weight Melanoma-Associated Antigen Protein Results in a Broad Antitumor Response and Reduction of Pericytes in the Tumor Vasculature" Cancer Res. 68(19):8066-75. 2. Oct. 1, 2008.

Maciag et al., "A *listeria monocytogenes*-based vaccine against HMW-MAA can impair growth of HMW-MAA expressing and non-expressing tumors in mice", AACR Meeting Abstract, Apr. 2007: 1881.

Makela, et al. (1987) Hand Book of Experimental Immunology, vol. 1, chapter 3, pp. 3.1-3.13.

(56) References Cited

OTHER PUBLICATIONS

Mandal et al. (2002) "*Listeriolysin* O-liposome-mediated cytosolic delivery of macromolecule antigen in vivo: enhancement of antigen-specific cytotoxic T lymphocyte frequency, activity, and tumor protection" BBA 1563 7-17.
Manjili et al. (2003) "HSP110-HER2/neu chaperone complex vaccine induces protective immunity against spontaneous mammary tumors in HER-2/neu transgenic mice" J. Immunol. Oct. 15; 171(8):4054-61.
Marks et al., "By-passing Immunization Human Antibodies from V-gene Libraries Displayed on Phage" J. Mol. Biol. 222:581 (1991).
Marquis et al. (1997) "Proteolytic pathways of activation and degradation of a bacterial phospholipase C during intracellular infection by *Listeria monocytogenes*" J. Cell Biol. 137:1381-1392.
Martin et al. "GAP domains responsible for ras p21-dependent inhibition of muscarinic atrial K+ channel currents. Science"; 255(5041):192-194. Jan. 10, 1992.
Martin et al. (1986) "Nucleotide sequence of the tetM tetracycline resistance determinant of the sterptococcal conjugative shuttle transposon Tn1545" Nucleic Acid Res. 14:7047-7058.
Marx et al. (2002) "Broad-host-range cre-lox system for antibiotic marker recycling in gram-negative bacteria" Biotechniques Nov.; 33(5):1062-7.
Mata, M, Yao, Z, Zubair, A, Syres, K and Y Paterson, Evaluation of a recombinant *Listeria monocytogenes* expressing an HIV protein that protects mice against viral challenge. Vaccine 19:1435-45, 2001.
Mccarty et al., "Targeting p53 for Adoptive T-Cell Immunotherapy", Cancer Research 1998 15:58 2601-5.
Mckaig et al., "Human Papillomavirus and Head and Neck Cancer: Epidemiology and Molecular Biology" Head Neck 1998 20 (3):250-65.
Mclaughlan et al. (1998) "Molecular characterization of an autolytic amidase of *Listeria monocytogenes* EGD" Microbiology May; 144(Pt 5):1359-67.
Mengaud, et al (1988) "Expression in *Escherichia Coli* and Sequence Analysis of the Listeriolysin O Determinant of *Listeria Monocytogens*." Infection and Immunity, vol. 56, No. 4, 766-772.
Merrifield et al., "Solid Phase Peptide Synthesis. I. The Synthesis of a Tetrapeptide" J. Am. Chem. Soc., 85:2149-2156 (1963).
Mikayama, et al. (1993) "Molecular cloning and functional expression of a CDNA encoding gycosylation-inhibiting factor" Proc. Natl. Acad. Sci. USA 90:10056-10060.
Miller et al., "Xenograft Model of Progressive Human Proliferative Breast Disease" 1995, Faseb J., 9:190-199.
Mizukami et al. "Induction of interleukin-8 preserves the angiogenic response in HIF-1 deficient colon cancer cells" Nature Medicine, 11:992-97. (2005).
Mlynarova et al. (2002) "The promiscuity of heterospecific lox sites increases dramatically in the presence of palindromic DNA" Gene Aug. 21; 296(1-2):129-37.
Mollet et al. (1993) "Directed genomic integration, gene replacement, and integrative gene expression in *Streptococcus thermophilus*" J. Bacteriology 175:4315-4324.
Moore et al., "Introduction of Soluble Protein into the Class I Pathway of Antigen Processing and Presentation", Cell 1988, 54, 777-785.
Moriishi et al., "Sequence analysis of the actA gene of *Listeria monocytogenes* isolated from human." Microbiol. Immunol., vol. 42, No. 2, ages 129-132 (1998).
Muller W. J. (1991) Expression of activated oncogenes in the murine mammary gland: transgenic models for human breast cancer, Canc. Metastasis Rev. 10:217-27.
Narang et al., "Improved phosphotriester method for the synthesis of gene fragments", 1979, Meth. Enzymol. 68:90-99.
Naz et al. "Novel Human Prostate-Specific Cdna: Molecular Cloning, Expression, and Immunobiology of the Recombinant Protein" Biochembiophys Res Commun.; 297(5):1075-84. Oct. 11, 2002.
Neilsen PE, "Peptide nucleic acids as therapeutic agents", Curr Opin Struct Biol 9:353-57 (1999).

Neve et al. "A collection of breast cancer cell lines for the study of functionally distinct cancer subtypes" Cancer cell. Dec. 31, 2006;10(6):515-27.
Ngo, et al. (1994) The Protein Folding Problem and Tertiary Structure Prediction 492-495.
Ochsenbein et al. (1999) "A comparison of T cell memory against the same antigen induced by virus versus intracellular bacteria" Proc. Natl. Acad. Sci. USA Aug. 3; 96(16): 9293-8.
Ogasawara et al. "A strategy for making synthetic peptide vaccines" Proc Natl Acad Sci U S A. 89(19):8995-9. Oct. 1, 1992.
Oscarsson et al. (1996) "Induction of haemolytic activity in *Escherichia coli* by the slyA gene product" Mol. Microbiol. Apr. 20(1):191-9.
Paborsky et al. "Mammalian cell transient expression of tissue factor for the production of antigen" Protein Eng. May 1990; 3(6):547-53.
Pagano, J.S., "Epstein-Barr Virus: The First Human Tumor Virus and its Role in Cancer", Proc. Assoc. Am. Physicians 1999 111(6):573-80.
Paglia, et al (1997) "The defined attenuated *Listeria monocytogenes* delta mp12 mutant is an effective oral vaccine carrier to trigger a long-lasting immune response against a mouse fibrosarcoma."Eur J Immunol 27: 1570-1575.
Palmeros et al. (2000) "A family of removable cassettes designed to obtain antibiotic-resistance-free genomic modifications of *Escherichia coli* and other bacteria" Gene. Apr. 18; 247(1-2):255-64.
Pan (1999) "Regression of established B16F10 melanoma with a recombinant *Listeria monocytogenes* vaccine" Cancer Res. 59(20):5264-5269.
Pan et al. (1995) "A recombinant *Listeria monocytogenes* vaccine expressing a model tumor antigen protects mice against lethal tumor cell challenge and causes regression of established tumours" Nature Med. 1:471-477.
Pan, et al (1995) "Regression of established tumors in mice mediated by the oral administration of a recombinant *Listeria monocytogenes* vaccine."Cancer Research 55: 4776-4779.
Parida et al. (1998) "Internalin B is essntial for adhesion and mediates the invasion of *Listeria monocytogenes* into human endothelial cells" Mol. Microbiol. Apr; 28(1):81-93.
Paterson, "Rational approaches to immune regulation", Immunologic Research, 2003; 27/2-3:451-462.
Paterson et al. "Recombinant *Listeria Monocytogenes* cancer vaccines", Current Opinion in Immunology, 1996, 8:664-669.
Paterson et al, Proceedings of the American Association for Cancer Research, Mar. 2000, 41:890, abstract #S25.
Paul, et al (1989) Fundamental Immunology, 987-988.
Peng et al. (2004) "The ability of two *Listeria monocytogenes* vaccines targeting human papillomavirus-16 E7 to induce an anti-tumor response correlates with myeloid dendritic cell function" J. Immunol. 172:6030-6038.
Penichet et al. (2001) "Antibody-cytokine fusion proteins for the therapy of cancer" J. Immunological Methods 248:91-101.
Peters et al. (2003) "Tailoring host immune responses to *Listeria* by manipulation of virulence genes- the interface between innate and acquired immunity" FEMS Immunol Med Microbiol. Apr. 1; 35(3):243-53.
Pfeifer et al. (1993) "Phagocytic processing of bacterial antigens for class I MHC presentation to T cells" Nature Jan. 28; 361(6410):359-62.
Piechocki et al., "Complementary Antitumor Immunity Induced by Plasmid DNA Encoding secreted and Cytoplasmic Human ErbB-2" The Journal of Immunology, 2001, 167:3367-3374.
Pilon et al., "Vaccination with Cytoplasmic ErbB-2 DNA Protects Mice from Mammary Tumor Growth without Anti-ErbB-2 Antibody", The Journal of Immunology, 2001, 167:3201-3206.
Portnoy et al., "Role of Hemolysin for the Intracellular Growth of *Listeria monocytogenes*", J. Exp. Med. 1988, 176, 1459-1471.
Portnoy et al., "γ Interferon Limits Access of *Listeria Monocytogenes* to the Macrophage Cytoplasm", J. Exp. Med. 1989, 170, 2141-2146.
Powell et al., "Epitope spreading: protection from pathogens, but propagation of autoimmunity?", Clin. Exp. Dermatol., 2001, 26(5): 427-433, p. 431.

(56) References Cited

OTHER PUBLICATIONS

Punwaney et al., "Human Papillomavirus May be Common within Nasopharyngeal Carcinoma of Caucasian Americans: investigations of Epstein-Barr virus and human papilloma-virus in Eastern and Western Nasopharyngeal Carcinoma using Ligation-Dependent polymerase chain reaction", Head Neck 1999 21(1) :21-9.
Pupa et al. (2001) "Prevention of spontaneous neu-expressing mammary tumor development in mice transgenic for rat proto-neu by DNA vaccination" Gene Ther. Jan. 8(1):75-9.
Quenee et al. (2005) "Combined sacB-based negative selection and cre-lox antibiotic marker recycling for efficent gene deletion in *pseudomonas aeruginosa*" Biotechniques Jan. 38(1):63-7.
Radford et al. (2002) "A recombinant *E. coli* vaccine to promote MHC class I-dependent antigen presentation: application to cancer immunotherapy" Gene Therapy 9:1455-1463.
Radford et al. (2003) "Recombinant *E. coli* efficiently delivers antigen and maturation signals to human dendritic cells: presentation of MART1 to CD8+ T cells" Int. J. Cancer 105:811-819.
Ramaswamy M et al., Interactions and management issues in HSV and HIV coinfection Expert Rev Anti Infect Ther. Apr. 2007, 5(2):231-43.
Rammensee et al., "Protein-specific cytotoxic T lymphocytes, Recognition of transfectants expressing intracellular, membrane-associated for secreted forms of β-galactosidaes", 1989, Immunogenetics, 30:296.
Ratner et al., "Complete Nucleotide Sequence of the AIDS virus, HTLV-III", Nature 1985, 313(1), 277-284.
Raveneau et al. (1992) "Reduced virulence of a *Listeria monocytogenes* phospholipase-deficient mutant obtained by transposon insertion into the zinc metalloprotease gene" Infect. Immun. 60:916-921.
Realini et al (1994) "Proposed roles in protein-protein association and presentation of peptides by MHC class I receptors." FEBS Letters 348: 109-113.
Rechsteiner, et al (1996) "Pest sequences and regulation by proteolysis. "TIBS 21: 267-271., Jul. 1996.
Reilly RT, Gottlieb MB et al, "HER-2/neu Is a Tumor Rejection Target in Tolerized HER-2/neu Transgenic Mice" Cancer Res. Jul. 1, 2000; 60(13):3569-76.
Reiter et al. (1989) "Transfer RNA genes frequently serve as integration sites for prokaryotic genetic elements" Nucleic Acids Research 17(5) 1907-14.
Ren et al. "Macrophage migration inhibitory factor stimulates angiogenic factor expression and correlates withdifferentiation and lymph node status in patients with esophageal squamous cell carcinoma" Ann Surg. 242:55-63, (2005).
Renard et al. (2003) "HER-2 DNA and protein vaccine containing potent Th cell epitopes induce distinct protective and therapeutic antitumor responses in HER-2 transgenic mice" J. Immunol. 171(3):1588-95.
Repique (1992) "Immunosuppression derived from human B-lymphoblastoid and melanoma cell lines" Cancer Invest. 10(3):201-208.
Restifo et al., "Identification of Human Cancers Deficient in Antigen Processing" J. Exp. Med. 1993, 177, 265-272.
Roden et al. (2004) "Vaccination to prevent and treat cervical cancer" Hum. Pathol 35(8):971-82.
Rogers et al. "Amino acid sequences common to rapidly degraded proteins: the PEST hypothesis" Science. 234(4774):364-8. Oct. 17, 1986.
Rovero et al., "DNA Vaccination Against Rat Her-2/Neu p185 More Effectively Inhibits carcinogenesis Than Transplantable Carcinomas in Transgenic BALB/c Mice", The Journal of Immunology, 2000, 165:5133-5142.
Russmann et al. (1998) "Delivery of epitopes by the *Salmonella* type III secretion system for vaccine development" Science Jul. 24; 281(5376):565-8.
Safley, et al. (1991) "Role of Listeriolysin-o (LLO) in the T Lymphocyte response to infection with *Listeria Monocytogenes*" J Immunol. 146(10):3604-3616.

Sarmiento M et al., "IgG or IgM monoclonal antibodies reactive with different determinants on the molecular complex bearing lyt 2 antigen block t cell-mediated cytolysis in the absence of complement" J. Immunol. 125(6): 2665-72, 1980.
Scardino et al. (2002) "HER-2/neu and hTERT Cryptic Epitopes as Novel Targets for Broad Spectrum Tumor Immunotherapy" The Journal of Immunology, vol. 168, 5900-5906.
Schafer et al. (1992) "Induction of a cellular immune response to a foreign antigen by a recombinant *Listeria monocytogenes* vaccine" J. Immunol. 149(1):53-59.
Scheirlinck et al. (1989) "Integration and expression of alpha-amylase and endoglucanase genes in the *Lactobacillus plantarum* chromosome" Appl. Environ. Microbiol. 55(9):2130-7.
Schlom, Jeffrey, Philip M. Arlen, and James L. Gulley. "Cancer vaccines: moving beyond current paradigms." Clinical Cancer Research 13.13 (2007): 3776-3782.
Schmidt et al. (1995) "Molecular Analysis of the Plasmid-Encoded Hemolysin of *Escherichia coli* O157:H7 Strain EDL 933" infection and Immunity, 63(3):1055-1061.
Schnupf et al., "Phosphorylation, ubiquitination and degradation of listeriolysin O in mammalian cells: role of the PEST-like sequence" Cellular Microbiology 8(2): 353-364, 2006.
Scortti et al. (2007) "The PrfA virulence regulon" Microbes Infect. Aug; 9(10):1196-207.
Seavey et al., "A novel human her-2/neu chimeric molecule expressed by *listeria monocytogenes* can elicit potent HLA-A2 restricted CD8-positive T-cell responses and impact the growth and spread of her-2/neu positive breast tumors", Clinical Cancer Research, The American Association for Cancer Research 2009, vol. 15, No. 3, pp. 924-932.
Seavey et al. "An anti-vascular endothelial growth factor receptor 2/fetal liver kinase-1 *Listeria monocytogenes* anti-angiogenesis cancer vaccine for the treatment of primary and metastatic Her-2/neu+ breast tumors in a mouse model" The Journal of Immunology. May 1, 2009; 182(9):5537-46.
Sewell et al. "Recombinant Listeria Vaccines Containing PEST Sequences Are Potent Immune Adjuvants for the Tumor-Associated Antigen Human Papillomavirus-16 E7" Cancer Res; 64:8821-8825. (2004).
Serth et al., "Increased Levels of Human Papillomavirus Type 16 DNA in a Subset of Prostate Cancers" Cancer Res.1999 15; 59(4):823-5.
Sewell et al. (2004) "Regression of HPV-positive tumors treated with a new *Listeria monocytogenes* vaccine" Arch. Otolaryngol Head Neck Surg. 130:92-97.
Shen et al. (1998) "Compartmentalization of bacterial antigens: differential effects on priming of CD8 T cells and protective immunity" Cell Feb. 20; 92(4):535-45.
Shen, et al. .(1998) "*Listeria monocytogenes* as a probe to study cell-mediated immunity" Curr. Opin. Immunol. 10(4):450-458.
Shen, H. et al. (Apr. 25, 1995). "Recombinant *Listeria monocytogenes* as a Live Vaccine Vehicle for the Induction of Protective Anti-Viral Cell-Mediated Immunity," Proc. Natl. Acad Sci. USA 92: 3987-3991.
Shetron-Rama et al. (2002) "Intracellular induction of *Listeria monocytogenes* actA expression" Infect. Immun. 70:1087-1096.
Shimizu et al. (1994) "Effects of CD4+ and CD8+ T cells in tumor-bearing mice on antibody production" Cancer Immunol Immunother. 38(4):272-276.
Silverman et al. "Expression of cmyc, c-raf-1, and c-Ki-ras in Azaserine-Induced pancreatic carcinomas and growing pancreas in rats", Mol. Carcinog 3(6):379-86, 1990.
Singh et al. (2005) "Fusion to Listeriolysin O and delivery by *Listeria monocytogenes* enhances the immunogenicity of HER-2/neu and reveals subdominant epitopes in the FVB/N mouse" J. Immunol. Sep. 15; 175(6):3663-73.
Singh et al., "Immunoediting sculpts tumor epitopes during immunotherapy", Cancer Res. 2007, 67, pp. 1887-1892.
Sirard et al (1997) "Intracytoplasmic delivery of Lidteriolysin O by a vaccinal strain of *Bacillus anthracis* induces CD8-mediated protection against *listeria monocytogenes*." J Immun., vol. 159, pp. 4435-4443.

(56) References Cited

OTHER PUBLICATIONS

Skinner et al. "Use of the Glu-Glu-Phe C-terminal Epitope for Rapid Purification of the Catalytic Domain of Normal and Mutant ras GTPase-activating Proteins." J. Biol. Chem., 266:15163-15166, (1991).
Skoble, J. et al. (Aug. 7, 2000). "Three Regions Within ACTA Promote ARP2/3 Complex-Mediated Actin Nucleation and *Listeria Monocytogenes* Motility," The Journal of Cell Biology 150(3):527-537.
Skolnick, et al. (2000) "From genes to protein structure and function: novel applications of computational approached in the genomic era" Trends in Biotech. 18(1):34-39.
Slifka et al. (1996) "Antiviral cytotoxic T-cell memory by vaccination with recombinant *Listeria monocytogenes*" J. Virol. 70(5):2902-10.
Smith et al. (1995) "The two distinct phospholipases C of *Listeria monocytogenes* have overlapping roles in escape from a vacuole and cell-to-cell spread" Infect. Immun. 63 4231-4237.
Smith, G.A. et al. (Sep. 1995). "Asymmetric Distribution of the *Listeria monocytogenes* ActA Protein is Required and Sufficient to Direct Actin-Based Motility," Molecular Microbiology 17:945-951;.
Souders et al. (2006) "In vivo bactofection: *listeria* can function as a DNA-cancer vaccine" DNA Cell Biol. Mar.; 25(3):142-51.
Stahl et al. (1984) "Replacement of the *Bacilius subtilis* subtilisin structural gene with an in vitro-derived deletion mutation" J. Bacteriol 158:411-418.
Starks et al. (2004) "*Listeria monocytogenes* as a vaccine vector: virulence attenuation or existing antivector immunity does not diminish therapeutic efficacy" J. Immunology 173:420-427.
Stitz et al. (1990) "Characterization and Immunological properties of influenza a virus nucleoprotein (NP): cell-associated NP isolated from infected cells or viral NP expressed by vaccinia recombinant virus do not confer protection" J Gen Virol. 71(Pt 5):1169-1179.
Stover et al., "New Use of BCG for Recombinant Vaccines", Nature 1991, 351, 456-460.
Strugnell et al. (1990) "Stable expression of foreign antigens from the cheomosome of *Salmonella typhimurium* vaccine strains" Gene 88:57-63.
Stryer et al., "Levels of structure in protein architecture", (1998) Biochemistry, Third Edition, WH Freeman Company, New York, 31-33.
Sun et al. (1990) "Isolation of *Listeria monocytogenes* small-plaque mutants defective for intracellular growth and cell-to-cell soread" Infect. Immun. 58 3770-3778, Nov. 1990.
Tanabe et al.(1999) "Induction of Protective T Cells against *Listeria monocytogenes* in Mice by Immunization with a Listeriolysin O-Negative Avirulent Strain of Bacteria and Liposome-Encapsulated Listeriolysin O" Infect. Immun. 67(2):568-575.
Thull et al., "Recognition and management of hereditary breast cancer syndromes", The Oncologist, 2004; 9:13-24.
Tilney et al. (1989) "Actin filaments and growth, movement and spread of the intracellular bacterial parasite, *Listeria monocytogenes*" J Cell Biol. Oct.; 109(4 Pt 1):1597-608.
Tite et al., "Anti-viral immunity induced by recombinant nucleoprotein of Influenza A virus" 1990, Immunology 70:540-546.
Townsend et al., "Tumor Rejection after Direct Costimulation of CD8+ T Cells by B7-Transfected Melanoma Cells", Science 1993, 259, 368-370.
Travis J., "A Stimulating New Approach to Cancer Treatment", Science 1993, 259, 310-311.
Trieu-Cuot et al, "Suttle Vectors Containing a Multiple Cloning Site and lacZ x Gene for Conjugal transfer of DNA From *Eshcerichia Coli* to Gram-positive Bacteria", Gene 1991, 102, 99-104.
Ulmanen et al., "Transcription and Translation of Foreign Genes in *Bacilus subtilis* by the Aid of a Secretion Vector", 1985, J. Bacteriol. 162:176-182.

Uneda et al. "Anti-endoglin monoclonal antibodies are effective for suppressing metastasis and the primary tumors by targeting tumor vasculature" International journal of cancer. Sep. 15, 2009;125(6):1446-53.
Vallbohmer et al. "Molecular determinants of cetuximab efficacy" J Clin Oncol.; 23:3536-44. (2005).
Vasil et al. (1982) "Cloning of a phosphate-regulated hemolysin gene (phospholipase C) from *Pseudomonas aeruginosa*" J. Bacteriol. Oct.; 152(1):431-40.
Vazquez-Boland et al. (1992) "Nucleotide sequence of the lecithinase operon of *Listeria monocytogenes* and possible role of lecithinase in cell-to-cell spread" Infect. Irnmun. 60:219-230.
Verch et al. (2004) "*Listeria monocytogenes*-based antibiotic resistance gene-free antigen delivery system applicable to other vectors and DNA vaccines" Infect. Immun. Nov.; 72(11):6418-25.
Verma et al. (1995) "Delivery of class I and class II MHC-restricted T-cell epitopes of *listeriolysin* of *listeria monocytogenes* by attenuated *salmonella*", Vaccine, vol. 13, No. 2, pages. 142-150.
Vines A. et al. Identification and Characterization of Nucleotide Sequence Difference in Three Virulence-Associated Genes of *Listeria monocytogenes* Strains Representing Clinically Important Serotypes, Current Microbiol. May 1998, vol. 36, No. 5, pp. 309-318.
Vitiello et al., "Development of a Lipopeptide-based therapeutic vaccine to treat chronic HBV infection", J. Clin. Invest., Jan. 1995, 95(1):341-349.
Walker et al. (1994) "Tumor growth alters T cell and macrophage production of and responsiveness to granulocyte-macrophage colony-stimulating factor: partial dysregulation through interleukin-10" Cell. Immunol. 154(1):342-357.
Ward et al., "Construction and characterization of a series of multi-copy promoter—probe plasmid vectors for *Streptomyces* using the aminoglycoside phsophotransferase gene from Tn5 as indicator", 1986, Mol. Gen. Genet. 203:468-478.
Watson et al. (1991) "Splenic macrophages from tumor-bearing mice co-expressing MAC-1 and MAC-2 antigens exert immunoregulatory functions via two distinct mechanisms" J Leukoc Biol 49(2):126-138.
Wei et al. (2005) "*Listeria monocytogenes* phosphatidylinositol-specific phospholipase C has evolved for virulence by greatly reduced activity on GPI anchors" Proc. Natl. Acad. Sci. USA 102:12927-12931.
Wei et al., "Protection against mammary tumor growth by vaccination with full length, modified human ErbB-2 DNA", Int. J. Cancer, May 31, 1999; 81(5):748-54.
Weidt et al. (1994) "CD8+ T lymphocyte-mediated antiviral immunity in mice as a result of injection of recombinant viral proteins" J Immunol. Sep. 15; 153(6):2554-61.
Weiskirch, et al (1997) " *Listeria monocytogenes*: a potent vaccine vector for neoplastic and infectious disease." Immunol. Rev, vol. 158, pp. 159-169.
Welch, M.D. et al. (Jul. 3, 1998). "Interaction of Human Arp2/3 Complex and the *Listeria monocytogenes* ActA Protein in Actin Filament Nucleation," Science 281:105-108; pa-998020.
Wells et al. "Cassette mutagenesis: an efficient method for generation of multiple mutations at defined sites" Gene.; 34(2-3):315-23. (1985).
Wells et al. "D. A. Importance of hydrogen-bond formation in stabilizing the transition state of subtilisin" Phil. Trans. R. Soc. Lond. A 317, 415-423 (1986).
Wilson et al. "Expression of a Leishmania chagasi antigen in *Listeria Monocytogenes* for use in vaccine development; recombinant Leishmania chagasi antigen gene expression in *Listeria Monocytogenes* using vector plasmid phly-Lcr1; potential recombinant vaccine", 1995 Am. J. Trop. Med. Hyg. 53(2) Suppl:132 Abstract only.
Wirth et al. (1986) "Highly efficient protoplast transformation system for *Streptocococus facecalis* and a new *Escherichia coli*-S *faecalis* suttle vector" J. Bacteriol. 165(3):831-6.
Wu et al., "Engineering an intracellular pathway for major histocompatibilty complex class II presentation of antigens", Proc. Natl. Acad. Sci. USA 1995 92:11671-5.

(56) References Cited

OTHER PUBLICATIONS

Wuenscher et al., "Gene Disruption by Plasmid Integration in *Listeria monocytogenes*: Insertional Inactivation of the Listeriolysin Determinant lisA", Mol. Gen. Genet., 1991, 228, 177-182.

Young J.F. et al., "Cloning and Expression of Influenza Virus Genes", The Origins of Pandemic Influenza Viruses, W.G. Laver, eds., Elsevier Science Publishing Co., Inc., NY, 1983, p. 129.

Young et al. (1992) "Tumor-derived cytokines induce bone marrow suppressor cells that mediate immunosuppression through transforming growth factor beta" Cancer Immunol Immunother 35(1):14-18.

Young et al. (1995) "Holins:form and function in bacteriophage lysis" FEMS Microbiol Rev Aug. 17(1-2):191-205.

Youngman, "Plasmid Vectors for Recovering and Exploiting Transpositions in *Bacillus* and Other Gram-Positives" 1987, pp. 79-103, in K. Hardy (ed.), Plasmids A Practical Approach, IRL Press, Oxford.

Zhang et al. (1993) "Functional replacement of the hemolysin a transport signal by a different primary sequence" Proc Natl Acad Sci USA May 1; 90(9):4211-5.

Zhang et al., "Selection of Tumor Antigens as Targets for Immune Attack Using Immunohistochemistry: Protein Antigens", Clin. Cancer Res. 1998 4:2669-2676.

Zoller et al. "Oligonucleotide-directed mutagenesis of DNA fragments cloned into M13 vectors" Methods Enzymol.; 100:468-500, (1983).

Zoller et al. "Oligonucleotide-directed mutagenesis using M13-derived vectors: an efficient and general procedure for the production of point mutations in any fragment of DNA" Nucleic Acids Res. 10(20):6487-500. Oct. 25, 1982.

Zoller et al. "Oligonucleotide-Directed Mutagenesis: A Simple Method Using Two Oligonucleotide Primers and a Single-Stranded DNA Template" DNA. 3(6): 479-488. Dec. 1984.

Zubai R et al. In: Vaccines for human Papillomavirus Infection and Anogential Disease (ed. Robert W. Tindle) 1999, pp. 173-192.

* cited by examiner

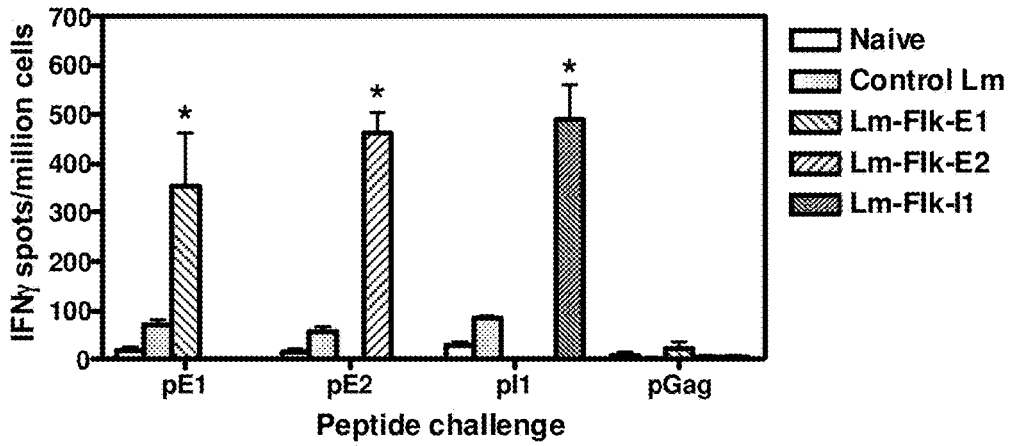

FIG. 1C

MESKALLAVALWFCVETRAASVGLPGDFLHPPKLSTQKDILTILANTTLQITCRGQRDLDWLWPN
AQRDSEERVLVTECGGGDSIFCKTLTIPRVVGNDTGAYKCSYRDVDIASTVYVYVRDYRSPFIAS
VSDQHGIVYITENKNKTVVIPCRGSISNLNVSLCARYPEKRFVPDGNRISWDSEIGFTLPSYMISYA  ⎤
GMVFCEAKINDETYQSIMYIVVVVGYRIYDVILSPPHEIELSAGEKLVLNCTARTELNVGLDFTWHS  ⎬ Flk-E1
PPSKSHHKKIVNRDVKPFPGTVAKMFLSTLTIESVTKSDQGEYTCVASSGRMIKRNRTFVRVHTK   ⎦
PFIAFGSGMKSLVEATVGSQVRIPVKYLSYPAPDIKWYRNGRPIESNYTMIVGDELTIMEVTERDA
GNYTVILTNPISMEKQSHMVSLVVNVPPQIGEKALISPMDSYQYGTMQTLTCTVYANPPLHHIQW
YWQLEEACSYRPGQTSPYACKEWRHVEDFQGGNKIEVTKNQYALIEGKNKTVSTLVIQAANVSA
LYKCEAINKAGRGERVISFHVIRGPEITVQPAAQPTEQESVSLLCTADRNTFENLTWYKLGSQATS  ⎤
VHMGESLTPVCKNLDALWKLNGTMFSNSTNDILIVAFQNASLQDQGDYVCSAQDKKTKKRHCLV  ⎬ Flk-E2
KQLIILERMAPMITGNLENQTTTIGETIEVTCPASGNPTPHITWFKDNETLVEDSGIVLRDGNRNLTI
RRVRKEDGGLYTCQACNVLGCARAETLFIIEGAQEKTNLE*VILVGTAVIAMFFWLLLVIVLRTVKR*  ⎦
ANEGELKTGYLSIVMDPDELPLDERCERLPYDASKWEFPRDRLKLGKPLGRGAFGQVIEADAFGI  ⎤
DKTATCKTVAVKMLKEGATHSEHRALMSELKILIHIGHHLNVVNLLGACTKPGGPLMVIVEFCKFG  ⎬ Flk-I1
NLSTYLRGKRNEFVPYKSKGARFRQGKDYVGELSVDLKRRLDSITSSQSSASSGFVEEKSLSDV
EEEEASEELYKDFLTLEHLICYSFQVAKGMEFLASRKCIHRDLAARNILLSEKNVVKICDFGLARDI   ⎦
YKDPDYVRKGDARLPLKWMAPETIFDRVYTIQSDVWSFGVLLWEIFSLGASPYPGVKIDEEFCRR
LKEGTRMRAPDYTTPEMYQTMLDCWHEDPNQRPSFSELVEHLGNLLQANAQQDGKDYIVLPMS
ETLSMEEDSGLSLPTSPVSCMEEEEVCDPKFHYDNTAGISHYLQNSKRKSRPVSVKTFEDIPLEE
PEVKVIPDDSQTDSGMVLASEELKTLEDRNKLSPSFGGMMPSKSRESVASEGSNQTSGYQSGY
HSDDTDTTVYSSDEAGLLKMVDAAVHADSGTTLRSPPV

FIG. 2A

Mφ Infection Assay

Listeria-Alexa488/CD11b-PE/Nucleus-DAPI

Lm-LLO-Flk-E1

Lm-LLO-Flk-E2

Lm-LLO-Flk-I1

No Lm

Control Lm

MELAAWCRWGFLLALLPPGIAGTQVCTGTDMKLRLPASPETHLDMLRHLYQGCQVVQGN
LELTYVPANASLSFLQDIQEVQGYMLIAHNQVKRVPLQRLRIVRGTQLFEDKYALAVLD
NRDPQDNVAASTPGRTPEGLRELQLRSLTEILKGGVLIRGNPQLCYQDMVLWKDVFRKN
NQLAPVDIDTNRSRACPPCAPACKDNHCWGESPEDCQILTGTICTSGCARCKGRLPTDC
CHEQCAAGCTGPKHSDCLACLHFNHSGICELHCPALVTYNTDTFESMHNPEGRYTFGAS
CVTTC[PYNYLSTEV]GSCTLVCPPNNQEVTAEDGTQRCEKCSKPCARVCYGLGMEHLRGA
RAITSDNVQEFDGCKKIFGSLAFLPESFDGDPSSGIAPLRPEQLQVFETLEEITGYLYI
SAW[PDSLRDLSVFQNLRIIRGRILHDGAYSLTLQGLGIHSLGLRSLRELGSG[LALI**HRN
AHLCFVFTVPWDQLFRNPHQALLHSGNR▓EEDcgleGLVCNSLCAHGHCWG[PGPTQCVN
CS]HFLRGQECVEECRVWKGLPREYVSDKRCLPCHPECQPQNSSE**TCFGSEADQCAACAH
YKDSSSCVARCPSGVKPDLSYMPIWKYPDEEGICQPCPINCTHSCVDLDERGCPAEQRA
SPVTFIIATVEGVLLFLILVVVVGILIKRRQKIRKYTMRRLLQETELVEPLTPSGAM[**P
NQAQMRII**]KETE*LRKVKV*[GSGAFGTVYKGI]WIPDGENVKIPVAIKVLREN[**TSPKANKE
ILDEAYVMAGVGS[PYV**SRLLGI]CLT*STV*QLV*TQLMPYGCLLDHVREHRGRLGSQDLLNW
CVQIAKGMSYLEDVRLVHRDLAARNVLVKSPNHV[KT*TDFGLAR*L]LDIDETEYHADGGKV
PIKWMALESILRRRFTHQSDVWSYGVTVWELMTFGAKPYDGIPAREIPDLLEKGERLPQ
PPICTIDVYMIMVKCWMIDSEC[RPR*FRELVS*E**]FSRMARDPQRFVVIQNEDLGMDSTFYR
SLLEDDDMGDLVDAEEYLVPQQGFFSPDPTPGTGSTAHRRHRSSSTRSGGGELT▓LEP
SE▓GPPRSPLAPSEGAGSDVFDGDLAMGVTKGLQSLSPHDLSP[LQRYSEDPTI]PLPPET
DGYVAPLACSPQPEYVNQSEVQPQPFLTPEGPLPPVRPAGATLERPKTLSPGKNGVVKD
VFAFGGAVENPEYLVPREGTASPPHPSPAFSPAFDNLYYWDQNSSEQGPPPSNFEGTPT
AENPEYLGLDVPV Ctrl

FIG. 10B

MELAAWCRWGFLLALLPPGIAGTQVCTGTDMKLRLRLPASPETHLDMLRHLYQGCQVVQGNLELTYVPANA
SLSFLQDIQEVQGYMLIAHNQVKRVPLQRLRIVRGTQLFEDKYALAVLDNRDPQDNVAASTPGRTPEGL
RELQLRSLTEILKGGVLIRGNPQLCYQD▓LWK▓VFRKNNQLAPVDIDTNRSRACPPCAPACKDNHCWG
ESPEDCQILTGTICTSGCARCKGRLPTDCCHEQCAAGCTGPKHS▓LACLHFNHSGICELHCPA▓VTYN
TDTFESMHNPEGRYTFGASCVTTC[PYNYLSTEV]GSCTLVCPFNNQEVTAEDGTQRCEKCSKPCARVCY
GLGMEH▓RG▓▓▓SD▓VQ▓F▓▓KIFGSLAFLPESFDG▓PSSGIAPLRPEQLQVFETLEEITGYLYI
SAW[PDSLRDLSVFQNLRIIRGRILHDGAYSLTLQGLGIHSLGLRSLREL]GSG[LALIHRNAHL▓V▓V
P▓DQ[LR▓▓▓H▓LLH]▓NR▓▓DcgleGLVCNSLCAHGHCWG[PGPTQCVNCS**]HFLRGQECVEECRVWK
GLPREYVSDKRCLPCHPECQPQNSSETCFGSEADQCAACAH[KDSSSCVARCPSGVKPDLSYMPIWKYP
DEEGIC▓▓P▓NTHSCVDLDERG▓**PAEQRASPVTFIIATVEGVLLFLILVVVGILIKRRQKIRKYT
MRRLLQETELVEPLTPSGAM[PNQAQMRII]KETE*LRKVKV*I[GSGAFGTVYKGI]WIPDGENVKIPVAIKV
LREN[TSP▓▓KE]*LDEAYVMAGVGS*[PYV*SRLLGI*]CLT*STV*QLV*TQL*MPYGCLLDHVREHRGRLGSQDL
LNWCVQIAKGMSYLEDVRLVHRDLAARNVLVKSPNHV[KT*TDFGLAR*L]LDIDETEYHADGGKVPIKWMA
LESILRRRFTHQSDVWSYGVTVWELMTFGAKPYDGIPAREIPDLLEKGERLPQPPICTIDVYMIMVKCW
MIDSEC[RPR*FRELVS*E]FSRMARDPQRFVVIQNEDLGMDSTFYRSLLEDDDMGDLVDAEEYLVPQQGFF**
▓PDPTPGTGSTAHRR▓RSSSTRSGGGELT▓LGLEPSE▓GPPRSPLAPSEGAGSDVFDGDIAMGVTKGLQS
LSPHDLSP[LQRYSEDPTI]PLPPETDGYVAPLACSPQPEYVNQSEVQPQPPLTPEGPLPPVRPAGATLE
RPKTLSPGKNGVVKDVFAFGGAVENPEYLVPREGTASPPHPSPAFSPAFDNLYYWDQNSSEQGPPPSNF
EGTPTAENPEYLGLDVPV

MELAAWCRWGFLLALLPPGLAGPQVCTGTDMKLRLPASPETHLIMLRHLYQGQVVQGNLELTYVPA A
SLSFIQDIQEVQGYMLIAHNQVKRVPLQRLRIVRGTQLFEDKYALAVLDNRDPQDNV ASI PGRTPEGL
RELQLRSLTEIIKGGVLIRGNPQLCYQDMVLWKDVFRKNNQIAPVDIDTNRSRACPFCAPACKINHCWG
ESPEDCQILTGTICTSGCARCKGRLPTDCCHEQCAAGCTGPKHSDCIACLHENHSGICELHCPALVTYN
TDTFESMHNPEGRYTFGASCVTPQ PYNYLST V CTLVC E NQEVTAEDGTQRCEKCSKPC RV
G IRGARAITSDMVQEFDGCKKIFGSLAFLPESFDGDPSSGTAPLRPEQLQVFETLEEPTGYLYI
SAWPDSLFDLSVE QNLRITRGRTLHDGAYSLTLQGLGITSIGLRSIRELGSGLALIHRNAHLCFV TPV
PWDQ ERNPHQA IHSGNRPEEDαgLeGLVCNSLCAHGHCWG FGPTQC VNCS HFLRGQECVEECRWK
GLPREYVSDKRCLPCHPECQPQNSSETCFGSEADCAACAHYKDSSSCVARCPSGVKPI SYMPT K P
DEEGIC F NCTHSCVDLDERGCPAEQRASPVTFIIATVEGVLLPLILVVVVGILLKRRQKIRKYT
MRRLLQETEIVEPLTPSGAM ENQAQMRTIIKETE IRKVKVLGSGAFGTVYKG WIPDGENVKIPVAIKV
LRENTSPKANKE ILDEAYVMAGVGSPYVSRLLGICLTSTVQLVTQIMPYGCLLDHVREHRCRLGSQDL
LNWCVQIAKGMSYLEDVRLVHRDLAARNVLVKSPNHV KITDFGLARL LDIDETEYHADGGKVPIKWMA
LESTIRRRFTHQSDVWSYGVTVWELMTFGAKPYDGIPARETFDLLEKGERLPQPPICFIDVYMIMVKCW
MIDSECRPEREREIVSR FSRMARDPQRFVVIQNEDLGMDSTFYRSLIEDDDMGDLVDAEEYLVPL GFF
SEDPTP T HRRHRSSSTR G GELTLGLEPSEEGPPRSPIAPSEGAGSDVFDGDLAMGVIKGLQS
LSPHDLSPLQRYSEDPTI PLPPETDGVAPLACSPQPEYVNQSEVQPQPPLPPEGPLPPVRPAGAILE
RPKTLSEGKN3WKIVFAEGGAVENPEYLVPREGTASPPHPSPAFSPAFDNLYYWDQNSSEQG PSNF
EGTPTAENPEYLGLDVFV

|1
FIG. 10D

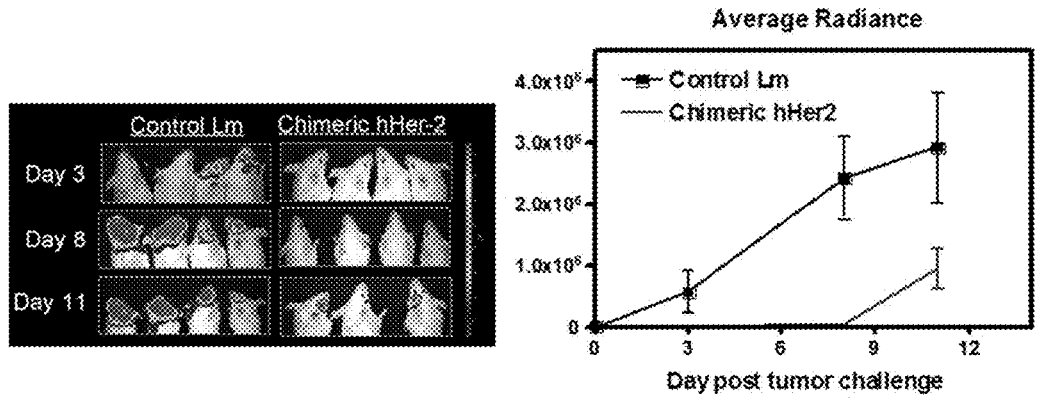

FIG. 11A

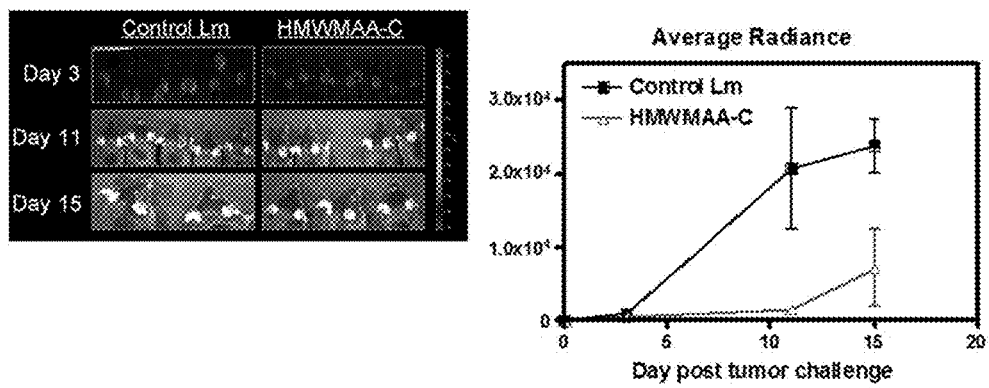

FIG. 11B

MDRGVLPLPITLLFVIYSEVPTTGLAERVGCDLQPVDPTRGEVTFTTSQVSEGC
VAQAANAVREVHVLFLDFPGMLSHLELTLQASKQNGTETREVFLVLYSNKN
VFVKFQAPEIPLHLAYDSSLVIFQGQPRVNITVLPSLTSRKQILDWAATKGAIT
SIAALDDPQSIVLQLGQDPKAPFLCLPEAHKDMGATLEWQPRAQTPVQSCR
LEGVSGHKEAYILRILPGSEAGPRTVTVMMELSCTSGDAILILHGPPYVSWFID
INHSMQILTTGEYSVKIFPGSKVKGVELPDTPQGLIAEARKLNASIVTSFVELPL
VSNVSLRASSCGGVFQTTPAPVVTTPPKDTCSPVLLMSLIQPKCGNQVMTLALN
KKHVQTLQCTITGLTFWDSSCQAEDTDDHLVLSSAYSSCGMKVTAHVVSNE
VIISFPSGSPPLRKKVQCIDMDSLSFQLGLYSPHFLQASNTIELGQQAFVQVS
VSPLTSEVTVQLDSCHLDLGPEGDMVELIQSRTAKGSCVTLLSPSPEGDPRESF
LLRVYMVPTPTAGTLSCNLALRPSTLSQEVYKTVSMRLNVVSPDLSGKGLVLP
SVLGITFGAFLIGALLTAALWYIYSHTRGPSKREPVVAVAAPASSESSSTNHSIGSTQS
TPCSTSSMA

Lm-LLO-CD105

FIG. 12

MDRGVLPLPLPTLLFVIYSFVPTTGLAERVGCDLQPVDPTRGEVTFTTSQVSEGCVAQAA
NAVREVHVLFLDFPGMLSRLELTLQASKQNGTETREVFLVLVSNKNVFVKFQAPEIP   Lm-LLO-CD105A
LHLAYDSSLVIFQGQPRVNITVLPSLTSRKQILDWAATKGAITSIAALDDPQSIVLQLG
QDPKAPFLCLPEAHKDMGATLEWQPRAQTPVQSCRLEGVSGHKEAYILRILPGSEAG
PRTVTVMMELSCTSGDAILILHGPPYVSWFIDINHSMQILTTGEYSVKIFPGSKVKGV
ELPDTPQGLIAEARKLNASIVTSFVELPLVSNVSLRASSCGGVFQTTPAFVVTTPPKDTCS
PVLLMSLIQPKCGNQVMTLALNKKHVQTLQCTTTGLTFWDSSCQAEDTDDHLVLSS
AYSSCGMKVTAHVVSNEVIISFPSGSPPLRKKVQCIDMDSLSFQLGLYLSPHFLQASNT
IELGQQAFVQVSVSPLTSEVTVQLDSCHLDLGPEGDMVELIQSRTAKGSCVTLLSPSP   Lm-LLO-CD105B
EGDPRFSFLLRVYMVPTPTAGTLSCNLALRPSTLSQEVYKTVSMRLNVVSPDLSGKG
LVLPSVLGHTFGAFLIGALLTAALWYIYSHTRGPSKREPVVAVAAPASSESSSTNHSIGSTQ
STPCSTSSMA

Lm CD105A: AGPRTVTVM ($D^b$)
Lm CD105B: AYSSCGMKV ($K^b$)

FIG. 13A

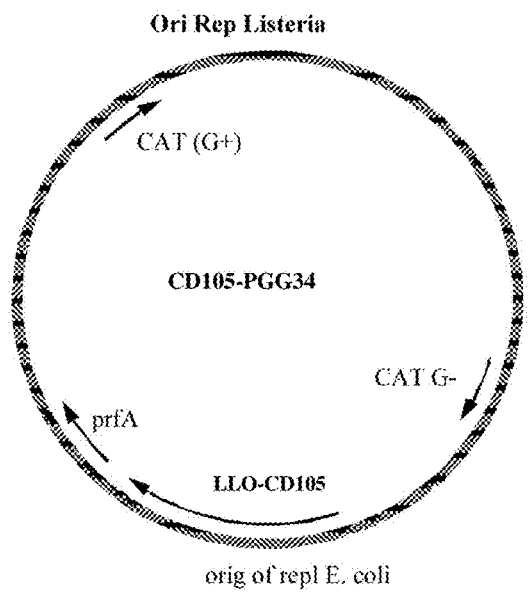

FIG. 13B

1st immunization on Day 1

1st immunization on Day 4

COMPOSITIONS COMPRISING ANGIOGENIC FACTORS AND METHODS OF USE THEREOF

CROSS-REFERENCE TO RELATED APPLICATIONS

This application is a divisional of U.S. patent application Ser. No. 15/225,205, filed Aug. 1, 2016, which is a continuation of U.S. patent application Ser. No. 14/304,689, filed Jun. 13, 2014, which is a divisional of U.S. patent application Ser. No. 13/254,607, filed Jan. 23, 2012 now U.S. Pat. No. 8,778,329, which is a National Phase Application of PCT International Application No. PCT/US10/26257, International Filing Date Mar. 4, 2010, claiming priority of U.S. Provisional Patent Application No. 61/157,367, filed Mar. 4, 2009, all of which are hereby incorporated by reference.

GOVERNMENT INTEREST STATEMENT

This invention was made with government support under grant number CA109253 awarded by the National Institutes of Health. The government has certain rights in the invention.

FIELD OF THE INVENTION

The present invention provides recombinant *Listeria* strains comprising an angiogenic factor, recombinant polypeptides comprising an angiogenic factor operatively linked to a polypeptide comprising a PEST-like sequence, recombinant nucleotide molecules encoding same, related vaccines, and immunogenic and therapeutic methods utilizing same.

BACKGROUND OF THE INVENTION

Targeting cells involved in angiogenesis cripples rapidly growing tumors by limiting the oxygen and nutrients supply or, depending on the strategy employed, increasing the susceptibility of tumor cells to chemotherapy by enhancing the efficiency of a delivered drug via vascular network reorganization. Resistance of tumor cells to anti-angiogenesis treatment has been observed in mouse systems and reported for human studies for several different treatments. Additionally, the tumor microenvironment (TME) recruits myeloid-derived suppressor cells (MDSC) that are responsible for the necessary angiogenic switch needed for tumor growth and eventual dissemination.

Studies performed by several investigators have repeatedly shown the importance of targeting tumor angiogenesis because of its central role in invasion, growth, and metastasis. Since tumor cells frequently mutate in response to therapy or downregulate MHC class I molecules required for T cell-mediated responses, targeting endothelial cells and pericytes, which are essential for tumor survival and may lack the immunosuppressive mechanisms deployed by tumors, would be advantageous.

However, thirty years after angiogenesis was shown to play an enabling role in cancer, modern medicine is still trying to develop novel compounds and therapeutics to target the tumor vasculature. However, most therapeutics require multiple rounds of administration and can have toxic side effects.

SUMMARY OF THE INVENTION

In one embodiment, the present invention provides a recombinant *Listeria* strain expressing an angiogenic factor.

In another embodiment, the present invention provides a vaccine comprising a recombinant *Listeria* strain expressing an angiogenic factor.

In one embodiment, the present invention provides a recombinant *Listeria* strain expressing an angiogenic factor, wherein said angiogenic factor is a vascular endothelial growth factor receptor-2 (VEGFR2) polypeptide, an endoglin, or an immunogenic fragment thereof.

In another embodiment, the present invention provides a method of inducing an anti-VEGFR2 immune response in a subject, comprising administering to said subject a composition comprising a recombinant *Listeria* strain expressing a vascular endothelial growth factor receptor-2 (VEGFR2) polypeptide or an immunogenic fragment thereof.

In another embodiment, the present invention provides a method of treating a cancer in a subject, comprising the step of administering to said subject a composition comprising a recombinant *Listeria* strain expressing an angiogenic factor.

In another embodiment, the present invention provides a method of inhibiting or suppressing a cancer in a subject, comprising the step of administering to said subject a composition comprising a recombinant *Listeria* strain expressing an angiogenic factor.

In another embodiment, the present invention provides a method of preventing the recurrence of a tumor in a subject, comprising the step of administering to said subject a composition comprising a recombinant *Listeria* strain expressing an angiogenic factor.

In another embodiment, the present invention provides a method of inhibiting metastasis of a tumor in a subject, comprising the step of administering to said subject a composition comprising a recombinant *Listeria* strain expressing an angiogenic factor.

In another embodiment, the present invention provides a recombinant polypeptide comprising an angiogenic factor operatively linked to a polypeptide comprising a PEST-like sequence.

In another embodiment, the present invention provides a vaccine comprising a recombinant polypeptide comprising an angiogenic factor operatively linked to a polypeptide comprising a PEST-like sequence and an adjuvant.

In another embodiment, the present invention provides a recombinant vaccine vector encoding an angiogenic factor operatively linked to a polypeptide comprising a PEST-like sequence.

In another embodiment, the present invention provides a method of inducing an anti-VEGFR2 immune response in a subject, comprising administering to said subject an immunogenic composition comprising a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of treating a cancer in a subject, comprising the step of administering to said subject a composition comprising a recombinant polypeptide comprising an angiogenic factor operatively linked to a polypeptide comprising a PEST-like sequence.

In another embodiment, the present invention provides a method of inhibiting or suppressing a cancer in a subject, comprising the step of administering to said subject a composition comprising an angiogenic factor operatively linked to a polypeptide comprising a PEST-like sequence.

In another embodiment, the present invention provides a method of preventing the recurrence of a tumor in a subject, comprising the step of administering to said subject a composition comprising an angiogenic factor operatively linked to a polypeptide comprising a PEST-like sequence.

In another embodiment, the present invention provides a method of inhibiting metastasis of a tumor in a subject, comprising the step of administering to said subject a composition comprising an angiogenic factor operatively linked to a polypeptide comprising a PEST-like sequence.

In another embodiment, the present invention provides a nucleotide molecule encoding a recombinant polypeptide comprising an angiogenic factor operatively linked to a polypeptide comprising a PEST-like sequence.

In another embodiment, the present invention provides a vaccine comprising a nucleotide molecule encoding an angiogenic factor operatively linked to a polypeptide comprising a PEST-like sequence and an adjuvant.

In another embodiment, the present invention provides a recombinant vaccine vector comprising a nucleotide molecule encoding an angiogenic factor operatively linked to a polypeptide comprising a PEST-like sequence.

In another embodiment, the present invention provides a method of inducing an anti-VEGFR2 immune response in a subject, comprising administering to said subject an immunogenic composition comprising a nucleotide molecule encoding a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of treating a cancer in a subject, comprising the step of administering to said subject a composition comprising a nucleotide molecule encoding a recombinant polypeptide an angiogenic factor operatively linked to a polypeptide comprising a PEST-like sequence.

In another embodiment, the present invention provides a method of inhibiting or suppressing a cancer in a subject, comprising the step of administering to said subject a composition comprising a nucleotide molecule encoding an angiogenic factor operatively linked to a polypeptide comprising a PEST-like sequence.

In another embodiment, the present invention provides a method of preventing the recurrence of a tumor in a subject, comprising the step of administering to said subject a composition comprising a nucleotide molecule encoding an angiogenic factor operatively linked to a polypeptide comprising a PEST-like sequence.

In another embodiment, the present invention provides a method of inhibiting metastasis of a tumor in a subject, comprising the step of administering to said subject a composition comprising a nucleotide molecule encoding a recombinant polypeptide comprising an angiogenic factor operatively linked to a polypeptide comprising a PEST-like sequence.

BRIEF DESCRIPTION OF THE DRAWINGS

FIGS. 1A-1C show the design of the Flk-1/VEGFR2 expressing Lm-based constructs. FIG. 1A shows each gene fragment was cloned into the expression vector pGG34 fused to LLO and placed under the control of the hly promoter. FIG. 1B is a Western blot from culture supernatants showing expression of each fusion protein from the constructs listed. Polyclonal, rabbit, anti-PEST antibody was used for fusion protein detection (bottom), and mouse anti-LLO antibody was used for confirmation (top). Note that all lanes were taken from the same Western blot. FIG. 1C is a IFN-g ELISpot showing CD8+ T cell restricted responses ex vivo after immunization with each construct. The naive group was injected with PBS alone; all groups contained a control Lm group. Responses are to the corresponding mapped epitopes for each Flk fragment. N=5 per group. Graphs show Mean±SEM; *p<0.05, Mann-Whitney statistical test, experiment repeated once.

FIGS. 2A-2H show the design of the Flk-1/VEGFR2 expressing Lm-based constructs. FIG. 2A shows cloned regions boxed for each construct built, highlighted/bold amino acids show mapped CTL epitopes for $H2^{d/q}$ MHC I haplotype. FIG. 2B is a map of the flk gene showing one embodiment of the fragments used in the present invention. FIG. 2C is a cartoon showing how the flk fragments used in one embodiment of the present invention related to the various domains of the flk gene. FIGS. 2D-2H show a macrophage infection assay was performed as described in the methods. J774A.1 cells were incubated with Listeria constructs, washed, then incubated with Gentimycin, bacteria that were able to infect the macrophage and escape into the cytoplasm are shown in Alexa-488 (green), the PE CD11b+ halo (red) demarks the cell shape and size. All three constructs, Lm-LLO-Flk-E1 (FIG. 2D), Lm-LLO-Flk-E2 (FIG. 2E), Lm-LLO-Flk-I1 (FIG. 2F), were able to infect, grow, and escape the phagolysosome as evidenced by replication in J774A.1 macrophages, as compared to controls, no LM (FIG. 2G), and control Lm (FIG. 2H).

FIG. 3A shows NT-2 tumor volume ($mm^3$) from mice treated with each construct. Graph shows Mean±SEM; *p<0.05, Mann-Whitney statistical test, N=8 mice per group, experiment repeated twice. FIG. 3B shows IFN-g ELISpots showing epitope spreading to various Her-2/neu regions. Splenocytes from the 64-day time point were restimulated ex vivo with Her-2/neu peptide epitopes. Graph shows Mean±SEM; *p<0.05, Mann-Whitney statistical test, N=5 mice per group, experiment repeated once. FIGS. 3C-3G show mice were immunized thrice over the course of three weeks after the initial establishment of NT-2 tumors. In these FIGS. we show staining for the pan-endothelial marker CD31-PE and nucleus using DAPI. Isotype controls were used on sequential sections as shown to the right. All three constructs, Lm-LLO-Flk-E1 (FIG. 3D), Lm-LLO-Flk-E2 (FIG. 3E), Lm-LLO-Flk-I1 (FIG. 3F) and the control Lm (FIG. 3C) are shown. Quantitation of vessel density performed by Image Pro software. FIG. 3G shows Mean±SEM, *p<0.05, Mann-Whitney test, ns=not significant. FIGS. 3H-3J show staining for the pan-endothelial marker CD31-PE (FIG. 3H), the nucleus using DAPI (FIG. 3I), and the nuclear hypoxic marker Hypoxia Inducible Factor-1α (HIF-1α) (FIG. 3J).

FIG. 4A shows mice that had fully regressed tumors were re-challenged with NT-2 in the contra-lateral flank on day 100. A saline treated group was used as our negative control for tumor growth. FIG. 4B shows tumor volume for mice that grew tumors after re-challenge on day 100 of tumor free mice. Both graphs refer to a single experiment. Number of tumor free mice was 2/8 for Flk-E1 and Flk-I1 groups, the saline group had 5 mice.

FIG. 5A shows FVB/N wild-type (WT) or FVB/N transgenic (Tg) mice were injected with $1×10^6$ NT-2 cells s.c., tumors were allowed to grow until palpable before treatment started. Mice were immunized a total of three times, mean tumor sizes are shown here for up to 69 days post tumor inoculation. Graphs show Mean±SEM; *p<0.05, Mann-Whitney test, experiment repeated twice. FIG. 5B shows spleens were processed for IFN-g ELISpots, stimulated with various Her-2/neu peptides ex vivo, or a third party peptide as a negative control (pGag). Graphs show Mean±SEM; *p<0.05, Mann-Whitney test, experiment repeated once. FIGS. 5C-5D show tumors from each group were pooled and digested for TILs; here we show Her-2/neu specific T cells staining for CD8α and EC1 (FIG. 5C) or IC1 (FIG. 5D) specific tetramers. Significantly more Her-2/neu specific T cells are found in the wild type (WT) but not transgenic (Tg) mice; control Lm group shows low background. Experiment repeated once giving similar results.

FIG. 6A shows primary subcutaneous 4T1 tumors grow slower in Lm-LLO-Flk-1 protected animals. Mice were immunized thrice with each vaccine then injected with s.c. and i.v. with 50,000 4T1 cells. Graph shows Mean±SEM for tumor volume. FIG. 6B shows tumor burden shown as percent of tumor free mice after challenge with 4T1 cells s.c. Graph shows mean of 8 mice per treated group. FIG. 6C is a graph showing percentage of well/healthy mice based on visual inspection and observation. N=8 mice per group. FIG. 6D is a graph showing percentage of mice that survived.

FIGS. 7A-7D show mice were immunized thrice with each vaccine then injected with 50,000 4T1 cells i.v., tumors were allowed to grow for 25 days then mice were sacrificed. Results from the control Lm (FIG. 7A), LLO-Flk-E1 (FIG. 7B), and Lm-LLO-Flk-I1 (FIG. 7C) are shown. H+E stained sections were performed on lung tissues, tumor nodes were counted by hand. FIG. 7D shows the number of lung metastases per lobe per animal, Mean±SEM; *p<0.05, Mann-Whitney test, experiment repeated once, N=5 mice shown. FIG. 7F shows spleens from these animals were processed and re-challenged ex vivo in IFN-g ELISpot assays for Her-2/neu epitope spreading. The 4T1 cell line does express low levels of mouse Her-2/neu. Spreading is seen only in the Flk-1-E1 immunized mice. Graph shows Mean±SEM for spot number per well as compared to control Lm group; *p<0.05, Mann-Whitney test, experiment repeated once, N=5 per group. FIGS. 7E and 7G show a similar experiment where mice were protected via immunization with each vaccine for a series of three weeks then injected with 50,000 4T1-Luc cells i.v., mice were imaged longitudinally over the course of four weeks looking for the incidence of lung seeding and rate of metastasis. Average radiance in photons (p) captured per second (s) per $cm^2$ for the surface area (sr) gated in the ROI. Graph shows Mean±SEM; *p<0.05, Mann-Whitney test. Significance for mice as follows: Day 18, only Flk-E1 significant; Day 25, both Flk-E1 and Flk-I1 significantly different when compared to control Lm.

FIGS. 8A-8C show mice (n=5/group) were mated with syngeneic FVB/N males, gestation was confirmed upon the observance of a vaginal plug following coitus. This was considered as day 0.5 dpc. Total gestation length (FIG. 8A), pup mass at term (FIG. 8B), and total litter size was measured (FIG. 8C), graphs show Mean±SEM; *p<0.05. FIGS. 8B-8E show a pair of sterile skin biopsies were produced on the back of each vaccinated mouse (N=5/group). Healing was observed on a daily basis. FIG. 8D shows that on day 14 healing was complete for all groups tested, near identical healing was observed for all groups. FIG. 8E shows the number of days until wound closure, Mean±SEM; *p<0.05, Mann-Whitney test.

FIGS. 10A-10D. Flk-1 vaccines can significantly delay tumor outgrowth in spontaneous, orthotopic models for Her-2/neu breast cancer. Transgenic FVB-rHer-2/neu mice were immunized thrice with each Flk vaccine or control Lm alone. Tumors from each mouse were examined for mutated Her-2/neu message. Message RNA was collected, cDNA synthesized and sequenced. The resulting sequence was paired alongside the wild-type sequence to determine mutated residues. Only mutations that arose 4 times or more were considered true mutations. A summary of all mutations is found on the left of FIG. 10A, this shows an N of at least 3, but not more than 5 mice, per group. All mutational data is combined and overlayed onto the rat Her-2/neu wild-type sequence. The bold aa residues are mutations that arise when vaccines are against Her-2/neu domains (Singh, 2007). The red-highlighted aa residues are mutations that arise when Flk-1 vaccines are used. The blue-highlighted region shows the Her-2/neu kinase domain. The green-highlighted region shows the ATP-binding domain.

FIG. 11A. Anti-Her-2/neu human chimeric vaccine can delay the growth of a metastatic breast cancer line in the brain of protected mice. Balb/c mice were immunized thrice with each vaccine, either anti-human Her-2/neu or control vaccination NYESO1. EMT6-Luc cells (from John Ohlfest's lab at University of Minnesota) were grown in vitro then injected into the brain of anesthetized mice at 5,000 cell per mouse. EMT6-Luc cells express low levels of mouse Her-2/neu (data not shown) Cells were allowed to grow before being imaged on the indicated days. EMT6-Luc cells produce the enzyme luciferase and when they metabolize D-Luciferin in vivo the by-product are photons that are captured ex vivo using a Xenogen X-100 camera and displayed using a heat map. Pixel intensity is graphed as number of photons per second per cm^2 per cm of surface area, presented as average radiance.

FIG. 11B. Anti-HMWMAA human vaccine can delay the growth of a metastatic melanoma line in the brain of protected mice. C57Bl/6 mice were immunized thrice with each vaccine, either anti-human HMWMAA-C or control vaccination NYESO1. B16F10-Luc cells (from Jeff Miller's lab at UCSF) were grown in vitro then injected into the brain of anesthetized mice at 5,000 cells per mouse. B16F10 parental line do not express HMWMAA (personal communication), thus the only source of HMWMAA is on pericytes and glial cells. Luciferase mechanism and image capture the same as in FIG. 11A.

FIG. 12. Sequence of endoglin (CD105). The original fragment, based on the sequence cloned by Reisfeld's group, which was cloned into Lm-LLO-CD5 is in bold and underlined. Note that Rankpep and other MHC epitope predicting program have shown that there are several alternative, putative CTL epitopes (double underlined) for the b, d, and k H-2 haplotypes, that lie outside this region.

FIGS. 13A-13B show the design of the novel CD105A and CD105B-expressing *Listeria* constructs. FIG. 13A shows cloned regions for each construct are in bold and two putative epitopes are underlined; Lm-LLO-CD105A and Lm-LLOCD105B together span nearly the entire endoglin gene and encompass more potential CTL epitopes. FIG. 13B shows each underlined fragment was cloned into the expression vector pGG34 fused to adjuvant LLO.

FIG. 16A shows mice were vaccinated with $2 \times 10^8$ cfu of each vaccine (Lm-LLO-CD105A and B) on days 1, 8, and 15. FIG. 16B shows mice were vaccinated with $2 \times 10^8$ cfu of each vaccine (Lm-LLO-CD105A and B) on days 4, 11, and 18.

DETAILED DESCRIPTION OF THE PRESENT INVENTION

Figure 1A:
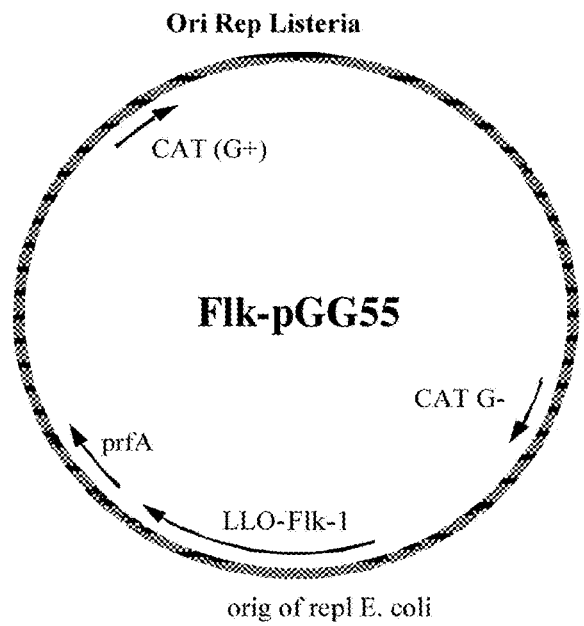

In one embodiment, the present invention provides recombinant *Listeria* strains comprising an angiogenic factor, recombinant polypeptides comprising an angiogenic factor operatively linked to a polypeptide comprising a aPEST-like sequence, recombinant nucleotide molecules encoding same, related vaccines, and immunogenic and therapeutic methods utilizing same.

In another embodiment, the present invention provides a recombinant *Listeria* strain expressing an angiogenic factor or an immunogenic fragment thereof.

In another embodiment, the present invention provides a recombinant *Listeria* strain comprising a nucleic acid encoding an angiogenic factor or an immunogenic fragment thereof.

In one embodiment, the present invention provides recombinant *Listeria* strains comprising vascular endothelial growth factor receptor-2 (VEGFR2) peptides, recombinant polypeptides comprising VEGFR2 operatively linked to a polypeptide comprising a PEST-like sequence, recombinant nucleotide molecules encoding same, related vaccines, and related immunogenic and therapeutic methods.

In another embodiment, the present invention provides a recombinant *Listeria* strain expressing a vascular endothelial growth factor receptor-2 (VEGFR2) polypeptide or an immunogenic fragment thereof.

In another embodiment, the present invention provides a recombinant *Listeria* strain expressing an endolin polypeptide or an immunogenic fragment thereof.

In another embodiment, the present invention provides a recombinant *Listeria* strain comprising a nucleic acid encoding a vascular endothelial growth factor receptor-2 (VEGFR2) polypeptide or an immunogenic fragment thereof.

In another embodiment, the present invention provides a recombinant *Listeria* strain comprising a nucleic acid encoding an endoglin polypeptide or an immunogenic fragment thereof.

In another embodiment, the present invention provides a recombinant *Listeria* strain comprising a recombinant nucleotide molecule of the present invention. In another embodiment, the present invention provides a recombinant *Listeria* strain comprising a recombinant polynucleotide of the present invention.

The recombinant *Listeria* strain of methods and compositions of the present invention is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. In one embodiment, the *Listeria* strain is a *Listeria* strain comprising LLO, while in another embodiment, the *Listeria* strain is a *Listeria* strain comprising ActA, while in another embodiment, the *Listeria* strain is a *Listeria* strain comprising PEST-like sequences.

In one embodiment, *Listeria monocytogenes* is a gram-positive facultative intracellular bacterium able to infect phagocytic cells and whose life cycle makes it a valuable delivery vehicle for foreign proteins. After phagocytosis, Lm escapes the phagosome via the hemolytic virulence factor LLO, encoded by the hly gene, to replicate in the cytoplasm. Lm may be engineered to express a gene of interest fused to the first 441 amino acids of LLO so as to exclude the hemolytic domain LLO contains a PEST domain that is important for the adjuvant activity in the fused proteins.

In another embodiment, the *Listeria* strain is attenuated by deletion of a gene. In another embodiment, the *Listeria* strain is attenuated by deletion of more than 1 gene. In another embodiment, the *Listeria* strain is attenuated by deletion or inactivation of a gene. In another embodiment, the *Listeria* strain is attenuated by deletion or inactivation of more than 1 gene.

In another embodiment, the gene that is mutated is hly. In another embodiment, the gene that is mutated is actA. In another embodiment, the gene that is mutated is plc A. In another embodiment, the gene that is mutated is plcB. In another embodiment, the gene that is mutated is mpl. In another embodiment, the gene that is mutated is inl A. In another embodiment, the gene that is mutated is inlB. In another embodiment, the gene that is mutated is bsh.

In another embodiment, the *Listeria* strain is an auxotrophic mutant. In another embodiment, the *Listeria* strain is deficient in a gene encoding a vitamin synthesis gene. In another embodiment, the *Listeria* strain is deficient in a gene encoding pantothenic acid synthase.

In another embodiment, the *Listeria* strain is deficient in an AA metabolism enzyme. In another embodiment, the *Listeria* strain is deficient in a D-glutamic acid synthase gene. In another embodiment, the *Listeria* strain is deficient in the dat gene. In another embodiment, the *Listeria* strain is deficient in the dal gene. In another embodiment, the *Listeria* strain is deficient in the dga gene. In another embodiment, the *Listeria* strain is deficient in a gene involved in the synthesis of diaminopimelic acid. CysK. In another embodiment, the gene is vitamin-B12 independent methionine synthase. In another embodiment, the gene is trpA. In another embodiment, the gene is trpB. In another embodiment, the gene is trpE. In another embodiment, the gene is asnB. In another embodiment, the gene is gltD. In another embodiment, the gene is gltB. In another embodiment, the gene is leuA. In another embodiment, the gene is argG. In another embodiment, the gene is thrC. In another embodiment, the *Listeria* strain is deficient in one or more of the genes described hereinabove.

In another embodiment, the *Listeria* strain is deficient in a synthase gene. In another embodiment, the gene is an AA synthesis gene. In another embodiment, the gene is folP. In another embodiment, the gene is dihydrouridine synthase family protein. In another embodiment, the gene is ispD. In another embodiment, the gene is ispF. In another embodiment, the gene is phosphoenolpyruvate synthase. In another embodiment, the gene is hisF. In another embodiment, the gene is hisH. In another embodiment, the gene is fliI. In another embodiment, the gene is ribosomal large subunit pseudouridine synthase. In another embodiment, the gene is ispD. In another embodiment, the gene is bifunctional GMP synthase/glutamine amidotransferase protein. In another embodiment, the gene is cobS. In another embodiment, the gene is cobB. In another embodiment, the gene is cbiD. In another embodiment, the gene is uroporphyrin-III C-methyltransferase/uroporphyrinogen-III synthase. In another embodiment, the gene is cobQ. In another embodiment, the gene is uppS. In another embodiment, the gene is truB. In another embodiment, the gene is dxs. In another embodiment, the gene is mvaS. In another embodiment, the gene is dapA. In another embodiment, the gene is ispG. In another embodiment, the gene is folC. In another embodiment, the gene is citrate synthase. In another embodiment, the gene is argJ. In another embodiment, the gene is 3-deoxy-7-phosphoheptulonate synthase. In another embodiment, the gene is indole-3-glycerol-phosphate synthase. In another embodiment, the gene is anthranilate synthase/glutamine amidotransferase component. In another embodiment, the gene is menB. In another embodiment, the gene is menaquinone-specific isochorismate synthase. In another embodiment, the gene is phosphoribosylformylglycinamidine synthase I or II. In another embodiment, the gene is phosphoribosylamin-oimidazole-succinocarboxamide synthase. In another embodiment, the gene is carB. In another embodiment, the gene is carA. In another embodiment, the gene is thyA. In another embodiment, the gene is mgsA. In another embodiment, the gene is aroB. In another embodiment, the gene is hepB. In another embodiment, the gene is rluB. In another embodiment, the gene is ilvB. In another embodiment, the gene is ilvN. In another embodiment, the gene is alsS. In another embodiment, the gene is fabF. In another embodiment, the gene is fabH. In another embodiment, the gene is pseudouridine synthase. In another embodiment, the gene is pyrG. In another embodiment, the gene is truA. In another embodiment, the gene is pabB. In another embodiment, the gene is an atp synthase gene (e.g. atpC, atpD-2, aptG, atpA-2, etc).

In another embodiment, the gene is phoP. In another embodiment, the gene is aroA. In another embodiment, the gene is aroC. In another embodiment, the gene is aroD. In another embodiment, the gene is plcB.

In another embodiment, the *Listeria* strain is deficient in a peptide transporter. In another embodiment, the gene is ABC transporter/ATP-binding/permease protein. In another embodiment, the gene is oligopeptide ABC transporter/oligopeptide-binding protein. In another embodiment, the gene is oligopeptide ABC transporter/permease protein. In another embodiment, the gene is zinc ABC transporter/zinc-binding protein. In another embodiment, the gene is sugar ABC transporter. In another embodiment, the gene is phosphate transporter. In another embodiment, the gene is ZIP zinc transporter. In another embodiment, the gene is drug resistance transporter of the EmrB/QacA family. In another embodiment, the gene is sulfate transporter. In another embodiment, the gene is proton-dependent oligopeptide transporter. In another embodiment, the gene is magnesium transporter. In another embodiment, the gene is formate/nitrite transporter. In another embodiment, the gene is spermidine/putrescine ABC transporter. In another embodiment, the gene is Na/Pi-cotransporter. In another embodiment, the gene is sugar phosphate transporter. In another embodiment, the gene is glutamine ABC transporter. In another embodiment, the gene is major facilitator family transporter. In another embodiment, the gene is glycine betaine/L-proline ABC transporter. In another embodiment, the gene is molybdenum ABC transporter. In another embodiment, the gene is techoic acid ABC transporter. In another embodiment, the gene is cobalt ABC transporter. In another embodiment, the gene is ammonium transporter. In another embodiment, the gene is amino acid ABC transporter. In another embodiment, the gene is cell division ABC transporter. In another embodiment, the gene is manganese ABC transporter. In another embodiment, the gene is iron compound ABC transporter. In another embodiment, the gene is maltose/maltodextrin ABC transporter. In another embodiment, the gene is drug resistance transporter of the Bcr/CflA family.

In another embodiment, the gene is a subunit of one of the above proteins.

In one embodiment, compositions of the present invention induce a strong innate stimulation of interferon-gamma, which in one embodiment, has anti-angiogenic properties. In one embodiment, a *Listeria* of the present invention induces a strong innate stimulation of interferon-gamma, which in one embodiment, has anti-angiogenic properties (Dominiecki et al., Cancer Immunol Immunother. 2005 May; 54(5):477-88. Epub 2004 Oct. 6, incorporated herein by reference in its entirety; Beatty and Paterson, J Immunol 2001 Feb. 15; 166(4):2276-82, incorporated herein by reference in its entirety). In one embodiment, anti-angiogenic properties of *Listeria* are mediated by CD4$^+$ T cells (Beatty and Paterson, 2001). In another embodiment, anti-angiogenic properties of *Listeria* are mediated by CD8$^+$ T cells. In another embodiment, IFN-gamma secretion as a result of *Listeria* vaccination is mediated by NK cells, NKT cells, Th1 CD4$^+$ T cells, TC1 CD8$^+$ T cells, or a combination thereof.

In another embodiment, compositions of the present invention induce production of one or more anti-angiogenic proteins or factors. In one embodiment, the anti-angiogenic protein is IFN-gamma. In another embodiment, the anti-angiogenic protein is pigment epithelium-derived factor (PEDF); angiostatin; endostatin; fms-like tyrosine kinase (sFlt)-1; or soluble endoglin (sEng). In one embodiment, a *Listeria* of the present invention is involved in the release of anti-angiogenic factors, and, therefore, in one embodiment, has a therapeutic role in addition to its role as a vector for introducing an antigen to a subject.

Each *Listeria* strain and type thereof represents a separate embodiment of the present invention.

In another embodiment, the recombinant *Listeria* of methods and compositions of the present invention is stably transformed with a construct encoding an antigen or an LLO-antigen fusion. In one embodiment, the construct contains a polylinker to facilitate further subcloning. Several techniques for producing recombinant *Listeria* are known; each technique represents a separate embodiment of the present invention.

In one embodiment, a construct useful in the compositions and methods of the present invention is expressed from the *Listeria* chromosome.

In another embodiment, the construct or heterologous gene is integrated into the Listerial chromosome using homologous recombination. Techniques for homologous recombination are well known in the art, and are described, for example, in Frankel, F R, Hegde, S, Lieberman, J, and Y Paterson. Induction of a cell-mediated immune response to HIV gag using *Listeria monocytogenes* as a live vaccine vector. J. Immunol. 155: 4766-4774. 1995; Mata, M, Yao, Z, Zubair, A, Syres, K and Y Paterson, Evaluation of a recombinant *Listeria monocytogenes* expressing an HIV protein that protects mice against viral challenge. Vaccine 19:1435-45, 2001; Boyer, J D, Robinson, T M, Maciag, P C, Peng, X, Johnson, R S, Pavlakis, G, Lewis, M G, Shen, A, Siliciano, R, Brown, C R, Weiner, D, and Y Paterson. DNA prime *Listeria* boost induces a cellular immune response to SIV antigens in the Rhesus Macaque model that is capable of limited suppression of SIV239 viral replication. Virology. 333: 88-101, 2005. In another embodiment, homologous recombination is performed as described in U.S. Pat. No. 6,855,320. In another embodiment, a temperature sensitive plasmid is used to select the recombinants. Each technique represents a separate embodiment of the present invention.

In another embodiment, the construct or heterologous gene is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed. In another embodiment, the position in the genome where the foreign gene has been inserted by transposon mutagenesis is unknown.

In another embodiment, the construct or heterologous gene is integrated into the Listerial chromosome using phage integration sites (Lauer P, Chow M Y et al, Construction, characterization, and use of two LM site-specific phage integration vectors. J Bacteriol 2002; 184(15): 4177-86). In another embodiment, an integrase gene and attachment site of a bacteriophage (e.g. U153 or PSA listeriophage) is used to insert the heterologous gene into the corresponding attachment site, which can be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. Each possibility represents a separate embodiment of the present invention.

In one embodiment, a composition of the present invention is expressed from an episomal vector in a *Listeria* strain. In another embodiment, the construct is carried by the *Listeria* strain on an episomal vector. In another embodiment, the construct is carried by the *Listeria* strain on a plasmid. LM vectors that express antigen fusion proteins have been constructed via this technique. Lm-GG/E7 was made by complementing a prfA-deletion mutant with a plasmid containing a copy of the prfA gene and a copy of the E7 gene fused to a form of the LLO (hly) gene truncated to eliminate the hemolytic activity of the enzyme, as described herein. Functional LLO was maintained by the organism via the endogenous chromosomal copy of hly. In another embodiment, the plasmid contains an antibiotic resistance gene. In another embodiment, the plasmid contains a gene encoding a virulence factor that is lacking in the genome of the transformed *Listeria* strain. In another embodiment, the virulence factor is prfA. In another embodiment, the virulence factor is LLO. In another embodiment, the virulence factor is ActA. In another embodiment, the virulence factor is any of the genes enumerated above as targets for attenuation. In another embodiment, the virulence factor is any other virulence factor known in the art. Each possibility represents a separate embodiment of the present invention.

In another embodiment, a recombinant peptide of the present invention is fused to a Listerial protein, such as PI-PLC, or a construct encoding same. In another embodiment, a signal sequence of a secreted Listerial protein such as hemolysin, ActA, or phospholipases is fused to the antigen-encoding gene. In another embodiment, a signal sequence of the recombinant vaccine vector is used. In another embodiment, a signal sequence functional in the recombinant vaccine vector is used. Each possibility represents a separate embodiment of the present invention.

In another embodiment, the construct is contained in the Listeria strain in an episomal fashion. In another embodiment, the foreign antigen is expressed from a vector harbored by the recombinant Listeria strain.

Each method of expression in Listeria represents a separate embodiment of the present invention.

In another embodiment, a recombinant Listeria strain of the present invention has been passaged through an animal host. In another embodiment, the passaging maximizes efficacy of the strain as a vaccine vector. In another embodiment, the passaging stabilizes the immunogenicity of the Listeria strain. In another embodiment, the passaging stabilizes the virulence of the Listeria strain. In another embodiment, the passaging increases the immunogenicity of the Listeria strain. In another embodiment, the passaging increases the virulence of the Listeria strain. In another embodiment, the passaging removes unstable sub-strains of the Listeria strain. In another embodiment, the passaging reduces the prevalence of unstable sub-strains of the Listeria strain. In another embodiment, the passaging attenuates the strain, or in another embodiment, makes the strain less virulent. In one embodiment, the animal through which the Listeria is passaged is a mammal, which, in one embodiment, is a mouse. The present invention contemplates the use of mammals such as mice, rabbits, guinea pigs, hamsters, gerbils, rats, and the like. Such mammals are well known in the art and are available to the skilled artisan through a variety of wholesalers, distributors, and laboratories, for example, Jackson Laboratories (Bar Harbor, Me.). Methods for passaging a recombinant Listeria strain through an animal host are known in the art, and are described, for example, in U.S. patent application Ser. No. 10/541,614. Each possibility represents a separate embodiment of the present invention.

In other related aspects, the invention includes an isolated nucleic acid encoding a truncated ActA, LLO, or PEST protein and an isolated nucleic acid encoding a VEGFR2 protein or immunogenic fragment thereof or an endoglin or immunogenic fragment thereof operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

In one embodiment, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In one embodiment, the present invention provides a vector comprising an oligonucleotide encoding a polypeptide of the present invention. In one embodiment, the term "oligonucleotide" refers to a short nucleic acid polymer, typically with twenty or fewer bases. In one embodiment, the present invention provides a vector comprising an polynucleotide encoding a polypeptide of the present invention. In one embodiment, the term "polynucleotide" refers to a chain of many nucleotides, which in one embodiment, is more than 5, in another embodiment, more than 10, in another embodiment, more than 20, in another embodiment, more than 50. In one embodiment, an oligonucleotide or polynucleotide or nucleic acid may refer to prokaryotic sequences, eukaryotic mRNA, cDNA from eukaryotic mRNA, genomic DNA sequences from eukaryotic (e.g., mammalian) DNA, or synthetic DNA sequences. The term also refers to sequences that include any of the known base analogs of DNA and RNA.

In one embodiment, two polynucleotides of the present invention are operably linked. For example, in one embodiment, polynucleotides encoding LLO and Flk1-E1, Flk1-E2, or Flk1-I1 are operably linked. In one embodiment, "operably linked" indicates that a single-stranded or double-stranded nucleic acid moiety comprises the two polynucleotides arranged within the nucleic acid moiety in such a manner that they are expressed together. By way of example, a promoter operably linked to the coding region of a gene is able to promote transcription of the coding region.

In one embodiment, a polynucleotide of the present invention comprises a promoter/regulatory sequence, which in one embodiment, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

In one embodiment, an isolated nucleic acid of the present invention is expressed under the control of a promoter, which in one embodiment, is an hly promoter, a prfA promoter, an ActA promoter, or a p60 promoter. In another embodiment, a polylpeptide of the present invention is expressed from a promoter, as described herein. In another embodiment, the promoter is CMV or CAG promoter. Other promoters that may be used are known in the art.

In one embodiment, the term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

In one embodiment, a "constitutive" promoter is a nucleotide sequence which, when operably linked with a polynucleotide which encodes or specifies a gene product, causes the gene product to be produced in a living human cell under most or all physiological conditions of the cell.

In one embodiment, an "inducible" promoter is a nucleotide sequence which, when operably linked with a polynucleotide which encodes or specifies a gene product, causes the gene product to be produced in a living cell substantially only when an inducer which corresponds to the promoter is present in the cell.

In one embodiment, a "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

In another embodiment, the present invention provides an isolated nucleic acid encoding a recombinant polypeptide of the present invention. In one embodiment, the isolated nucleic acid comprises a sequence sharing at least 85% homology with a nucleic acid encoding a recombinant polypeptide of the present invention. In another embodiment, the isolated nucleic acid comprises a sequence sharing at least 90% homology with a nucleic acid encoding a recombinant polypeptide of the present invention. In another embodiment, the isolated nucleic acid comprises a sequence sharing at least 95% homology with a nucleic acid encoding a recombinant polypeptide of the present invention. In another embodiment, the isolated nucleic acid comprises a sequence sharing at least 97% homology with a nucleic acid encoding a recombinant polypeptide of the present invention. In another embodiment, the isolated nucleic acid comprises a sequence sharing at least 99% homology with a nucleic acid encoding a recombinant polypeptide of the present invention.

The invention thus includes a vector comprising an isolated nucleic acid of the present invention. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the expression vector is a plasmid. Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York). Each possibility represents a separate embodiment of the present invention.

In another embodiment, the vector is an intracellular pathogen. In another embodiment, the vector is derived from a cytosolic pathogen. In another embodiment, the vector is derived from an intracellular pathogen. In another embodiment, an intracellular pathogen induces a predominantly cell-mediated immune response. In another embodiment, the vector is a *Salmonella* strain. In another embodiment, the vector is a BCG strain. In another embodiment, the vector is a bacterial vector. In another embodiment, dendritic cells transduced with a vector of the present invention may be administered to the subject to upregulate the subject's immune response, which in one embodiment is accomplished by upregulating CTL activity.

In another embodiment, the recombinant vaccine vector induces a predominantly Th1-type immune response.

In another embodiment, the vector is selected from *Salmonella* sp., *Shigella* sp., BCG, *L. monocytogenes*, *E. coli*, and *S. gordonii*. In another embodiment, the fusion proteins are delivered by recombinant bacterial vectors modified to escape phagolysosomal fusion and live in the cytoplasm of the cell. In another embodiment, the vector is a viral vector. In other embodiments, the vector is selected from Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. In another embodiment, the vector is a naked DNA vector. In another embodiment, the vector is any other vector known in the art. Each possibility represents a separate embodiment of the present invention.

In one embodiment, the present invention provides a *Listeria*, which in one embodiment, is a *Listeria* vaccine strain comprising an isolated nucleic acid or vector of the present invention. In one embodiment, a "*Listeria* vaccine strain" is used herein to refer to a recombinant *Listeria* organism that expresses a VEGFR2 or a portion thereof, or an endoglin or a portion thereof.

In another embodiment, the present invention provides a vaccine comprising a recombinant *Listeria* strain of the present invention and, optionally, an adjuvant. In another embodiment, the present invention provides a vaccine comprising a recombinant polypeptide of the present invention and, optionally, an adjuvant. In another embodiment, the present invention provides a vaccine comprising a recombinant oligonucleotide of the present invention and, optionally, an adjuvant.

In one embodiment, a vaccine of the present invention additionally comprises an adjuvant. In one embodiment, the vaccine additionally comprises a cytokine, chemokine, or combination thereof. In one embodiment, a vaccine is a composition which elicits an immune response to an antigen or polypeptide in the composition as a result of exposure to the composition. In another embodiment, the vaccine or composition additionally comprises APCs, which in one embodiment are autologous, while in another embodiment, they are allogeneic to the subject.

In one embodiment, a "vaccine" is a composition which elicits an immune response in a host to an antigen or polypeptide in the composition as a result of exposure to the composition. In one embodiment, the immune response is to a particular antigen or to a particular epitope on the antigen. In one embodiment, the vaccine may be a peptide vaccine, in another embodiment, a DNA vaccine. In another embodiment, the vaccine may be contained within and, in another embodiment, delivered by, a cell, which in one embodiment is a bacterial cell, which in one embodiment, is a *Listeria*. In one embodiment, a vaccine may prevent a subject from contracting or developing a disease or condition, wherein in another embodiment, a vaccine may be therapeutic to a subject having a disease or condition. Therapeutic and prophylactic effects of the compositions of the present invention are described hereinabove. In one embodiment, a vaccine of the present invention comprises a composition of the present invention and an adjuvant, cytokine, chemokine, or combination thereof.

In another embodiment, the present invention provides an immunogenic composition comprising a recombinant polypeptide of the present invention. In another embodiment, the immunogenic composition of methods and compositions of the present invention comprises a recombinant vaccine vector encoding a recombinant polypeptide of the present invention. In another embodiment, the immunogenic composition comprises a plasmid encoding a recombinant polypeptide of the present invention. In another embodiment, the immunogenic composition comprises an adjuvant. In one embodiment, a vector of the present invention may be administered as part of a vaccine composition. Each possibility represents a separate embodiment of the present invention.

The immunogenic composition utilized in methods and compositions of the present invention comprises, in another embodiment, a recombinant vaccine vector. In another embodiment, the recombinant vaccine vector comprises a plasmid encoding a recombinant polypeptide of the present invention. In another embodiment, the recombinant vaccine vector comprises an isolated nucleic acid of the present invention. In another embodiment, the recombinant vaccine vector comprises an isolated nucleic acid encoding a recombinant polypeptide of the present invention. Each possibility represents a separate embodiment of the present invention.

An immunogenic composition of methods and compositions of the present invention comprises, in another embodiment, an adjuvant that favors a predominantly Th1-type immune response. In another embodiment, the adjuvant favors a predominantly Th1-mediated immune response. In another embodiment, the adjuvant favors a Th1-type immune response. In another embodiment, the adjuvant favors a Th1-mediated immune response. In another embodiment, the adjuvant favors a cell-mediated immune response over an antibody-mediated response. In another embodiment, the adjuvant is any other type of adjuvant known in the art. In another embodiment, the immunogenic composition induces the formation of a T cell immune response against the target protein. Each possibility represents a separate embodiment of the present invention.

In another embodiment, the adjuvant is MPL. In another embodiment, the adjuvant is QS21. In another embodiment, the adjuvant is a TLR agonist. In another embodiment, the adjuvant is a TLR4 agonist. In another embodiment, the adjuvant is a TLR9 agonist. In another embodiment, the adjuvant is Resiquimod®. In another embodiment, the adjuvant is imiquimod. In another embodiment, the adjuvant is a CpG oligonucleotide. In another embodiment, the adjuvant is a cytokine or a nucleic acid encoding same. In another embodiment, the adjuvant is a chemokine or a nucleic acid encoding same. In another embodiment, the adjuvant is IL-12 or a nucleic acid encoding same. In another embodiment, the adjuvant is IL-6 or a nucleic acid encoding same. In another embodiment, the adjuvant is a lipopolysaccharide. In another embodiment, the adjuvant is as described in Fundamental Immunology, 5th ed (August 2003): William E Paul (Editor); Lippincott Williams & Wilkins Publishers; Chapter 43: Vaccines, GJV Nossal, which is hereby incorporated by reference. In another embodiment, the adjuvant is any other adjuvant known in the art. Each possibility represents a separate embodiment of the present invention.

In one embodiment, a "predominantly Th1-type immune response" refers to an immune response in which IFN-gamma is secreted. In another embodiment, it refers to an immune response in which tumor necrosis factor-0 is secreted. In another embodiment, it refers to an immune response in which IL-2 is secreted. Each possibility represents a separate embodiment of the present invention.

In another embodiment, the present invention provides a recombinant polypeptide comprising a VEGFR2 polypeptide or a fragment of a VEGFR2 polypeptide operatively linked to a non-VEGFR2 polypeptide selected from a non-hemolytic listeriolysin (LLO) polypeptide, an ActA polypeptide, or a PEST-like polypeptide or a fragment thereof. In one embodiment, the fragment has the same or a similar properties or function as the full length peptide or protein, as may be demonstrated using assays and tools known in the art. Properties and functions of full length peptides and proteins of the present invention are described in detail hereinbelow.

In another embodiment, the present invention provides a recombinant polypeptide comprising an endoglin or a fragment of an endoglin polypeptide operatively linked to a non-endoglin polypeptide selected from a non-hemolytic listeriolysin (LLO) polypeptide, an ActA polypeptide, or a PEST-like polypeptide or a fragment thereof. In one embodiment, the fragment has the same or a similar properties or function as the full length peptide or protein, as may be demonstrated using assays and tools known in the art. Properties and functions of full length peptides and proteins of the present invention are described in detail hereinbelow.

In one embodiment, the present invention provides a recombinant *Listeria* strain comprising a nucleic acid encoding an angiogenic factor or an immunogenic fragment thereof.

In one embodiment, the present invention provides a recombinant polypeptide comprising an angiogenic factor or an immunogenic fragment thereof, operatively linked to a polypeptide comprising a PEST-like sequence.

In one embodiment, the compositions of the present invention comprise an angiogenic factor, or an immunogenic fragment thereof, where in one embodiment, the immunogenic fragment comprises one or more epitopes recognized by the host immune system. In one embodiment, an angiogenic factor is a molecule involved in the formation of new blood vessels. In one embodiment, the angiogenic factor is VEGFR2. In another embodiment, the angiogenic factor is endoglin. In another embodiment, an angiogenic factor of the present invention is Angiogenin; Angiopoietin-1; Del-1; Fibroblast growth factors: acidic (aFGF) and basic (bFGF); Follistatin; Granulocyte colony-stimulating factor (G-CSF); Hepatocyte growth factor (HGF)/scatter factor (SF); Interleukin-8 (IL-8); Leptin; Midkine; Placental growth factor; Platelet-derived endothelial cell growth factor (PD-ECGF); Platelet-derived growth factor-BB (PDGF-BB); Pleiotrophin (PTN); Progranulin; Proliferin; Transforming growth factor-alpha (TGF-alpha); Transforming growth factor-beta (TGF-beta); Tumor necrosis factor-alpha (TNF-alpha); Vascular endothelial growth factor (VEGF)/vascular permeability factor (VPF). In another embodiment, an angiogenic factor is an angiogenic protein. In one embodiment, a growth factor is an angiogenic protein. In one embodiment, an angiogenic protein for use in the compositions and methods of the present invention is Fibroblast growth factors (FGF); VEGF; VEGFR and Neuropilin 1 (NRP-1); Angiopoietin 1 (Anga) and Tie2; Platelet-derived growth factor (PDGF; BB-homodimer) and PDGFR; Transforming growth factor-beta (TGF-β), endoglin and TGF-β receptors; monocyte chemotactic protein-1 (MCP-1); Integrins αVβ3, αVβ5 and α5β1; VE-cadherin and CD31; ephrin; plasminogen activators; plasminogen activator inhibitor-1; Nitric oxide synthase (NOS) and COX-2; AC133; or Id1/Id3. In one embodiment, an angiogenic protein for use in the compositions and methods of the present invention is an angiopoietin, which in one embodiment, is Angiopoietin 1, Angiopoietin 3, Angiopoietin 4 or Angiopoietin 6. In one embodiment, endoglin is also known as CD105; EDG; HHT1; ORW; or ORW1. In one embodiment, endoglin is a TGFbeta co-receptor.

In one embodiment, an angiogenic factor for use in the compositions and methods of the present invention excludes HMW-MAA. In another embodiment, an angiogenic factor for use in the compositions and methods of the present invention includes HMW-MAA. In one embodiment, HMW-MAA is also known as High molecular weight melanoma associated antigen (HMW-MAA); NG2; melanoma-associated chondroitin sulfate proteoglycan (MCSP); MCSPG; MSK16; HMW-MAA; MEL-CSPG; or chondroitin sulfate proteoglycan 4 (CSPG4). Other angiogenic factors are known in the art and may be used in the compositions and methods of the present invention.

Thus, in one embodiment, the compositions and methods of the present invention target tumor vasculature. In one embodiment, the compositions and methods of the present invention demonstrate profound epitope spreading, which in one embodiment, is a process whereby epitopes distinct from and non-cross-reactive with an inducing epitope become major targets of an ongoing immune response. In one embodiment, the data presented in the Examples hereinbelow demonstrate that a vaccine targeting the tumor vasculature may induce an immune response against endogenous tumor antigens, which in one embodiment, allows a skilled artisan to treat, suppress, or inhibit a tumor without targeting a specific tumor-associated antigen. Thus, in one embodiment, the compositions of the present invention serve as a universal vaccine against a cancer or tumor, which in one embodiment, is not dependent on a particular tumor antigen to be effective. In one embodiment, tumor specificity is conferred because tumors have poor vasculature and pericyte coverage.

In one embodiment, the compositions of the present invention are extremely effective in the methods of the present invention, in one embodiment, for protracted periods of time, because antigen loss variants are unlikely to occur, because angiogenic-related polypeptides such as VEGFR2/HMW-MAA/Endoglin are crucial for general functioning, and therefore will not be lost or replaced. In one embodiment, compositions and methods of the present invention will not harm normal tissue, which has well-developed vasculature and pericyte coverage, but will target tumor vasculature, whose vasculature and pericyte coverage is not well-developed.

In another embodiment, a particular fragment of an angiogenic factor is used in the compositions and methods of the present invention. In one embodiment, the fragment used in the compositions and methods of the present invention are based on analyzing the angiogenic factor amino acid sequence for regions that contain T cell epitopes, which in one embodiment, are determined by running the angiogenic factor sequence through an epitope predictor program, several of which are known in the art (for example, SYFPEITHI: http://www.syfpeithi.de/ or RANKpep: http://bio-.dfci.harvard.edu/RANKPEP/), and in another embodiment, are determined by predictive epitope mapping. In another embodiment, a hydrophobicity map, which in one embodiment, is Expasy: http://ca.expasy.org/, is used either alone or in conjunction with epitope prediction programs to identify a fragment of an angiogenic factor for use in the compositions and methods of the present invention. In another embodiment, the angiogenic factor fragment is identified by using human sequences that are homologous to angiogenic factor sequences in other species, in one embodiment, mice or rats, which are known to comprise T cell epitopes. In another embodiment, the angiogenic factor fragment used in the compositions and methods of the present invention are based on knowledge in the art regarding regions of angiogenic factor that contain T cell epitopes.

In one embodiment, an angiogenic factor for use in the compositions and methods of the present invention is VEGFR2.

In one embodiment, vascular endothelial growth factor (VEGF) is an important signaling protein involved in both vasculogenesis (the formation of the embryonic circulatory system) and angiogenesis (the growth of blood vessels from pre-existing vasculature). In one embodiment, VEGF activity is restricted mainly to cells of the vascular endothelium, although it does have effects on a limited number of other cell types (e.g. stimulation monocyte/macrophage migration). In vitro, VEGF has been shown to stimulate endothelial cell mitogenesis and cell migration. VEGF also enhances microvascular permeability and is sometimes referred to as vascular permeability factor.

In one embodiment, all of the members of the VEGF family stimulate cellular responses by binding to tyrosine kinase receptors (the VEGFRs) on the cell surface, causing them to dimerize and become activated through transphosphorylation. The VEGF receptors have an extracellular portion consisting of 7 immunoglobulin-like domains, a single transmembrane spanning region and an intracellular portion containing a split tyrosine-kinase domain.

In one embodiment, VEGF-A is a VEGFR-2 (KDR/Flk-1) ligand as well as a VEGFR-1 (Flt-1) ligand. In one embodiment, VEGFR-mediates almost all of the known cellular responses to VEGF. The function of VEGFR-1 is less well defined, although it is thought to modulate VEGFR-2 signaling, in one embodiment, via sequestration of VEGF from VEGFR-2 binding, which in one embodiment, is particularly important during vasculogenesis in the embryo. In one embodiment, VEGF-C and VEGF-D are ligands of the VEGFR-3 receptor, which in one embodiment, mediates lymphangiogenesis.

In one embodiment, the compositions of the present invention comprise a VEGF receptor or a fragment thereof, which in one embodiment, is a VEGFR-2 and, in another embodiment, a VEGFR-1, and, in another embodiment, VEGFR-3.

In one embodiment, vascular Endothelial Growth Factor Receptor 2 (VEGFR2) is highly expressed on activated endothelial cells (ECs) and participates in the formation of new blood vessels. In one embodiment, VEGFR2 binds all 5 isoforms of VEGF. In one embodiment, signaling of VEGF through VEGFR2 on ECs induces proliferation, migration, and eventual differentiation. In one embodiment, the mouse homologue of VEGFR2 is the fetal liver kinase gene-1 (Flk-1), which is a strong therapeutic target, and has important roles in tumor growth, invasion, and metastasis. In one embodiment, VEGFR2 is also referred to as kinase insert domain receptor (a type III receptor tyrosine kinase) (KDR), cluster of differentiation 309 (CD309), FLK1, Ly73, Krd-1, VEGFR, VEGFR-2, or 6130401C07.

In another embodiment, the VEGFR2 protein used in the compositions of the present invention has the following sequence:

MESKALLAVALWFCVETRAASVGLPGDFLHPPKLSTQKDILTILANTTLQ

ITCRGQRDLDWLWPNAQRDSEERVLVTECGGGDSIFCKTLTIPRVVGNDT

GAYKCSYRDVDIASTVYVYVRDYRSPFIASVSDQHGIVYITENKNKTVVI

PCRGSISNLNVSLCARYPEKRFVPDGNRISWDSEIGFTLPSYMISYAGMV

FCEAKINDETYQSIMYIVVVVGYRIYDVILSPPHEIELSAGEKLVLNCTA

RTELNVGLDFTWHSPPSKSHHKKIVNRDVKPFPGTVAKMFLSTLTIESVT

KSDQGEYTCVASSGRMIKRNRTFVRVHTKPFIAFGSGMKSLVEATVGSQV

RIPVKYLSYPAPDIKWYRNGRHESNYTMIVGDELTIMEVTERDAGNYTVI

LTNPISMEKQSHMVSLVVNVPPQIGEKALISPMDSYQYGTMQTLTCTVYA

NPPLHHIQWYWQLEEACSYRPGQTSPYACKEWRHVEDFQGGNKIEVTKNQ

YALIEGKNKTVSTLVIQAANVSALYKCEAINKAGRGERVISFHVIRGPEI

TVQPAAQPTEQESVSLLCTADRNTFENLTWYKLGSQATSVHMGESLTPVC

KNLDALWKLNGTMFSNSTNDILIVAFQNASLQDQGDYVCSAQDKKTKKRH

CLVKQLIILERMAPMITGNLENQTTTIGETIEVTCPASGNPTPHITWFKD

NETLVEDSGIVLRDGNRNLTIRRVRKEDGGLYTCQACNVLGCARAETLFI

IEGAQEKTNLEVIILVGTAVIAMFFWLLLVIVLRTVKRANEGELKTGYLS

IVMDPDELPLDERCERLPYDASKWEFPRDRLKLGKPLGRGAFGQVIEADA

FGIDKTATCKTVAVKMLKEGATHSEHRALMSELKILIHIGHHLNVVNLLG

ACTKPGGPLMVIVEFCKFGNLSTYLRGKRNEFVPYKSKGARFRQGKDYVG

ELSVDLKRRLDSITSSQSSASSGFVEEKSLSDVEEEEASEELYKDFLTLE

HLICYSFQVAKGMEFLASRKCHIRDLAARNILLSEKNVVKICDFGLARDI

YKDPDYVRKGDARLPLKWMAPETIFDRVYTIQSDVWSFGVLLWEIFSLGA

SPYPGVKIDEEFCRRLKEGTRMRAPDYTTPEMYQTMLDCWHEDPNQRPSF

SELVEHLGNLLQANAQQDGKDYIVLPMSETLSMEEDSGLSLPTSPVSCME

EEEVCDPKFHYDNTAGISHYLQNSKRKSRPVSVKTFEDIPLEEPEVKVIP

DDSQTDSGMVLASEELKTLEDRNKLSPSFGGMMPSKSRESVASEGSNQTS

GYQSGYHSDDTDTTVYSSDEAGLLKMVDAAVHADSGTTLRSPPV (GenBank Accession No. NP_034742.2, AAH20530.1, or EDL37891.1; SEQ ID NO: 4; the nucleic acid sequence is set forth in GenBank Accession No. NM_010612.2 or BC020530.1). In one embodiment, AA 68-277 corresponds to E1 described herein, AA 545-730 corresponds to E2 described herein, and AA 792-1081 corresponds to I1 described herein. In another embodiment, the above sequence is used as the source of the VEGFR2 fragment incorporated in a vaccine of the present invention. In another embodiment, a VEGFR2 AA sequence of methods and compositions of the present invention is a homologue of SEQ ID NO: 4. In another embodiment, the VEGFR2 AA sequence is a variant of SEQ ID NO: 4. In another embodiment, the VEGFR2 AA sequence is a fragment of SEQ ID NO: 4. In another embodiment, the VEGFR2 AA sequence is an isoform of SEQ ID NO: 4. Each possibility represents a separate embodiment of the present invention.

In another embodiment, the VEGFR2 has an amino acid sequence set forth in one of the following GenBank entries: EDL37891.1; CAA61917.1; BAC27532.1; BAE24892.1; AAH20530.1; AAB25043.1; CAA42040.1; or CAA50192.1. In another embodiment, the VEGFR2 has an amino acid sequence set forth in one of the following GenBank entries: EAX05462.1; EAX05463.1; EAX05464.1; CAA61916.1; BAD93138.1; AAB88005.1; AAC16450.1; BAG57114.1; AAI31823.1; ACF47599.1; AAA59459.1; or CAA43837.1. In another embodiment, the VEGFR2 has an amino acid sequence set forth in one of the following GenBank entries: EDL89914.1; EDL89915.1; EDL89916.1; AAH87029.1; AAB97508.1; or AAB97509.1. In another embodiment, the VEGFR2 has an amino acid sequence set forth in one of the following GenBank entries: CAQ13438.1; AAF03237.1; AAN47136.1; AAL16381.1; AAI29159.1; CAM73177.1; AAB18415.1; AAB41042.1; or AAB62405.1. In another embodiment, the VEGFR2 has any VEGFR2 amino acid sequence known in the art. In another embodiment, the VEGFR2 is a homologue of a sequence from one of the above GenBank entries. In another embodiment, the VEGFR2 is a variant of a sequence from one of the above GenBank entries. In another embodiment, the VEGFR2 is an isoform of a sequence from one of the above GenBank entries. In another embodiment, the VEGFR2 is a fragment of a sequence from one of the above GenBank entries. Each possibility represents a separate embodiment of the present invention.

In another embodiment, the VEGFR2 has a nucleic acid sequence set forth in one of the following GenBank entries: AC124615.11; AC134903.4; AC160723.2; AF061804.1;

AF153058.1; CH466524.1; X89777.1; AK031739.1; AK054510.1; AK141938.1; BCO20530.1; 553103.1; X59397.1; or X70842.1. In another embodiment, the VEGFR2 has a nucleic acid sequence set forth in one of the following GenBank entries: AC021220.7; AC111194.4; CH471057.1; EAX05463.1; EAX05464.1; X89776.1; AB209901.1; AF035121.1; AF063658.1; AK293668.1; BC131822.1; BP280621.1; CR606055.1; EU826563.1; L04947.1; or X61656.1. In another embodiment, the VEGFR2 has a nucleic acid sequence set forth in one of the following GenBank entries: CH473981.1; BC087029.1; U93306.1; or U93307.1. In another embodiment, the VEGFR2 has a nucleic acid sequence set forth in one of the following GenBank entries: AL935131.7; BX247946.6; CR759732.9; AF180354.1; AF487829.1; AY056466.1; BC129158.1; CU458916.1; U75995.1; U82383.1; U89515.1 In another embodiment, the VEGFR2 has any VEGFR2 nucleic acid sequence known in the art. In another embodiment, the VEGFR2 is a homologue of a sequence from one of the above GenBank entries. In another embodiment, the VEGFR2 is a variant of a sequence from one of the above GenBank entries. In another embodiment, the VEGFR2 is an isoform of a sequence from one of the above GenBank entries. In another embodiment, the VEGFR2 is a fragment of a sequence from one of the above GenBank entries. Each possibility represents a separate embodiment of the present invention.

In another embodiment, a VEGFR2 polypeptide fragment is utilized in compositions and methods of the present invention. In another embodiment, the VEGFR2 fragment comprises amino acids 68-277 of the VEGFR2 protein, which in one embodiment, is referred to as Flk1-E1. In another embodiment, the VEGFR2 polypeptide fragment has the sequence:

RDSEERVLVTECGGGDSIFCKTLTIPRVVGNDT-GAYKCSYRDVDIASTV YVYVRDYRSPFIASVSDQH-GIVYITENKNKTVVIPCRGSISNLNVSLCARYPEKRFV PDGNRISWDSEIGFTLPSYMISYAGMVFCEAKINDE-TYQSIMYIVVVVGYRIYDVIL SPPHEIELSAGEKLV-LNCTARTELNVGLDFTWHSPPSKSHHKKIVNR (SEQ ID NO: 5). In another embodiment, a VEGFR2 AA sequence of methods and compositions of the present invention comprises the sequence set forth in SEQ ID NO: 5. In another embodiment, the VEGFR2 AA sequence is a homologue of SEQ ID NO: 5. In another embodiment, the VEGFR2 AA sequence is a variant of SEQ ID NO: 5. In another embodiment, the VEGFR2 AA sequence is a fragment of SEQ ID NO: 5. In another embodiment, the VEGFR2 AA sequence is an isoform of SEQ ID NO: 5. Each possibility represents a separate embodiment of the present invention.

In another embodiment, the VEGFR2 fragment comprises amino acids 545-730 of the VEGFR2 protein, which in one embodiment, is referred to as Flk1-E2. In another embodiment, the VEGFR2 polypeptide fragment has the sequence:

VIRGPEITVQPAAQPTEQESVSLLCTADRNTFEN-LTWYKLGSQATSVHM GESLTPVCKNLDAL-WKLNGTMFSNSTNDILIVAFQNASLQDQGDYVC-SAQDKKTK KRHCLVKQLIILERMAPMITGNLENQTTTIGET-IEVTCPASGNPTPHTTWFKDNETL VEDSGIVLRDGN-RNLTIRRVRKEDG (SEQ ID NO: 6). In another embodiment, a VEGFR2 AA sequence of methods and compositions of the present invention comprises the sequence set forth in SEQ ID NO: 6. In another embodiment, the VEGFR2 AA sequence is a homologue of SEQ ID NO: 6. In another embodiment, the VEGFR2 AA sequence is a variant of SEQ ID NO: 6. In another embodiment, the VEGFR2 AA sequence is a fragment of SEQ ID NO: 6. In another embodiment, the VEGFR2 AA sequence is an isoform of SEQ ID NO: 6. Each possibility represents a separate embodiment of the present invention.

In another embodiment, the VEGFR2 fragment comprises amino acids 792-1081 of the VEGFR2 protein, which in one embodiment, is referred to as Flk1-I1. In another embodiment, the VEGFR2 polypeptide fragment has the sequence: EGELKTGYLSIVMDPDELPLDERCERLPYDASKWEF-PRDRLKLGKPLGR GAFGQVIEADAFGIDKTATCKT-VAVKMLKEGATHSEHRALMSELKILIHIGHHLNV VNLLGACTKPGGPLMVIVEFCKFGNLSTYLRG-KRNEFVPYKSKGARFRQGKDYVG ELSVDLKRRLD-SITSSQSSASSGFVEEKSLSDVEEEEASEELYKD-FLTLEHLICYSFQ VAKGMEFLASRKOHRDLAARNILLSEKNVVKICDF-GLARDIYKDPDYVRKGDARL PLKWMAPE-TIFDRVYT (SEQ ID NO: 7). In another embodiment, a VEGFR2 AA sequence of methods and compositions of the present invention comprises the sequence set forth in SEQ ID NO: 7. In another embodiment, the VEGFR2 AA sequence is a homologue of SEQ ID NO: 7. In another embodiment, the VEGFR2 AA sequence is a variant of SEQ ID NO: 7. In another embodiment, the VEGFR2 AA sequence is a fragment of SEQ ID NO: 7. In another embodiment, the VEGFR2 AA sequence is an isoform of SEQ ID NO: 7. Each possibility represents a separate embodiment of the present invention.

In another embodiment, the VEGFR2 fragment comprises amino acids 1082-1237 of the VEGFR2 protein, which in one embodiment, is referred to as Flk1-I2. In another embodiment, the VEGFR2 polypeptide fragment has the sequence:

IQSDVWSFGVLLWEIFSLGASPYPGVKIDEEFCR-RLKEGTRMRAPDYTTP EMYQTMLDCWHEDPN-QRPSFSELVEHLGNLLQANAQQDGKDYIVLPM-SETLSME EDSGLSLPTSPVSCMEEEEVCDPKFHYDNTAGISHY-LQNSKRKSRPVSVKTF (SEQ ID NO: 44). In another embodiment, a VEGFR2 AA sequence of methods and compositions of the present invention comprises the sequence set forth in SEQ ID NO: 44. In another embodiment, the VEGFR2 AA sequence is a homologue of SEQ ID NO: 44. In another embodiment, the VEGFR2 AA sequence is a variant of SEQ ID NO: 44. In another embodiment, the VEGFR2 AA sequence is a fragment of SEQ ID NO: 44. In another embodiment, the VEGFR2 AA sequence is an isoform of SEQ ID NO: 44. Each possibility represents a separate embodiment of the present invention.

In another embodiment, the VEGFR2 fragment used in the compositions and methods of the present invention are based on analyzing the VEGFR2 amino acid sequence for regions that contain T cell epitopes, which in one embodiment, are determined by running the VEGFR2 sequence through an epitope predictor program, several of which are known in the art, and in another embodiment, are determined by predictive epitope mapping. In another embodiment, the VEGFR2 fragment is used by using human sequences that are homologous to VEGFR2 sequences in other species, in one embodiment, mice or rats, which are known to comprise T cell epitopes. In another embodiment, the VEGFR2 fragment used in the compositions and methods of the present invention are based on knowledge in the art regarding regions of VEGFR2 that contain T cell epitopes.

In one embodiment, an endoglin protein is set forth in the following sequence:

MDRGVLPLPITLLLFEIYSFEPTTG-LAERVGCDLQPVDPTRGEVTFTTSQV SEGCVAQAA-NAVREVHVLFLDFPGMLSHLELTLQASKQNGTET-REVFLVLVSNKN VFVKFQAPEIPLHLAYDSSLVIFQGQPRVNITV-LPSLTSRKQILDWAATKGAITSIAA LDDPQSIVLQL-GQDPKAPFLCLPEAHKDMGATLEWQPRAQT-PVQSCRLEGVSGHK EAYILRILPGSEAGPRTVTVMMELSCTSGDAILILHG-PPYVSWHDINHSMQILTTGE YSVKIFPGSKVK-GVELPDTPQGLIAEARKLNASIVTSFVELPLVSNVSL-RASSCGGVF QTTPAPVVTTPPKDTCSPVLLMSLIQPKCGNQVMT-LALNKKHVQTLQCTITGLTFW DSSCQAEDTDDHLV-LSSAYSSCGMKVTAHVVSNEVIISFPSGSPLRKKVQ-CIDMD SLSFQLGLYLSPHFLQASNTIELGQQAFVQVSVSPLT-SEVTVQLDSCHLDLGPEGD MVELIQSRTAKG-SCVTLLSPSPEGDPRFSFLLRVYMVPTPTAGTLSCN-LALRPSTLS QEVYKTVSMRLNVVSPDLSGKGLVLPSVLGITFGA-FLIGALLTAALWYIYSHTRGP SKREPVVA-VAAPASSESSSTNHSIGSTQSTPCSTSSMA (SEQ ID NO: 55; FIG. 12). In one embodiment, the endoglin is any endoglin available in the art which include but is not limited to the following accession numbers: CAA54917.1, NP_001010968.1, NP_001074356.1, AAC63386.1, CAA50891. In another embodiment, aa 17-319 correspond to the construct CD105A. In another embodiment, aa 359-599 correspond to the construct CD105B.

In one embodiment, a human HLA-A0201 fragment for use in the compositions and methods of the present invention comprises amino acids 766-774 of the VEGFR2 protein. In another embodiment, the VEGFR2 polypeptide fragment comprises the sequence IILVGTAVI (SEQ ID NO: 47). In another embodiment, a human HLA-A0201 fragment for use in the compositions and methods of the present invention comprises amino acids 781-789 of the VEGFR2 protein. In another embodiment, the VEGFR2 polypeptide fragment comprises the sequence LLVIILRTV (SEQ ID NO: 48). In another embodiment, a human HLA-A0201 fragment for use in the compositions and methods of the present invention comprises amino acids 1034-1042 of the VEGFR2 protein. In another embodiment, the VEGFR2 polypeptide fragment comprises the sequence ILLSEKNVV (SEQ ID NO: 49). In another embodiment, a human HLA-A0201 fragment for use in the compositions and methods of the present invention comprises amino acids 1076-1084 of the VEGFR2 protein. In another embodiment, the VEGFR2 polypeptide fragment comprises the sequence TIFDRVYTI (SEQ ID NO: 50). In another embodiment, a human HLA-A0201 fragment for use in the compositions and methods of the present invention comprises amino acids 1093-1101 of the VEGFR2 protein. In another embodiment, the VEGFR2 polypeptide fragment comprises the sequence VLLWEIFSL (SEQ ID NO: 51).

In another embodiment, a VEGFR2 AA sequence of methods and compositions of the present invention consists of the sequence set forth in SEQ ID NOs: 47-51. In another embodiment, a VEGFR2 AA sequence of methods and compositions of the present invention comprises one or more of the sequence set forth in SEQ ID NOs: 47-51. In another embodiment, the VEGFR2 AA sequence is a homologue of SEQ ID NOs: 47-51. In another embodiment, the VEGFR2 AA sequence is a variant of SEQ ID NOs: 47-51. In another embodiment, the VEGFR2 AA sequence is a fragment of SEQ ID NOs: 47-51. In another embodiment, the VEGFR2 AA sequence is an isoform of SEQ ID NOs: 47-51. Each possibility represents a separate embodiment of the present invention.

Thus, in one embodiment, the VEGFR2 fragment used in the compositions and methods of the present invention is Flk1-E1, -E2, Flk1-H, or a combination thereof. In another embodiment, the VEGFR2 fragment used in the compositions and methods of the present invention is selected from SEQ ID NO: 5, SEQ ID NO: 6, or SEQ ID NO: 7.

In one embodiment, the VEGFR2 for the compositions and methods of the present invention comprise the VEGFR2 signal sequence, which in one embodiment, is amino acids 1-20 of the VEGFR2 amino acid sequence. In another embodiment, the VEGFR2 for the compositions and methods of the present invention excludes the VEGFR2 signal sequence.

In another embodiment, a recombinant polypeptide of the present invention further comprises a non-VEGFR2 peptide. In another embodiment, a recombinant polypeptide of the present invention is operatively linked to a polypeptide comprising a PEST-like sequence. In another embodiment, the non-VEGFR2 peptide enhances the immunogenicity of the fragment. Each possibility represents a separate embodiment of the present invention.

In one embodiment, the non-VEGFR2 polypeptide comprises a PEST-like sequence, while in another embodiment, the non-VEGFR2 polypeptide consists of a PEST-like sequence. The non-VEGFR2 polypeptide is, in another embodiment, a listeriolysin (LLO) oligopeptide, which in one embodiment, comprises a PEST-like sequence. In another embodiment, the non-VEGFR2 peptide is an ActA oligopeptide, which in one embodiment, comprises a PEST-like sequence. In another embodiment, the non-VEGFR2 peptide is a PEST-like oligopeptide. As provided herein, fusion to LLO, ActA, PEST-like sequences and fragments thereof enhances the cell-mediated immunogenicity of antigens. In one embodiment, fusion to LLO, ActA, PEST-like sequences and fragments thereof enhances the cell-mediated immunogenicity of antigens in a variety of expression systems. In one embodiment, the expression system is viral, while in another embodiment, the expression system is bacterial. In another embodiment, the non-VEGFR2 peptide is any other immunogenic non-VEGFR2 peptide known in the art. Each possibility represents a separate embodiment of the present invention.

In one embodiment, a polypeptide comprising a PEST-like sequence is a listeriolysin (LLO) peptide. In one embodiment, a polypeptide comprising a PEST-like sequence is a non-hemolytic listeriolysin (LLO) polypeptide. In one embodiment, a polypeptide comprising a PEST-like sequence is an ActA polypeptide. In one embodiment, a polypeptide comprising a PEST-like sequence is an N-terminal ActA polypeptide. In one embodiment, a polypeptide comprising a PEST-like sequence consists of a PEST-like sequence.

In one embodiment, an angiogenic factor for use in the compositions and methods of the present invention is HMW-MAA, which is described, in one embodiment, in U.S. patent application Ser. No. 11/889,715 filed 15 Aug. 2007 and U.S. patent application Ser. No. 12/244,828 filed 3 Oct. 2008, which are incorporated herein by reference in their entirety.

An LLO oligopeptide of methods and compositions of the present invention is, in another embodiment, a non-hemolytic LLO oligopeptide. In another embodiment, the oligopeptide is an LLO fragment. In another embodiment, the oligopeptide is a complete LLO protein. In another embodiment, the oligopeptide is any LLO protein or fragment thereof known in the art. Each possibility represents a separate embodiment of the present invention.

In one embodiment, the LLO protein is the major virulence factor of Lm responsible for the lysis of the phagolysosome. In one embodiment, LLO is highly immunogenic, in another embodiment, LLO induces maturation of antigen-specific T cells into Th1 cells, and in another embodiment, LLO induces interferon-gamma secretion by T cells.

In one embodiment, the LLO fragment comprises a mutation in the cholesterol binding domain or a deletion within the cholesterol binding domain, or a deletion of the cholesterol binding domain, which in one embodiment, renders the LLO non-hemolytic. In another embodiment, the LLO fragment is rendered non-hemolytic by chemical treatment. In another embodiment, the chemical treatment comprises glutaraldehyde. In another embodiment, the chemical treatment comprises a similarly acting compound. In another embodiment, the chemical treatment comprises any other suitable compound known in the art. Each possibility represents a separate embodiment of the present invention.

In another embodiment, the LLO protein utilized to construct vaccines of the present invention has the following sequence:

mkkimlvfitlilvslpiaqqteakdasafnkensissmappasppaspkt-piekkhadeidkyiqgldynknnvlv yhgdavtnvpprkgykdgneyiv-vekkkksinqnnadiqvvnaissltypgalvkanselvenqpdvpvkrdstlsi-dlpgmt nqdnkivvknatksnvnnavntlverwnekyaqaypnvsakidyddemay-sesqliakfgtafkavnnsnvnfgaisegkmq eevisfkqiyynvnvnep-trpsrffgkavtkeqlqalgvnaenppayissvaygrqvylklstnshstkv-kaafdaavsgksvsgdv eltniiknssfkaviyggsakdevqiidgnlgdlrdilkkgatfnretpgvpiay-ttnflkdnelaviknnseyiettskaytdgkinidhs ggyvaqfniswdevnyd-pegneivqhknwsennksklahftssiylpgnarninvyakectglawew-wrtviddrnlplvknrn isiwgttlypkysnkvdnpie (GenBank Accession No. P13128; SEQ ID NO: 8; the nucleic acid sequence is set forth in GenBank Accession No. X15127). In one embodiment, the first 25 AA of the proprotein corresponding to this sequence are the signal sequence and are cleaved from LLO when it is secreted by the bacterium. Thus, according to this embodiment, the full length active LLO protein is 504 residues long. In another embodiment, the above sequence is used as the source of the LLO fragment incorporated in a vaccine of the present invention. In another embodiment, an LLO AA sequence of methods and compositions of the present invention is a homologue of SEQ ID NO: 8. In another embodiment, the LLO AA sequence is a variant of SEQ ID NO: 8. In another embodiment, the LLO AA sequence is a fragment of SEQ ID NO: 8. In another embodiment, the LLO AA sequence is an isoform of SEQ ID NO: 8. Each possibility represents a separate embodiment of the present invention.

In another embodiment, an LLO protein fragment is utilized in compositions and methods of the present invention. In another embodiment, the LLO fragment is an N-terminal fragment. In another embodiment, the N-terminal LLO fragment has the sequence:

mkkimlvfitlilvslpiaqqteakdasafnkensissvappasppaspkt-piekkhadeidkyiqgldynknnvlv yhgdavtnvpprkgykdgneyiv-vekkkksinqnnadiqvvnaissltypgalvkanselvenqpdvpvkrdsltl-sidlpgmt nqdnkivvknatksnvnnavntlverwnekyaqaysnvsakidyddemay-sesqliakfgtafkavnnslnvnfgaisegkmq eevisfkqiyynvnvnep-trpsrffgkavtkeqlqalgvnaenppayissvaygrqvyllstnshstkvkaaf-daavsgksvsgdv eltniiknssfkaviyggsakdevqiidgnlgdlrdilkkgatfnretpgvpiay-ttnflkdnelaviknnseyiettskaytdgkinidhs ggyvaqfniswdevnyd (SEQ ID NO: 9). In another embodiment, an LLO AA sequence of methods and compositions of the present invention comprises the sequence set forth in SEQ ID NO: 9. In another embodiment, the LLO AA sequence is a homologue of SEQ ID NO: 9. In another embodiment, the LLO AA sequence is a variant of SEQ ID NO: 9. In another embodiment, the LLO AA sequence is a fragment of SEQ ID NO: 9. In another embodiment, the LLO AA sequence is an isoform of SEQ ID NO: 9. Each possibility represents a separate embodiment of the present invention.

In another embodiment, the LLO fragment has the sequence:

mkkimlvfitlilvslpiaqqteakdasafnkensissvappasppaspkt-piekkhadeidkyiqgldynknnvlv yhgdavtnvpprkgykdgneyiv-vekkkksinqnnadiqvvnaissltypgalvkanselvenqpdvpvkrdstlsi-dlpgmt nqdnkivvknatksnvnnavntlverwnekyaqaysnvsakidyddemay-sesqliakfgtafkavnnsnvnfgaisegkmq eevisfkqiyynvnvnep-trpsrffgkavtkeqlqalgvnaenppayissvaygrqvyllstnshstkvkaaf-daavsgksvsgdv eltniiknssfkaviyggsakdevqiidgnlgdlrdilkkgatfnretpgvpiay-ttnflkdnelaviknnseyiettskaytd (SEQ ID NO: 10). In another embodiment, an LLO AA sequence of methods and compositions of the present invention comprises the sequence set forth in SEQ ID NO: 10. In another embodiment, the LLO AA sequence is a homologue of SEQ ID NO: 10. In another embodiment, the LLO AA sequence is a variant of SEQ ID NO: 10. In another embodiment, the LLO AA sequence is a fragment of SEQ ID NO: 10. In another embodiment, the LLO AA sequence is an isoform of SEQ ID NO: 10. Each possibility represents a separate embodiment of the present invention.

In another embodiment, the LLO fragment of methods and compositions of the present invention comprises a PEST-like domain. In another embodiment, an LLO fragment that comprises a PEST sequence is utilized as part of a composition or in the methods of the present invention.

In another embodiment, the LLO fragment does not contain the activation domain at the carboxy terminus. In another embodiment, the LLO fragment does not include cysteine 484. In another embodiment, the LLO fragment is a non-hemolytic fragment. In another embodiment, the LLO fragment is rendered non-hemolytic by deletion or mutation of the activation domain. In another embodiment, the LLO fragment is rendered non-hemolytic by deletion or mutation of cysteine 484. In another embodiment, an LLO sequence is rendered non-hemolytic by deletion or mutation at another location.

In another embodiment, the LLO fragment consists of about the first 441 AA of the LLO protein. In another embodiment, the LLO fragment comprises about the first 400-441 AA of the 529 AA full length LLO protein. In another embodiment, the LLO fragment corresponds to AA 1-441 of an LLO protein disclosed herein. In another embodiment, the LLO fragment consists of about the first 420 AA of LLO. In another embodiment, the LLO fragment corresponds to AA 1-420 of an LLO protein disclosed herein. In another embodiment, the LLO fragment consists of about AA 20-442 of LLO. In another embodiment, the LLO fragment corresponds to AA 20-442 of an LLO protein disclosed herein. In another embodiment, any ALLO without the activation domain comprising cysteine 484, and in particular without cysteine 484, are suitable for methods and compositions of the present invention.

In another embodiment, the LLO fragment corresponds to the first 400 AA of an LLO protein. In another embodiment, the LLO fragment corresponds to the first 300 AA of an LLO protein. In another embodiment, the LLO fragment corresponds to the first 200 AA of an LLO protein. In another embodiment, the LLO fragment corresponds to the first 100 AA of an LLO protein. In another embodiment, the LLO fragment corresponds to the first 50 AA of an LLO protein, which in one embodiment, comprises one or more PEST-like sequences.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein.

Each LLO protein and LLO fragment represents a separate embodiment of the present invention.

In another embodiment, homologues of LLO from other species, including known lysins, such as streptolysin O, perfringolysin O, pneumolysin, etc, or fragments thereof may be used as the non-VEGFR2.

In another embodiment of methods and compositions of the present invention, a fragment of an ActA protein is fused to the VEGFR2 fragment. In another embodiment, the fragment of an ActA protein has the sequence:

MRAMMVVFITANCITINPDIIFAATDSEDSSLNT-DEWEEEKTEEQPSEVN TGPRY-ETAREVSSRDIKELEKSNKVRNTNKADLIAMLKEKA-EKGPNINNNNSEQTE NAAINEEASGADRPAIQVERRHPGLPSDSAAEIK-KRRKAIASSDSELESLTYPDKPTK VNKKKVAKESVA-DASESDLDSSMQSADESSPQPLKANQQPFFPKVFK-KIKDAGKW VRDKIDENPEVKKAIVDKSAGLIDQLLTKKKSEEVN-ASDFPPPPTDEELRLALPETP MLLGFNAPATSEPSS-FEFPPPPTDEELRLALPETPMLLGFNAPATSEPSSFEF-PPPPTE DELEIIRETASSLDSSFTRGDLASLRNAINRHSQNFSD-FPPIPTEEELNGRGGRP (SEQ ID NO: 11). In another embodiment, an ActA AA sequence of methods and compositions of the present invention comprises the sequence set forth in SEQ ID NO: 11. In another embodiment, the ActA AA sequence is a homologue of SEQ ID NO: 11. In another embodiment, the ActA AA sequence is a variant of SEQ ID NO: 11. In another embodiment, the ActA AA sequence is a fragment of SEQ ID NO: 11. In another embodiment, the ActA AA sequence is an isoform of SEQ ID NO: 11. Each possibility represents a separate embodiment of the present invention.

In another embodiment, the ActA fragment is encoded by a recombinant nucleotide comprising the sequence:

atgcgtgcgatgatggtggttttcattactgccaattgcattacgattaaccccga-cataatatttgcagcgacagata gcgaagattctagtctaaacacagat-gaatgggaagaagaaaaaacagaagagcaaccaagcgaggtaaatacgggac-caagat acgaaactgcacgtgaagtaagttcacgtgatattaaagaactagaaaaatc-gaataaagtgagaaatacgaacaaagcagaccta atagcaatgtt-gaaagaaaaagcagaaaaaggtccaaatatcaataataacaacagt-gaacaaactgagaatgcggctataaatgaa gaggcttcaggagccgaccgaccagctatacaagtggagcgtcgtcatccag-gattgccatcggatagcgcagcggaaattaaaa aagaaggaaagccatagcat-catcggatagtgagcttgaaagccttacttatccggataaaccaacaaaag-taaataagaaaaaa gtggcgaaagagtcagttgcggatgcttctgaaagtgacttagattctagcatgca-gtcagcagatgagtcttcaccacaaccttaa aagcaaaccaacaaccatttttc-cctaaagtatttaaaaaaataaaagatgcggggaaatgggtacgtgataaaatc-gacgaaaatcc tgaagtaaagaaagcgattgttgataaaagtgcagggttaattgaccaattattaac-caaaaagaaaagtgaagaggtaaatgcttcg gacttcccgccaccacctacg-gatgaagagttaagacttgctttgccagagacaccaatgcttcttggttttaatgctc-ctgctacatca gaaccgagctcattcgaatttccaccaccacctacggatgaagagttaagactt-gctttgccagagacgccaatgcttcttggttttaat gctcctgctacatcggaac-cgagctcgttcgaatttccaccgcctccaacagaagatgaactagaaatcatc-cgggaaacagcatcc tcgctagattctagttttacaagagggggatttagctagtttgagaaatgctat-taatcgccatagtcaaaatttctctgatttcccaccaat cccaacagaagaagagtt-gaacggagaggcggtagacca (SEQ ID NO: 12). In another embodiment, the recombinant nucleotide has the sequence set forth in SEQ ID NO: 12. In another embodiment, an ActA-encoding nucleotide of methods and compositions of the present invention comprises the sequence set forth in SEQ ID NO: 12. In another embodiment, the ActA-encoding nucleotide is a homologue of SEQ ID NO: 12. In another embodiment, the ActA-encoding nucleotide is a variant of SEQ ID NO: 12. In another embodiment, the ActA-encoding nucleotide is a fragment of SEQ ID NO: 12. In another embodiment, the ActA-encoding nucleotide is an isoform of SEQ ID NO: 12. Each possibility represents a separate embodiment of the present invention.

In another embodiment of methods and compositions of the present invention, a fragment of an ActA protein is fused to the VEGFR2 fragment. In another embodiment, the fragment of an ActA protein has the sequence as set forth in Genbank Accession No. AAF04762. In another embodiment, an ActA AA sequence of methods and compositions of the present invention comprises the sequence set forth in Genbank Accession No. AAF04762. In another embodiment, the ActA AA sequence is a homologue of Genbank Accession No. AAF04762. In another embodiment, the ActA AA sequence is a variant of Genbank Accession No. AAF04762. In another embodiment, the ActA AA sequence is a fragment of Genbank Accession No. AAF04762. In another embodiment, the ActA AA sequence is an isoform of Genbank Accession No. AAF04762. Each possibility represents a separate embodiment of the present invention.

In another embodiment, the ActA fragment is encoded by a recombinant nucleotide comprising the sequence as set forth in Genbank Accession No. AF103807. In another embodiment, the recombinant nucleotide has the sequence set forth in Genbank Accession No. AF103807. In another embodiment, an ActA-encoding nucleotide of methods and compositions of the present invention comprises the sequence set forth in Genbank Accession No. AF103807. In another embodiment, the ActA-encoding nucleotide is a homologue of Genbank Accession No. AF103807. In another embodiment, the ActA-encoding nucleotide is a variant of Genbank Accession No. AF103807. In another embodiment, the ActA-encoding nucleotide is a fragment of Genbank Accession No. AF103807. In another embodiment, the ActA-encoding nucleotide is an isoform of Genbank Accession No. AF103807. Each possibility represents a separate embodiment of the present invention.

In another embodiment, the ActA fragment is any other ActA fragment known in the art. In another embodiment, a recombinant nucleotide of the present invention comprises any other sequence that encodes a fragment of an ActA protein. In another embodiment, the recombinant nucleotide comprises any other sequence that encodes an entire ActA protein. Each possibility represents a separate embodiment of the present invention.

In another embodiment of methods and compositions of the present invention, a PEST-like AA sequence is fused to the VEGFR2 fragment. In another embodiment, the PEST-like AA sequence is KENSISSMAPPASPPASPKTPIEK-KHADEIDK (SEQ ID NO: 13). In another embodiment, the PEST-like sequence is KENSISSMAPPASPPASPK (SEQ ID NO: 14). In another embodiment, fusion of an antigen to any LLO sequence that includes one of the PEST-like AA sequences enumerated herein can enhance cell mediated immunity against VEGFR2.

In another embodiment, the PEST-like AA sequence is a PEST-like sequence from a *Listeria* ActA protein. In another embodiment, the PEST-like sequence is KTEEQPSEVNT-GPR (SEQ ID NO: 15), KASVTDT-SEGDLDSSMQSADESTPQPLK (SEQ ID NO: 16), KNEEVNASDFPPPPTDEELR (SEQ ID NO: 17), or RGGIPTSEEFSSLNSGDFTDDENSETTEEEIDR (SEQ ID NO: 18). In another embodiment, the PEST-like sequence is a variant of the PEST-like sequence described hereinabove, which in one embodiment, is KESVVDASES-DLDSSMQSADESTPQPLK (SEQ ID NO: 19), KSEEVN-ASDFPPPPTDEELR (SEQ ID NO: 20), or RGGRPTSEEF-SSLNSGDFTDDENSETTEEEIDR (SEQ ID NO: 21), as would be understood by a skilled artisan. In another embodiment, the PEST-like sequence is from *Listeria seeligeri* cytolysin, encoded by the lso gene. In another embodiment, the PEST-like sequence is RSEVTISPAETPESPPATP (SEQ ID NO: 22). In another embodiment, the PEST-like sequence is from Streptolysin O protein of *Streptococcus* sp. In another embodiment, the PEST-like sequence is from *Streptococcus pyogenes* Streptolysin O, e.g. KQN-TASTETTTTNEQPK (SEQ ID NO: 23) at AA 35-51. In another embodiment, the PEST-like sequence is from *Streptococcus equisimilis* Streptolysin O, e.g. KQNTAN-TETTTTNEQPK (SEQ ID NO: 24) at AA 38-54. In another embodiment, the PEST-like sequence is another PEST-like AA sequence derived from a protein from a prokaryotic organism, which in one embodiment is an ActA protein, and in another embodiment, is a cytolysin protein, which in one embodiment, is listeriolysin, and in another embodiment, is streptolysin.

Identification of PEST-like sequences is well known in the art, and is described, for example in Rogers S et al (Amino acid sequences common to rapidly degraded proteins: the PEST hypothesis. Science 1986; 234(4774):364-8) and Rechsteiner M et al (PEST sequences and regulation by proteolysis. Trends Biochem Sci 1996; 21(7):267-71). "PEST-like sequence" refers, in another embodiment, to a region rich in proline (P), glutamic acid (E), serine (S), and threonine (T) residues. In another embodiment, the PEST-like sequence is flanked by one or more clusters containing several positively charged amino acids. In another embodiment, the PEST-like sequence mediates rapid intracellular degradation of proteins containing it. In another embodiment, the PEST-like sequence fits an algorithm disclosed in Rogers et al. In another embodiment, the PEST-like sequence fits an algorithm disclosed in Rechsteiner et al. In another embodiment, the PEST-like sequence contains one or more internal phosphorylation sites, and phosphorylation at these sites precedes protein degradation.

In one embodiment, PEST-like sequences of prokaryotic organisms are identified in accordance with methods such as described by, for example Rechsteiner and Rogers (1996, Trends Biochem. Sci. 21:267-271) for LM and in Rogers S et al (Science 1986; 234(4774):364-8). Alternatively, PEST-like AA sequences from other prokaryotic organisms can also be identified based on this method. Other prokaryotic organisms wherein PEST-like AA sequences would be expected to include, but are not limited to, other *Listeria* species. In one embodiment, the PEST-like sequence fits an algorithm disclosed in Rogers et al. In another embodiment, the PEST-like sequence fits an algorithm disclosed in Rechsteiner et al. In another embodiment, the PEST-like sequence is identified using the PEST-find program.

In another embodiment, identification of PEST motifs is achieved by an initial scan for positively charged AA R, H, and K within the specified protein sequence. All AA between the positively charged flanks are counted and only those motifs are considered further, which contain a number of AA equal to or higher than the window-size parameter. In another embodiment, a PEST-like sequence must contain at least 1 P, 1 D or E, and at least 1 S or T.

In another embodiment, the quality of a PEST motif is refined by means of a scoring parameter based on the local enrichment of critical AA as well as the motifs hydrophobicity. Enrichment of D, E, P, S and T is expressed in mass percent (w/w) and corrected for 1 equivalent of D or E, 1 of P and 1 of S or T. In another embodiment, calculation of hydrophobicity follows in principle the method of J. Kyte and R. F. Doolittle (Kyte, J and Dootlittle, R F. J. Mol. Biol. 157, 105 (1982). For simplified calculations, Kyte-Doolittle hydropathy indices, which originally ranged from −4.5 for arginine to +4.5 for isoleucine, are converted to positive integers, using the following linear transformation, which yielded values from 0 for arginine to 90 for isoleucine.

$$\text{Hydropathy index}=10*\text{Kyte-Doolittle hydropathy index}+45$$

In another embodiment, a potential PEST motifs hydrophobicity is calculated as the sum over the products of mole percent and hydrophobicity index for each AA species.

The desired PEST score is obtained as combination of local enrichment term and hydrophobicity term as expressed by the following equation:

$$\text{PEST score}=0.55*\text{DEPST}-0.5*\text{hydrophobicity index}.$$

In another embodiment, "PEST sequence", "PEST-like sequence" or "PEST-like sequence peptide" refers to a peptide having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the present invention.

In another embodiment, the PEST-like sequence is identified using any other method or algorithm known in the art, e.g the CaSPredictor (Garay-Malpartida H M, Occhiucci J M, Alves J, Belizario J E. Bioinformatics. 2005 June; 21 Suppl 1:i169-76). In another embodiment, the following method is used:

A PEST index is calculated for each stretch of appropriate length (e.g. a 30-35 AA stretch) by assigning a value of 1 to the AA Ser, Thr, Pro, Glu, Asp, Asn, or Gin. The coefficient value (CV) for each of the PEST residue is 1 and for each of the other AA (non-PEST) is 0.

Each method for identifying a PEST-like sequence represents a separate embodiment of the present invention.

In another embodiment, the PEST-like sequence is any other PEST-like sequence known in the art. Each PEST-like sequence and type thereof represents a separate embodiment of the present invention.

"Fusion to a PEST-like sequence" refers, in another embodiment, to fusion to a protein fragment comprising a PEST-like sequence. In another embodiment, the term includes cases wherein the protein fragment comprises surrounding sequence other than the PEST-like sequence. In another embodiment, the protein fragment consists of the PEST-like sequence. Thus, in another embodiment, "fusion" refers to two peptides or protein fragments either linked together at their respective ends or embedded one within the other. Each possibility represents a separate embodiment of the present invention.

In one embodiment, the present invention provides a recombinant polypeptide comprising a vascular endothelial growth factor receptor-2 (VEGFR2) polypeptide or an immunogenic fragment thereof, operatively linked to a polypeptide comprising a PEST-like sequence.

In one embodiment, "protein" or "polypeptide" refers to an amino acid chain comprising multiple peptide subunits, and may, in one embodiment, include a full-length protein, oligopeptides, and fragments thereof, wherein the amino acid residues are linked by covalent peptide bonds. In one embodiment, a protein described in the present invention may comprise a polypeptide of the present invention. In one embodiment, a protein is a multimeric structure.

In one embodiment, a "recombinant" polypeptide refers to a polypeptide that is derived from recombinant DNA, which in one embodiment, is a form of synthetic DNA combining DNA sequences that would not normally occur together in nature. In one embodiment, a recombinant polypeptide may be referred to as a an engineered or a genetically engineered polypeptide.

The term "native" or "native sequence" refers to a polypeptide having the same amino acid sequence as a polypeptide that occurs in nature. A polypeptide is considered to be "native" in accordance with the present invention regardless of its mode of preparation. Thus, such native sequence polypeptide can be isolated from nature or can be produced by recombinant and/or synthetic means. The terms "native" and "native sequence" specifically encompass naturally-occurring truncated or secreted forms (e.g., an extracellular domain sequence), naturally-occurring variant forms (e.g., alternatively spliced forms) and naturally-occurring allelic variants of a polypeptide.

As used herein in the specification and in the examples section which follows the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Naturally occurring amino acids and non-conventional or modified amino acids which can be used with the present invention are well known in the art.

As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified wild type tumor suppressor protein. "Equivalent proteins" and "equivalent polypeptides" refer to compounds that depart from the linear sequence of the naturally occurring proteins or polypeptides, but which have amino acid substitutions that do not change it's biologically activity. These equivalents can differ from the native sequences by the replacement of one or more amino acids with related amino acids, for example, similarly charged amino acids, or the substitution or modification of side chains or functional groups.

The polypeptide of the present invention can be of any size. As can be expected, the polypeptides can exhibit a wide variety of molecular weights, some exceeding 150 to 200 kilodaltons (kD). Typically, the polypeptides may have a molecular weight ranging from about 5,000 to about 100,000 daltons. Still others may fall in a narrower range, for example, about 10,000 to about 75,000 daltons, or about 20,000 to about 50,000 daltons. In one embodiment, the polypeptides have a molecular weight between 19 and 51 kD. In one embodiment, a polypeptide of the present invention is 298 amino acids. In another embodiment, a polypeptide of the present invention is 396 amino acids. In another embodiment, a polypeptide of the present invention is 301 amino acids. In one embodiment, a polypeptide of the present invention is between 250 and 450 amino acid residues long. In another embodiment, a polypeptide of the present invention is between 200 and 500 amino acid residues long. In another embodiment, a polypeptide of the present invention is between 275 and 425 amino acid residues long. In another embodiment, a polypeptide of the present invention is between 100 and 600 amino acid residues long.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of 1 amino acid. In one embodiment, a variant may comprise an addition, deletion, substitution, or combination thereof of 2 amino acids. In one embodiment, a variant may comprise an addition, deletion or substitution, or combination thereof of 3 amino acids. In one embodiment, a variant may comprise an addition, deletion or substitution, or combination thereof of 4 amino acids. In one embodiment, a variant may comprise an addition, deletion or substitution, or combination thereof of 5 amino acids. In one embodiment, a variant may comprise an addition, deletion or substitution, or combination thereof of 7 amino acids. In one embodiment, a variant may comprise an addition, deletion or substitution, or combination thereof of 10 amino acids. In one embodiment, a variant may comprise an addition, deletion or substitution, or combination thereof of 2-15 amino acids. In one embodiment, a variant may comprise an addition, deletion or substitution, or combination thereof of 3-20 amino acids. In one embodiment, a variant may comprise an addition, deletion or substitution, or combination thereof of 4-25 amino acids.

Amino acid sequence variants may be used in the compositions and methods of the present invention. In one embodiment, amino acid sequence variants can be produced by expressing the underlying DNA sequence in a suitable recombinant host cell, or by in vitro synthesis of the desired polypeptide, as discussed above. The nucleic acid sequence encoding a polypeptide variant is, in one embodiment, prepared by site-directed mutagenesis of the nucleic acid sequence encoding the corresponding native (e.g. human) polypeptide. In another embodiment, site-directed mutagenesis using polymerase chain reaction (PCR) amplification (see, for example, U.S. Pat. No. 4,683,195 issued 28 Jul. 1987; and Current Protocols In Molecular Biology, Chapter 15 (Ausubel et al., ed., 1991) is used. Other site-directed mutagenesis techniques are also well known in the art and are described, for example, in the following publications: Current Protocols In Molecular Biology, supra, Chapter 8; Molecular Cloning: A Laboratory Manual., $2^{nd}$ edition (Sambrook et al., 1989); Zoller et al., Methods Enzymol. 100:468-500 (1983); Zoller & Smith, DNA 3:479-488 (1984); Zoller et al., Nucl. Acids Res., 10:6487 (1987); Brake et al., Proc. Natl. Acad. Sci. USA 81:4642-4646 (1984); Botstein et al., Science 229:1193 (1985); Kunkel et al., Methods Enzymol. 154:367-82 (1987), Adelman et al., DNA 2:183 (1983); and Carter et al., Nucl. Acids Res., 13:4331 (1986). Cassette mutagenesis (Wells et al., Gene 34:315 [1985]), and restriction selection mutagenesis (Wells et al., Philos. Trans. R. Soc. London SerA, 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The polypeptides of the invention can also be prepared by the combinatorial peptide library method disclosed, for example, in International Patent Publication PCT WO 92/09300. This method is particularly suitable for preparing and analyzing a plurality of molecules, that are variants of a given predetermined sequences, and is, therefore, particularly useful in identifying polypeptides with improved biological properties, which can then be produced by any technique known in the art, including recombinant DNA technology and/or chemical synthesis.

Methods for preparing peptide vaccines are well known in the art and are described, for example, in EP1408048, United States Patent Application Number 20070154953, and OGASAWARA et al (Proc. Nati. Acad. Sci. USA Vol. 89, pp. 8995-8999, October 1992). In one embodiment, peptide evolution techniques are used to create an antigen with higher immunogenicity. Techniques for peptide evolution are well known in the art and are described, for example in U.S. Pat. No. 6,773,900.

In another embodiment, fusion proteins of the present invention are prepared by a process comprising subcloning of appropriate sequences, followed by expression of the resulting nucleotide. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid. In another embodiment, a similar strategy is used to produce a protein wherein an VEGFR2 fragment is embedded within a heterologous peptide.

In another embodiment, a recombinant polypeptide of the methods and compositions of the present invention comprises a signal sequence. In another embodiment, the signal sequence is from the organism used to construct the vaccine vector. In another embodiment, the signal sequence is a LLO signal sequence. In another embodiment, the signal sequence is an ActA signal sequence. In another embodiment, the signal sequence is a Listerial signal sequence. In another embodiment, the signal sequence is any other signal sequence known in the art. Each possibility represents a separate embodiment of the present invention.

In another embodiment, the present invention provides a recombinant polypeptide of the present invention. In one embodiment, the recombinant polypeptide comprises a sequence sharing at least 85% homology with a recombinant polypeptide of the present invention. In another embodiment, the recombinant polypeptide comprises a sequence sharing at least 90% homology with a recombinant polypeptide of the present invention. In another embodiment, the recombinant polypeptide comprises a sequence sharing at least 95% homology with a recombinant polypeptide of the present invention. In another embodiment, the recombinant polypeptide comprises a sequence sharing at least 97% homology with a recombinant polypeptide of the present invention. In another embodiment, the recombinant polypeptide comprises a sequence sharing at least 99% homology with a recombinant polypeptide of the present invention.

In another embodiment, methods and compositions of the present invention utilize a chimeric molecule, comprising a fusion of a recombinant chimeric polypeptide with a tag polypeptide that provides an epitope to which an anti-tag antibody can selectively bind. The epitope tag is placed, in other embodiments, at the amino- or carboxyl-terminus of the protein or in an internal location therein. The presence of such epitope-tagged forms of the chimeric polypeptide is detected, in another embodiment, using an antibody against the tag polypeptide. In another embodiment, inclusion of the epitope tag enables the recombinant chimeric polypeptide to be readily purified by affinity purification using an anti-tag antibody or another type of affinity matrix that binds to the epitope tag. Various tag polypeptides and their respective antibodies are known in the art. Examples include polyhistidine (poly-his) or poly-histidine-glycine (poly-his-gly) tags; the flu HA tag polypeptide and its antibody 12CA5 (Field et al., Mol. Cell. Biol., 8: 2159-2165 (1988)); the c-myc tag and the 8F9, 3C7, 6E10, G4, B7 and 9E10 antibodies thereto (Evan et al., Molecular and Cellular Biology, 5: 3610-3616 (1985)); and the Herpes Simplex virus glycoprotein D (gD) tag and its antibody (Paborsky et al., Protein Engineering, 3(6): 547-553 (1990)). Other tag polypeptides include the Flag-peptide (Hopp et al., BioTechnology, 6: 1204-1210 (1988)); the KT3 epitope peptide (Martin et al., Science, 255: 192-194 (1992)); a tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87: 6393-6397 (1990)). Methods for constructing fusion proteins are well known in the art, and are described, for example, in LaRochelle et al., J. Cell Biol., 139(2): 357-66 (1995); Heidaran et al., FASEB J., 9(1): 140-5 (1995); Ashkenazi et al., Int. Rev. Immunol., 10(2-3): 219-27 (1993) and Cheon et al., PNAS USA, 91(3): 989-93 (1994).

In another embodiment, a peptide of the present invention is homologous to a peptide enumerated herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" or "homologous" refers to a sequence sharing greater than 70% identity with a second sequence. In another embodiment, "homology" refers to a sequence sharing greater than 72% identity with a second sequence. In another embodiment, "homology" refers to a sequence sharing greater than 75% identity with a second sequence. In another embodiment, "homology" refers to a sequence sharing greater than 78% identity with a second sequence. In another embodiment, "homology" refers to a sequence sharing greater than 80% identity with a second sequence. In another embodiment, "homology" refers to a sequence sharing greater than 82% identity with a second sequence. In another embodiment, "homology" refers to a sequence sharing greater than 83% identity with a second sequence. In another embodiment, "homology" refers to a sequence sharing greater than 85% identity with a second sequence. In another embodiment, "homology" refers to a sequence sharing greater than 87% identity with a second sequence. In another embodiment, "homology" refers to a sequence sharing greater than 88% identity with a second sequence. In another embodiment, "homology" refers to a sequence sharing greater than 90% identity with a second sequence. In another embodiment, "homology" refers to a sequence sharing greater than 92% identity with a second sequence. In another embodiment, "homology" refers to a sequence sharing greater than 93% identity with a second sequence. In another embodiment, "homology" refers to a sequence sharing greater than 95% identity with a second sequence. In another embodiment, "homology" refers to a sequence sharing greater than 96% identity with a second sequence. In another embodiment, "homology" refers to a sequence sharing greater than 97% identity with a second sequence. In another embodiment, "homology" refers to a sequence sharing greater than 98% identity with a second sequence. In another embodiment, "homology" refers to a sequence sharing greater than 99% identity with a second sequence. In another embodiment, "homology" refers to an identity of 100% identity with a second sequence. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis. Each method of determining homology represents a separate embodiment of the present invention.

In one embodiment, a "variant" is a peptide or protein that differs from another peptide or protein in a minor way, which in one embodiment, refers to a mutation in a region that does not affect the function of the peptide or protein, and in another embodiment, a conservative mutation that does not affect the function of the peptide or protein.

In one embodiment, "isoform" refers to a version of a molecule, for example, a protein, with only slight differences to another isoform of the same protein. In one embodiment, isoforms may be produced from different but related genes, or in another embodiment, may arise from the same gene by alternative splicing. In another embodiment, isoforms are caused by single nucleotide polymorphisms.

In one embodiment, a fragment of a polypeptide, which in one embodiment, is a Flk1 fragment, maintains its biological activity. In one embodiment, a fragment of a non-VEGFR2 polypeptide, for e.g., an ActA, LLO, or PEST-like sequence, maintains its ability to enhance the immunogenicity of the antigen or polypeptide to which it is fused. In another embodiment, a fragment of a non-VEGFR2 polypeptide, for e.g., an ActA, LLO, or PEST-like sequence, maintains its ability to lyse the host cell phagosome, or in another embodiment, to polymerize host actin, or, in another embodiment, serve as proteolytic signals.

In one embodiment, "immunogenic" refers to the ability of a substance (in one embodiment, an antigen) to induce an immune response.

In one embodiment, a "host cell" includes an individual cell or cell culture which can be or has been a recipient of any vector of the present invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a nucleic acid of the present invention.

In some embodiments, any of the polypeptides or nucleic acids of and for use in the methods of the present invention will comprise a VEGFR2 polypeptide or fragment, or an isolated nucleic acid encoded said a VEGFR2 polypeptide or fragment, in any form or embodiment as described herein. In some embodiments, any of the polypeptides or nucleic acids of and for use in the methods of the present invention will consist of a VEGFR2 polypeptide or fragment, or an isolated nucleic acid encoding said a VEGFR2 polypeptide or fragment of the present invention, in any form or embodiment as described herein. In some embodiments, the polypeptides or nucleic acids of this invention will consist essentially of a VEGFR2 polypeptide or fragment, or an isolated nucleic acid encoded said components of the present invention, in any form or embodiment as described herein. In some embodiments, the term "comprise" refers to the inclusion of other fragments, other antibodies, additional polypeptides, as well as inclusion of other proteins that may be known in the art. In some embodiments, the term "consisting essentially of" refers to a polypeptide or nucleic acid, which has the specific VEGFR2 polypeptide or fragment. However, other peptides may be included that are not involved directly in the utility of the toxin. In some embodiments, the term "consisting" refers to a toxin having the specific VEGFR2 polypeptide or fragment of the present invention, in any form or embodiment as described herein. Each of these is considered a separate embodiment of the present invention.

In another embodiment, the present invention provides a method of inducing an anti-VEGFR2 immune response in a subject, comprising administering to said subject a composition comprising a recombinant *Listeria* strain expressing a vascular endothelial growth factor receptor-2 (VEGFR2) polypeptide or an immunogenic fragment thereof.

In another embodiment, the present invention provides a method of treating a cancer in a subject, comprising the step of administering to said subject a composition comprising a recombinant *Listeria* strain expressing an angiogenic factor.

In another embodiment, the present invention provides a method of inhibiting or suppressing a cancer in a subject, comprising the step of administering to said subject a composition comprising a recombinant *Listeria* strain expressing an angiogenic factor.

In another embodiment, the present invention provides a method of preventing the recurrence of a tumor in a subject, comprising the step of administering to said subject a composition comprising a recombinant *Listeria* strain expressing an angiogenic factor. In one embodiment, the effectiveness of a recombinant *Listeria* strain expressing an angiogenic factor preventing the recurrence of a tumor is demonstrated in FIG. 4.

In another embodiment, the present invention provides a method of inhibiting metastasis of a tumor in a subject, comprising the step of administering to said subject a composition comprising a recombinant *Listeria* strain expressing an angiogenic factor.

In another embodiment, the present invention provides a method of treating a cancer in a subject, comprising the step of administering to said subject a composition comprising a recombinant polypeptide comprising an angiogenic factor operatively linked to a polypeptide comprising a PEST-like sequence.

In another embodiment, the present invention provides a method of inhibiting or suppressing a cancer in a subject, comprising the step of administering to said subject a composition comprising an angiogenic factor operatively linked to a polypeptide comprising a PEST-like sequence.

In another embodiment, the present invention provides a method of preventing the recurrence of a tumor in a subject, comprising the step of administering to said subject a composition comprising an angiogenic factor operatively linked to a polypeptide comprising a PEST-like sequence.

In another embodiment, the present invention provides a method of inhibiting metastasis of a tumor in a subject, comprising the step of administering to said subject a composition comprising an angiogenic factor operatively linked to a polypeptide comprising a PEST-like sequence.

In another embodiment, the present invention provides a method of treating a cancer in a subject, comprising the step of administering to said subject a composition comprising a nucleotide molecule encoding a recombinant polypeptide an angiogenic factor operatively linked to a polypeptide comprising a PEST-like sequence.

In another embodiment, the present invention provides a method of inhibiting or suppressing a cancer in a subject, comprising the step of administering to said subject a composition comprising a nucleotide molecule encoding an angiogenic factor operatively linked to a polypeptide comprising a PEST-like sequence.

In another embodiment, the present invention provides a method of preventing the recurrence of a tumor in a subject, comprising the step of administering to said subject a composition comprising a nucleotide molecule encoding an angiogenic factor operatively linked to a polypeptide comprising a PEST-like sequence.

In another embodiment, the present invention provides a method of inhibiting metastasis of a tumor in a subject, comprising the step of administering to said subject a composition comprising a nucleotide molecule encoding a recombinant polypeptide comprising an angiogenic factor operatively linked to a polypeptide comprising a PEST-like sequence.

In another embodiment, the present invention provides a method of treating a cancer in a subject, comprising the step of administering to said subject a composition comprising a recombinant *Listeria* strain expressing a vascular endothelial growth factor receptor-2 (VEGFR2) polypeptide or an immunogenic fragment thereof.

In another embodiment, the present invention provides a method of inhibiting or suppressing a cancer in a subject, comprising the step of administering to said subject a composition comprising a recombinant *Listeria* strain expressing a vascular endothelial growth factor receptor-2 (VEGFR2) polypeptide or an immunogenic fragment thereof.

In another embodiment, the present invention provides a method of preventing the recurrence of a tumor in a subject, comprising the step of administering to said subject a composition comprising a recombinant *Listeria* strain expressing a vascular endothelial growth factor receptor-2 (VEGFR2) polypeptide or an immunogenic fragment thereof.

In another embodiment, the present invention provides a method of inhibiting metastasis of a tumor in a subject, comprising the step of administering to said subject a composition comprising a recombinant *Listeria* strain expressing a vascular endothelial growth factor receptor-2 (VEGFR2) polypeptide or an immunogenic fragment thereof.

In another embodiment, the present invention provides a method of inducing an anti-VEGFR2 immune response in a subject, comprising administering to said subject an immunogenic composition comprising a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of treating a cancer in a subject, comprising the step of administering to said subject a composition comprising a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of inhibiting or suppressing a cancer in a subject, comprising the step of administering to said subject a composition comprising a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of preventing the recurrence of a tumor in a subject, comprising the step of administering to said subject a composition comprising a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of inhibiting metastasis of a tumor in a subject, comprising the step of administering to said subject a composition comprising a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of inducing an anti-VEGFR2 immune response in a subject, comprising administering to said subject an immunogenic composition comprising a nucleotide molecule encoding a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of treating a cancer in a subject, comprising the step of administering to said subject a composition comprising a nucleotide molecule encoding a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of inhibiting or suppressing a cancer in a subject, comprising the step of administering to said subject a composition comprising a nucleotide molecule encoding a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of preventing the recurrence of a tumor in a subject, comprising the step of administering to said subject a composition comprising a nucleotide molecule encoding a recombinant polypeptide comprising a vascular endothelial growth factor receptor-2 (VEGFR2) polypeptide or an immunogenic fragment thereof, operatively linked to a polypeptide comprising a PEST-like sequence.

In another embodiment, the present invention provides a method of inhibiting metastasis of a tumor in a subject, comprising the step of administering to said subject a composition comprising a nucleotide molecule encoding a recombinant polypeptide comprising a vascular endothelial growth factor receptor-2 (VEGFR2) polypeptide or an immunogenic fragment thereof, operatively linked to a polypeptide comprising a PEST-like sequence.

In one embodiment, the present invention provides a method of treating, inhibiting, or suppressing cancer or tumor metastasis comprising administering to a subject a composition of the present invention in which the subject mounts an immune response against the VEGFR2 polypeptide. In another embodiment, the subject mounts an immune response against a tumor antigen expressed by the tumor via epitope spreading.

In one embodiment, the compositions and methods of the present invention are for use in human subjects, while in another embodiment, they are for use in mammalian subjects. In one embodiment, the subject is an animal subject, which in one embodiment, is murine, bovine, canine, feline, equine, porcine, etc. In one embodiment, the term "mammal" or "mammalian" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. In one embodiment, the compositions and methods of the present invention are effective in male subjects. In another embodiment, the compositions and methods of the present invention are effective in female subjects.

In one embodiment, methods of the present invention are used to treat, impede, suppress, inhibit, or prevent any of the above-described diseases, disorders, symptoms, or side effects associated with allergy or asthma. In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, inducing regression, increasing efficacy of or decreasing resistance to alternative therapeutics, or a combination thereof. In one embodiment, "preventing" or "impeding" refers, inter alia, to delaying the onset of symptoms, preventing relapse to a disease, preventing recurrence of a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, the compositions and methods of the present invention completely eradicate an existing tumor, while in another embodiment, the compositions and methods of the present invention induce tumor regression, while in another embodiment, the compositions and methods of the present invention control tumor growth.

In one embodiment, symptoms are primary, while in another embodiment, symptoms are secondary. In one embodiment, "primary" refers to a symptom that is a direct result of a particular disease or disorder, while in one embodiment, "secondary" refers to a symptom that is derived from or consequent to a primary cause. In one embodiment, the compounds for use in the present invention treat primary or secondary symptoms or secondary complications related to cancer, which in one embodiment, is breast cancer. In another embodiment, "symptoms" may be any manifestation of a disease or pathological condition.

In one embodiment, the compositions and methods of the present invention are for inhibiting angiogenesis. In another embodiment, the compositions and methods of the present invention decrease microvascular density, which in one embodiment, is the microvascular density of a tumor.

In one embodiment, the compositions and methods of the present invention are for treating cancer. In one embodiment, the cancer is breast cancer. In another embodiment, the cancer is colorectal cancer, which in one embodiment, is metastatic colorectal cancer.

In one embodiment, the cancer is a Her-2/neu-expressing cancer.

In one embodiment, metastasis is a process by which cancer spreads from the place at which it first arose as a primary tumor to distant locations in the body. In one embodiment, a cancer of the present invention is a breast cancer metastasis. In another embodiment, a cancer of the present invention is a melanoma metastasis. In one embodiment, the cancer metastasizes to the brain. In another embodiment, the cancer metastasizes to the lung. In another embodiment, the cancer metastasizes to the kidney. In another embodiment, the cancer metastasizes to the colon. In another embodiment, the cancer, which in one embodiment, is a breast cancer, metastasizes to the breast or the area where the breast used to be, the chest wall, the lymph nodes, the bones, the lungs or around the lungs, the liver, the brain, or a combination thereof. In another embodiment, the cancer, which in one embodiment, is a melanoma, metastasizes to skin (other areas of the skin), subcutaneous tissue and lymph nodes, lungs and area between the lungs, liver, brain, bone, gastrointestinal tract, heart, pancreas, adrenal glands, kidneys, thyroid, or a combination thereof.

In one embodiment, other metastasizing cancers, as well as likely secondary organs in which the metastasized cancers will grow are known in the art.

In one embodiment, the compositions and methods of the present invention are for treating a tumor, which in one embodiment, is a solid tumor. In one embodiment, the tumor is a melanoma. In another embodiment, the tumor is a sarcoma. In another embodiment, the tumor is a carcinoma. In another embodiment, the tumor is a mesothelioma (e.g. malignant mesothelioma). In another embodiment, the tumor is a glioma. In another embodiment, the tumor is a germ cell tumor. In another embodiment, the tumor is a choriocarcinoma.

In another embodiment, the tumor is pancreatic cancer. In another embodiment, the tumor is ovarian cancer. In another embodiment, the tumor is gastric cancer. In another embodiment, the tumor is a carcinomatous lesion of the pancreas. In another embodiment, the tumor is pulmonary adenocarcinoma. In another embodiment, the tumor is colorectal adenocarcinoma. In another embodiment, the tumor is pulmonary squamous adenocarcinoma. In another embodiment, the tumor is gastric adenocarcinoma. In another embodiment, the tumor is an ovarian surface epithelial neoplasm (e.g. a benign, proliferative or malignant variety thereof). In another embodiment, the tumor is an oral squamous cell carcinoma. In another embodiment, the tumor is non small-cell lung carcinoma. In another embodiment, the tumor is an endometrial carcinoma. In another embodiment, the tumor is a bladder cancer. In another embodiment, the tumor is a head and neck cancer. In another embodiment, the tumor is a prostate carcinoma.

In another embodiment, the tumor is a non-small cell lung cancer (NSCLC). In another embodiment, the tumor is a Wilms' tumor. In another embodiment, the tumor is a desmoplastic small round cell tumor. In another embodiment, the tumor is a colon cancer. In another embodiment, the tumor is a lung cancer. In another embodiment, the tumor is an ovarian cancer. In another embodiment, the tumor is a uterine cancer. In another embodiment, the tumor is a thyroid cancer. In another embodiment, the tumor is a hepatocellular carcinoma. In another embodiment, the tumor is a thyroid cancer. In another embodiment, the tumor is a liver cancer. In another embodiment, the tumor is a renal cancer. In another embodiment, the tumor is a kaposis. In another embodiment, the tumor is a kaposis sarcoma. Each possibility represents a separate embodiment of the present invention.

In another embodiment, the tumor is a breast tumor. In one embodiment, the compositions and methods of the present invention are used to treat adenocarcinoma, which in one embodiment, develops in glandular tissue. In one embodiment, the compositions and methods of the present invention are used to treat ductal carcinoma in situ (DCIS), which in one embodiment, develops in the milk ducts and, in another embodiment, is an early form of breast cancer.

In another embodiment, the compositions and methods of the present invention are used to treat invasive ductal carcinoma (IDC), which in one embodiment, is the most common type of breast cancer, develops from DCIS, spreads through the duct walls, and invades the breast tissue. In another embodiment, the compositions and methods of the present invention are used to treat invasive lobular carcinoma, which in one embodiment, originates in the milk glands and accounts for 10-15% of invasive breast cancers. Additional types of breast cancer that may be treated using compositions and methods of the present invention include: Inflammatory (where, in one embodiment, breast tissue is warm and appears red; tends to spread quickly), Medullary carcinoma (which, in one embodiment, originates in central breast tissue), Mucinous carcinoma (where, in one embodiment, is invasive; usually occurs in postmenopausal women), Paget's disease of the nipple (which, in one embodiment, originates in the milk ducts and spreads to the skin of the nipples or areola), Phyllodes tumor (which, in one embodiment, is characterized by a tumor with a leaf-like appearance that extends into the ducts; rarely metastasizes), and Tubular carcinoma (which, in one embodiment, is a small tumor that is often undetectable by palpation). Compositions and methods of the present invention may also be used to treat sarcomas (in one embodiment, cancer of the connective tissue) and lymphomas (in one embodiment, cancer of the lymph tissue) that develop in breast tissue.

In another embodiment, the compositions and methods of the present invention are used to treat breast-related conditions in men, which in one embodiment, is Gynecomastia, Lobular breast cancer (LBC), and Infiltrating (or invasive) ductal carcinoma (IDC), which in one embodiment, is the most common form of male breast cancer and accounts for 80 to 90 percent of all men breast cancer diagnoses. In one embodiment, IDC originates in the duct and breaks into, or invades, the surrounding fatty tissue. In one embodiment, IDC may be contained only within the breast, or, in another embodiment, it can metasticize (spread) to other parts of the body.

In one embodiment, this invention provides compositions and methods for preventing cancer in populations that are predisposed to the cancer or in populations that are at high risk for the cancer, which in one embodiment, may be a population of women with brca1 or brca2 mutations, which population in one embodiment is susceptible to breast cancer.

In another embodiment, the immune response elicited by methods of the present invention is a cell-mediated immune response. In another embodiment, the immune response is a T-cell-mediated immune response. Each possibility represents a separate embodiment of the present invention.

The T cell-mediated immune response induced by methods and compositions of the present invention comprises, in another embodiment, a CTL. In another embodiment, the T cell involved in the T cell-mediated immune response is a CTL. Each possibility represents a separate embodiment of the present invention.

In another embodiment, the T cell-mediated immune response comprises a T helper cell. In another embodiment, the T cell involved in the T cell-mediated immune response is a T helper cell. Each possibility represents a separate embodiment of the present invention.

In one embodiment, a composition of the present invention leads to an infiltration of CD8+ T cells around blood vessels and in the stroma of tumors from immunized mice. In one embodiment, the presence of tumor infiltrating lymphocytes correlates with clinical responses in cancer immunotherapy. As described hereinbelow, despite their effect on vasculature, compositions of the present invention do not lead to toxicity such as wound healing, pregnancy or fertility problems associated with blood vessel damage in mice immunized with a vaccine of the present invention.

In one embodiment, the compositions of the present invention further comprise a tumor antigen. In one embodiment, the tumor antigen is High Molecular Weight Melanoma Associated Antigen (HMW-MAA). In one embodiment, the tumor antigen is an NY-ESO-1 protein. In another embodiment, the tumor antigen is a Human Papilloma Virus (HPV) E7 protein. In another embodiment, the tumor antigen is a B-cell receptor (BCR) protein. In another embodiment, the heterologous peptide of interest is an antigenic peptide. In another embodiment, the tumor antigen is an NY-ESO-1 peptide. In another embodiment, the tumor antigen is a Human Papilloma Virus (HPV) E7 peptide. In another embodiment, the tumor antigen is a B-cell receptor (BCR) peptide. In another embodiment, the tumor antigen is a Human Papilloma Virus (HPV)-16-E6, HPV-16-E7, HPV-18-E6, HPV-18-E7, a Her/2-neu antigen, a Prostate Specific Antigen (PSA), Prostate Stem Cell Antigen (PSCA), a Stratum Corneum Chymotryptic Enzyme (SCCE) antigen, Wilms tumor antigen 1 (WT-1), human telomerase reverse transcriptase (hTERT), Proteinase 3, Tyrosinase Related Protein 2 (TRP2), synovial sarcoma, X (SSX)-2, carcinoembryonic antigen (CEA), MAGE-A, interleukin-13 Receptor alpha (IL13-R alpha), Carbonic anhydrase IX (CAIX), survivin, GP100, or Testisin peptide. In another embodiment, the tumor antigen is alpha-fetoprotein, A3, antigen specific for A33 antibody, Ba 733, BrE3-antigen, CA125, CD1, CDIa, CD3, CD5, CD15, CD16, CD19, CD20, CD21, CD22, CD23, CD25, CD30, CD33, CD38, CD45, CD74, CD79a, CD80, CD1 38, colon-specific antigen-p (CSAp), CEA (CEACAM5), CEACAM6, CSAp, EGFR, EGP-I, EGP-2, Ep-CAM, FIt-I, Flt-3, folate receptor, HLA-DR, human chorionic gonadotropin (HCG) and its subunits, HER2/neu, hypoxia inducible factor (HIF-I), Ia, IL-2, IL-6, IL-8, insulin growth factor-1 (IGF-I), KC4-antigen, KS-I-antigen, KS 1-4, Le-Y, macrophage inhibition factor (MIF), MAGE, MUC1, MUC2, MUC3, MUC4, NCA66, NCA95, NCA90, antigen specific for PAM-4 antibody, placental growth factor, p53, prostatic acid phosphatase, PSMA, RS5, S100, TAC, TAG-72, tenascin, TRAIL receptors, Tn antigen, Thomson-Friedenreich antigens, tumor necrosis antigens, VEGF, ED-B fibronectin, 17-IA-antigen, an angiogenesis marker, an oncogene marker or an oncogene product. Other tumor antigens are described in Mizukami et al., (2005, Nature Med. 11:992-97); Hatfield et al., (2005, Curr.

Cancer Drug Targets 5:229-48); Vallbohmer et al. (2005, J. Clin. Oncol. 23:3536-44); and Ren et al. (2005, Ann. Surg. 242:55-63), which are each incorporated herein by reference in its entirety.

In one embodiment, the tumor antigen is High Molecular Weight Melanoma Associated Antigen (HMW-MAA), while in another embodiment, the tumor antigen is a fragment of HMW-MAA, as described in Maciag et al, Cancer Res. 2008 Oct. 1; 68(19):8066-75, which is incorporated herein by reference).

In one embodiment, compositions of the present invention comprise HMW-MAA or a fragment thereof, Her-2/neu or a fragment thereof, and Flk/VEGFR2, or a fragment thereof. In one embodiment, HMW-MAA targets pericytes, in one embodiment, Her-2/neu targets tumor cells, and in one embodiment, Flk/VEGFR2 targets endothelial cells.

In one embodiment, the tumor antigen is Her-2/neu, while in another embodiment, the tumor antigen is a Her-2/neu fragment.

In one embodiment, the VEGFR2 and the tumor antigen are expressed by the same vector, while in another embodiment, they are expressed by different vectors. In one embodiment, the VEGFR2 and the tumor antigen are expressed by the same *Listeria*, while in another embodiment, they are expressed by different *Listeria*.

In one embodiment, the tumor antigen is expressed as a fusion polylpeptide with a PEST-containing polypeptide, as described hereinabove. In one embodiment, the tumor antigen is operatively linked to a polypeptide comprising a PEST-like sequence, as described hereinabove. In one embodiment, the PEST-containing polypeptide is a non-hemolytic listeriolysin (LLO) polypeptide, an N-terminal ActA polypeptide, or a PEST sequence.

In one embodiment, the present invention provides a recombinant polypeptide made by a process comprising the step of translating a nucleotide molecule encoding said recombinant polypeptide.

In another embodiment, the present invention provides a recombinant polypeptide made by a process comprising the step of chemically conjugating a polypeptide comprising said VEGFR2 polypeptide to said polypeptide comprising said PEST-like sequence.

In one embodiment of methods of the present invention, the subject is administered an immunogenic composition, vector, or recombinant peptide of the present invention. In another embodiment of methods of the present invention, the subject is immunized with an immunogenic composition, vector, or recombinant peptide of the present invention. In another embodiment, the subject is contacted with the immunogenic composition, vector, or recombinant peptide. Each possibility represents a separate embodiment of the present invention.

In another embodiment, the present invention provides a kit comprising a compound or composition utilized in performing a method of the present invention. In another embodiment, the present invention provides a kit comprising a composition, tool, or instrument of the present invention. Each possibility represents a separate embodiment of the present invention.

Pharmaceutical Compositions and Methods of Administration

"Pharmaceutical composition" refers, in another embodiment, to a therapeutically effective amount of the active ingredient, i.e. the recombinant peptide or vector comprising or encoding same, together with a pharmaceutically acceptable carrier or diluent. A "therapeutically effective amount" refers, in another embodiment, to that amount which provides a therapeutic effect for a given condition and administration regimen.

The pharmaceutical compositions containing the active ingredient can be, in another embodiment, administered to a subject by any method known to a person skilled in the art, such as parenterally, transmucosally, transdermally, intramuscularly, intravenously, intra-dermally, subcutaneously, intra-peritonealy, intra-ventricularly, intra-cranially, intra-vaginally, or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the recombinant peptide or vector is prepared and applied as a solution, suspension, or emulsion in a physiologically acceptable diluent with or without a pharmaceutical carrier.

In another embodiment, the active ingredient is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In another embodiment, the pharmaceutical compositions provided herein are controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

In one embodiment, the secondary immune response to a tumor antigen, which in one embodiment, is Her-2/neu, is boosted. In one embodiment, this would provide additional protection from residing tumor cells, or tumor stem cells, as Her-2/neu is also highly expressed on these cell types. Thus, in one embodiment, contemplated as part of the present invention is a prime vaccination with a composition of the present invention and a boost with a vaccine comprising a tumor antigen related to the tumor being treated, such that the effect of epitope spreading from the first prime vaccination is enhanced by the boost.

In one embodiment, using immunotherapy to target the vasculature presents several advantages over the passive administration of purified antibodies, one being the ability to boost the initial immune response over time and the cost of vaccination. However, presented here, is the novel use of a recombinant fusion protein expressing *Listeria monocytogenes* vector, which presents several advantages over the use of other bacterial vectors. In one embodiment, Lm-LLO-Flk-1 strains have increased immunogenicity of the Flk-1 fragment via fusion to LLO, are highly attenuated and primarily replicate within macrophages and dendritic cells. Thus, in one embodiment, both the inflammatory response to infection with *Listeria* and the additional responses induced by our fusion protein constructs have the power to simultaneously reduce T regulatory cell numbers at the site of the tumor while inducing potent anti-tumor CTLs.

In one embodiment, metastatic breast cancer is especially susceptible to anti-angiogenesis treatment because metastases need to recruit new vessels when becoming established at distant locations from the primary tumor site. In one embodiment, micrometastases can exist in a growth static state at around 1-3 mm in diameter and feed from the passive movement of molecules. However, to support tumor growth beyond 3 mm, the new synthesis of a vascular network is required. Thus, in one embodiment, the anti-VEGFR2 vaccines of the present invention will be especially effective in blunting the spread of metastatic breast cancer once tumor growth is 3 mm or greater.

EXAMPLES

Materials and Methods

Mice.

Female FVB/N mice were purchased from Charles River Laboratories. The FVB/N Her-2/neu transgenic mice were housed and bred at the animal core facility at the University of Pennsylvania. Mice were six to eight weeks old at the start of the experiments, which were done in accordance with regulations by the Institutional Animal Care and Use Committee of the University of Pennsylvania.

Peptides and Antibodies.

Anti-mouse CD31, anti-mouse CD8α-PE, rat $IgG_{2a}$-PE isotype controls were purchased from BD Biosciences (San Jose, Calif.). Rabbit anti-*Listeria* antiserum polyclonal antibody, serotypes 1, 4 was purchased from Difco BD Biosciences. Rabbit anti-HIF-1a was purchased from Novus Biologicals (Littleton, Colo.). Goat anti-Rabbit-Alexa-488 secondary antibody was purchased from Invitrogen. DAPI was purchased from Sigma (St. Louis, Mo.). Rat anti-mouse IFN-g (clone AN18) was purchased from MABTECH (Mariemont, Ohio). Rat anti-mouse IFN-g (clone XMG1.2) was purchased from eBioscience (San Deigo, Calif.). The antibodies used in the Western blot for fusion protein expression was either a polyclonal rabbit serum raised to the first thirty residues (PEST) of LLO protein (Sewell et al., 2004, Cancer research. 64:8821-8825) or an anti-LLO mouse antibody, specific for full-length LLO, generated from hybridoma supernatant, clone #B5-19 (Edelson et al., 2001, Immunity. 14:503-512). All peptides were purchased from EZBiolabs (Westfield, Ind.). Tetramers were provided by Dr. Amy Stout of the National Institutes of Health AIDS Research and Reference Reagent Program. Tetramers used were all PE-conjugated $H-2D^q$ and contained either peptides for Her-2/neu region EC1 (ASPETHLDML; SEQ ID NO: 25), or EC2 (PDSLRDLSVF; SEQ ID NO: 26) or IC1 (GSGAFGTVYK; SEQ ID NO: 2). Peptides used in these studies were as follows: Flk-$E1_{210-219}$ (TYQSIMY1V; SEQ ID NO: 27), Flk-$E2_{613-622}$ (MFSNSTNDI; SEQ ID NO: 28), Flk-$I1_{906-915}$ (PGGPLMVIV; SEQ ID NO: 1), Flk-$I1_{839-848}$ (GRGAFGQVI; SEQ ID NO: 3); (Her2-pEC$1_{302-310}$ (PYNYLSTEV; SEQ ID NO: 29), Her2-pEC$2_{420-429}$ (PDSLRDLSVF; SEQ ID NO:263), Her2-pIC$1_{732-741}$ (GSGAFGTVYK; SEQ ID NO: 34); HIV-pGag (AMQMLKETI; SEQ ID NO: 30).

ELISpots

Secretion of IFN-g by mouse splenocytes in response to peptide stimulation was tested by enzyme-linked immunospot (ELISpot) assay. We preferred to use ELISpots over other assays because of the level of sensitivity that could be obtained for low frequency, antigen specific cells and also because we could test for anti-Her-2/neu and anti-Flk-1 specific T cells directly ex vivo without in vitro manipulation. Briefly, isolated splenocytes were plated at $1×10^6$ cells per well or titrated across a 96 well plate coated with 7 g/ml of rat anti-mouse IFN-γ antibody (clone AN18, MABTECH, Mariemont, Ohio), in the presence of 10 µg/ml peptide and 5 U/ml of IL-2. Secondary, biotinylated, anti-IFN-g antibody (clone XMG1.2, eBioscience) was added to each well at a final concentration of 2 µg/ml. After overnight incubation at 37° C. plates were developed for 1 hour at room temperature with Streptavidin-horseradish peroxidase (1:1000 dilution) followed by substrate TMB (Vector laboratories, ABC kit). Spots were counted using the Immunospot C.T.L. scanner and counting software (CTL, Cleveland, Ohio).

Cell Lines.

Cell culture media and supplements were purchased from Gibco (Invitrogen). NT-2 and J774A. 1 cells were maintained as previously described. All cell cultures were kept at 37° C. and 5% $CO_2$. 4T1 and 4T1 cells stably expressing the firefly luciferase gene (4T1-Luc) were the kind gift of Dr. Ellen Pure (Wistar Institute) and were maintained in cell culture medium.

Construction of Lm-LLO-Flk-1 Vaccines.

The source of the Flk-1 gene was a DNA vaccine plasmid generously provided by Dr. Ralph Reisfeld (The Scripps Research Institute, La Jolla, Calif.). Fragments corresponding to residues 68 to 1081 were amplified by PCR using the following primers: Flk-E1 (F): 5'-GGG CTCGAGCGTGATTCTGAGGAAAGGGTATT-3' (SEQ ID NO: 31), Flk-E1 (R): 5' GGG ACTAGTTTACCCGGTTTACAATCTTCTTAT-3' (SEQ ID NO: 32), (AA 68-277); Flk-E2 (F): 5'-GGG CTCGAGGTGATCAGGGGTCCTGAAATTA-3' (SEQ ID NO: 33), Flk-E2 (R): 5'-GGG ACTAGTTTAGCCTCCATCCTCCTTCCT-3' (SEQ ID NO: 34), (AA 545-730); Flk-I1 (F): 5'-GGG CTCGAGGAAGGGGAACTGAAGACAGCC-3' (SEQ ID NO: 35), Flk-I1 (R): 5'-GGG ACTAGTTTATGTGTATACTCTGTCAAAAATG GTTTC-3' (SEQ ID NO: 36), (AA 792-1081). XhoI sequence underlined for forward (F) primer, SpeI sequence underlined for reverse (R) primer, stop codon in bold. The PCR product was ligated into pCR2.1-TOPO plasmid (Invitrogen), confirmed by sequencing and subsequently excised by double digestion with XhoI and SpeI (New England Biolabs). The fragment was ligated into a pGG34-based plasmid downstream and fused to a gene encoding for the first 441 residues of the LLO protein, whose expression is driven by the hly promoter. The construction of the pGG34 plasmid has been described in detail elsewhere. The resultant plasmid was electroporated into the PrfA-defective Lm strain XFL-7, which is derived from the Lm strain 10403S. Positive clones were selected on Brain Heart Infusion (BHI, Difco) plates supplemented with 34 µg/ml of chloramphenicol and 250 µg/ml of streptomycin. The resultant stains were named Lm-LLO-Flk-E1, Lm-LLO-Flk-E2, and Lm-LLO-Flk-I1.

Growth and Preparation of Lm Vaccine Doses

Vaccine stocks were kept at −80° C. in 10% glycerol in 1×PBS. Each stock was streaked over a chloramphenicol/streptomycin plate and grown overnight. A single colony was used for growth in an overnight culture of 5 mls BHI media under antibiotic selection. This culture was further expanded for 4 hrs in a shaking incubator at 37° C. and grown until the microbial density reached 0.4-0.8 $OD_{600}$ at which time the microbes were washed and frozen sterile in 10% glycerol and kept at −80° C. until use. Stocks were titered for each lot generated. Single lots were used for one continuous experiment, different lots were used for each repetition, lot-to-lot variation was not observed. Each lot was checked for fusion protein expression by Western Blot with an anti-PEST and anti-LLO antibody. For each dose, one vial is selected, thawed and washed twice in 1×PBS before dilution and use; unused microbes are discarded.

Effect of Lm-LLO-Flk-1 Vaccines on Tumor Growth $1×10^6$ of NT-2 tumor cells were injected s.c. in 200 µl of PBS on the flank of FVB/N mice. On day 4 after tumor inoculation, mice were immunized i.p. with $5×10^8$ CFUs of either Lm-LLO-Flk-E1, Lm-LLO-Flk-E2 or Lm-LLO-Flk-I1. This dose was determined as one-tenth of the minimum dose observed to have adverse effects on the mice and was used in all experiments. Immunizations were repeated weekly totaling 3 doses of the vaccine for all experiments. In the control groups, mice received a control Lm vaccine—Lm-LLO-NY-ESO-$1_{101-156}$. Lm-LLO-NY-ESO-$1_{101-156}$ acts as an irrelevant or third party Lm vaccine to control for immune responses to LLO or the listerial infection, we commonly use this vaccine as a control at comparable concentrations to the test vaccine. Tumors were measured every 3 days with calipers and the shortest (width) and longest surface diameters were recorded for each individual tumor. Calculated tumor volumes were performed using the following equation: $[(width)^2×length×0.52]$. Mice were sacrificed if they developed open wounds or tumors reached 20 mm in diameter. Tumor-free surviving mice challenged with NT-2 were re-challenged in the opposite flank with the same cell line at least 10 weeks after the first inoculation.

Tumor Immunofluorescence

On day 64 post-tumor inoculation, mice were sacrificed and the NT-2 tumors were surgically excised, cryopreserved in OCT freezing medium and cryosectioned to provide 8-10 mm thick sections. For immunofluorescence, samples were thawed and fixed using 4% formalin. After blocking (2.4G2 conditioned medium/10% FBS/5% normal rat and mouse serum), sections were stained with primary antibodies in blocking solution in a humidified chamber at 37° C. for 1 hour. Samples were stained with secondary antibody following the same procedure as used for primary staining. DAPI (Invitrogen) staining was performed according to manufacturer's instructions. Intracellular staining for HIF-la was done in PBS/0.1% Tween/1% BSA solution. Slides were cover-slipped using mounting solution (Biomeda) with anti-fading agents, set for 24 hours and kept at 4° C. until imaged using Spot Image Software (vs. 2006) and a BX51 series Olympus fluorescent microscope. Images were merged using Spot Image Software and quantitation was performed after an ROI was gated using Image Pro Software (vs. 2006). All images are a merged series of three different channels captured for the same exposure time. For the quantitation of microvascular density using anti-CD31 we based our analysis on previously published works using similar strategies for measuring MVD in mouse tumor models (33-35).

Metastasis Studies and Bioluminescent Imaging

Mice were given a total of three vaccinations prior to i.v. injection, 7 days post-final vaccination, with 50,000 4T1 cells expressing the integrated luciferase reporter gene (4T1-Luc). The corresponding substrate, D-Luciferin was injected i.p. at 5-10 mg/mouse in 200 ul of PBS before imaging. The mice were placed in the dark chamber of a Xenogen IVIS imaging system (X-100) (Xenogen Corporation, Alameda, Calif.), under anesthesia following i.p. injection of ketamine (80 mg/kg)/xylazine (12 mg/kg) (Sigma, St. Louis, Mo.). Photographic and luminescence images were captured with a CCD camera and the luminescence intensity was quantitated using Living Image software (version 2.11) from Xenogen according to the manufacturer's instructions. Longitudinal imaging was performed on a weekly basis until at least 4 weeks post tumor inoculation. All mice were imaged for the same exposure and length of time. Images show normalized graphics. For the pathology study, the identical experiment was performed except lung tissue was perfused, extracted, wax embedded and stained with H+E before being counted (by hand) for tumors.

Pregnancy and Wound Healing Safety Studies.

Six to eight week old FVB/N female mice were immunized three consecutive times weekly with either a control Lm vaccine or Lm-LLO-Flk-1 vaccines. On the fourth week safety studies were conducted. For pregnancy and fertility, 5 mice per group were allowed to mate with individually housed males. Coitus was monitored and confirmed by the presence of a vaginal plug. Time to gestation, pup weight at birth and total litter size were measured. The wound-healing assay utilized in this study was done according to previously described methods. Briefly, mice were anesthetized, hair removed and skin-cleaned with an aseptic wipe. Two circular 3 mm in diameter wounds were punched from the skin using a sterile skin biopsy tool (Acuderm). Wounds were not treated and no infection was observed. Average time to wound closure was monitored and considered complete when a scar was formed without any visible scab left.
Statistical Analysis and Methods of Quantitation.

Data were analyzed using the non-parametric Mann-Whitney test. The log-rank chi-squared test was used for all survival data. All statistical analysis was done with Prism software, vs. 4.0a (2006). Statistical significance was based on a value of $p<0.05$. In all non-transgenic studies we included at least 8 mice per group. All studies were repeated at least once.

Example 1

Construction of LLO-Flk-1 Constructs

Figure 2B:
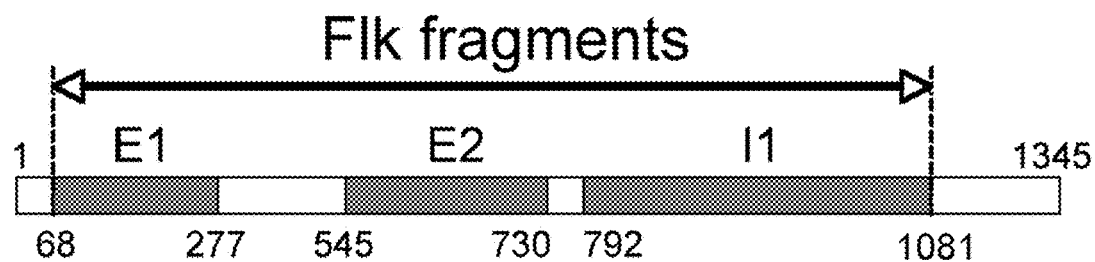
Figure 2C:
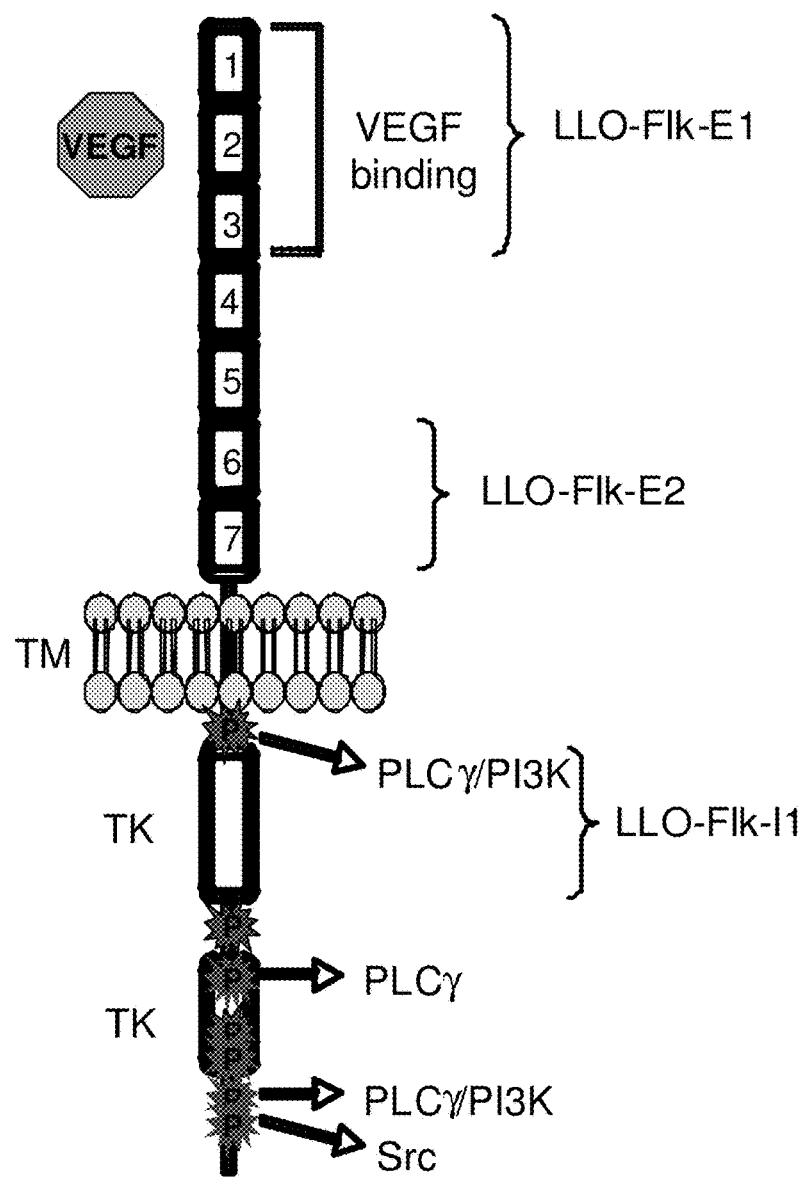
Figure 2D:
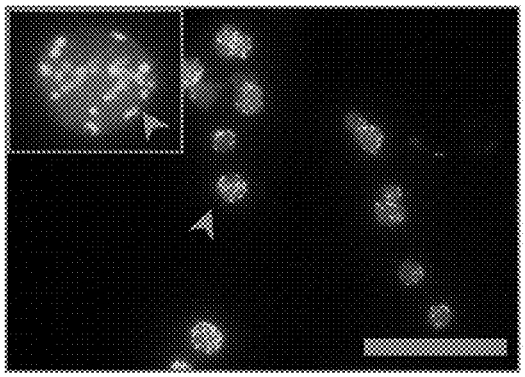
Figure 2E:
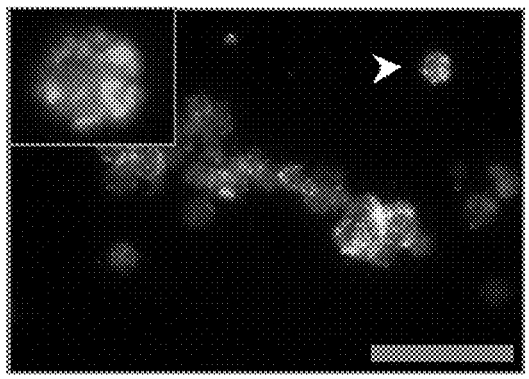
Figure 2F:
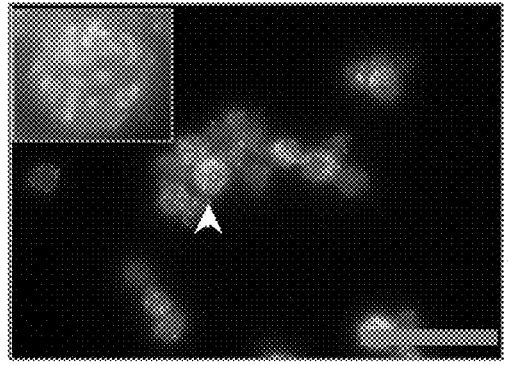
Figure 2G:
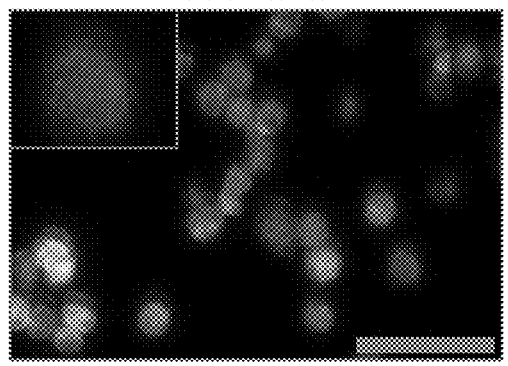
Figure 2H:
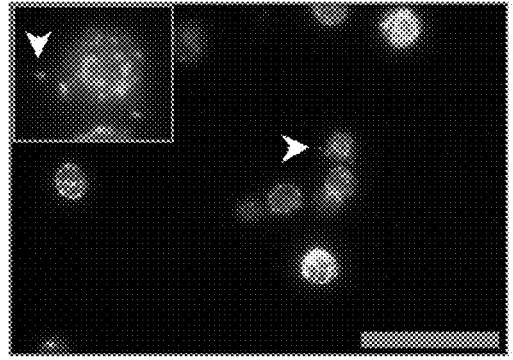

A total of three constructs were tested, each containing a different region of Flk-1: E1 (AA 68-277), E2 (AA 545-730) and I1 (792-1081) (FIG. 1A). Regions were selected based on predicted epitopes. Since we were interested in testing these vaccines in the FVB/N-based breast cancer model, we decided to clone fragments that would be most appropriate for the model haplotype used for testing (i.e., FVB/N, $H2^q$). The E1, E2 and I1 domains selected contained several potential epitopes for the $H-2^q$ mouse MHC I haplotype (FIG. 2A).

Figure 1B:
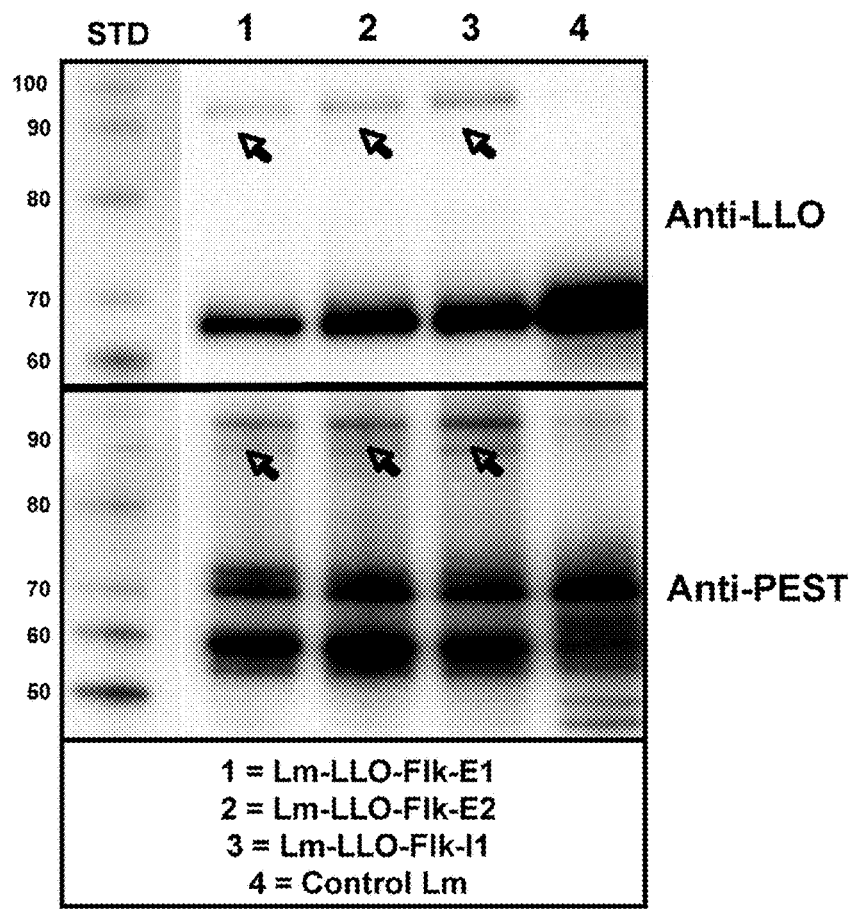

Each fragment was cloned as a fusion protein with the truncated LLO protein (FIG. 1A). To test whether the LLO-Flk-1 fusion proteins were produced and secreted by the Lm-LLO-Flk-1 constructs, we analyzed protein from culture supernatants by Western-Blot (FIG. 1B) using a polyclonal anti-PEST antibody (FIG. 1B bottom) or anti-LLO antibody (FIG. 1B top). A band for each fusion construct was detected, LLO-Flk-E1 (~81 kDa), LLO-Flk-E2 (~78 kDa), and LLO-Flk-I1 (~89 kDa). The band around 60-70 kDa is endogenous LLO; the truncated fusion protein LLO is found around 60-50 kDa. The anti-LLO blot was used as a control to show that our fusion proteins are LLO-Flk linked. All three constructs were able to infect, grow, and escape the phagolysosome as evidenced by replication in J774A.1 macrophages (FIGS. 2D-2H). Also, each vaccine was able to immunize mice against cloned Flk-1 regions as shown by IFN-g splenocyte responses ex vivo (FIG. 1C). Peptides used for re-challenge in these FVB/N ELISpot experiments were originally mapped in the $H2^d$ Balb/c mouse as immunodominant Flk-1 epitopes. We routinely use $H2^d$ mapped epitopes in $H2^q$ models as $H2^d$ identified epitopes can also serve as $H2^q$ epitopes presumably due to the high homology of the $H2^d$ and $H2^q$ molecules.

Example 2

Figure 3A:
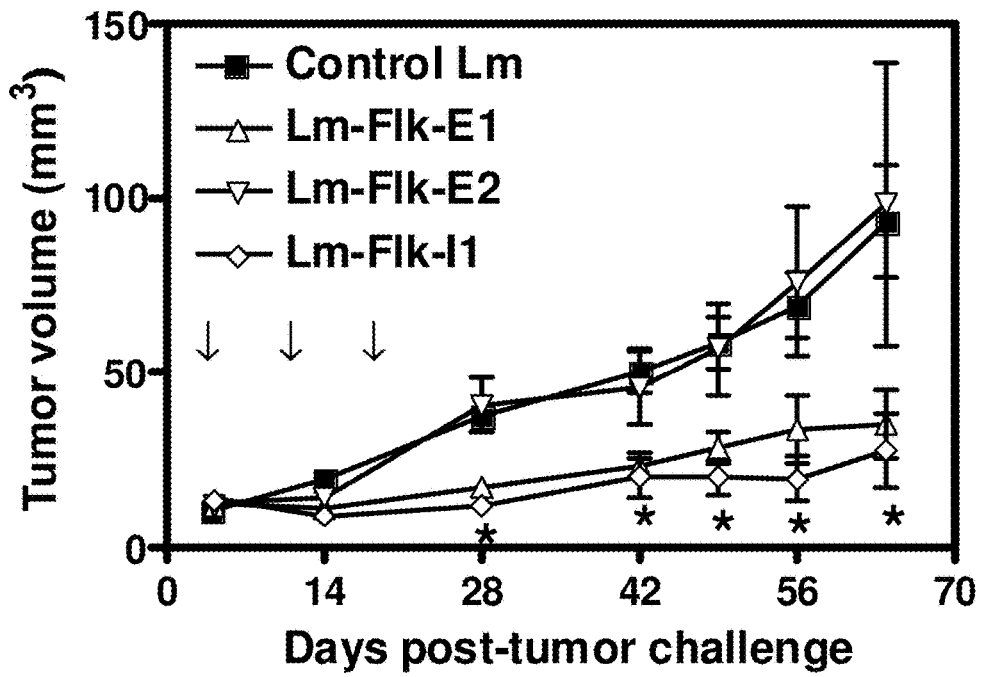
FIGS. 3A-3J show Lm-LLO-Flk-1 vaccines can induce regression of established Her-2/neu+ tumors in vivo.
Figure 4A:
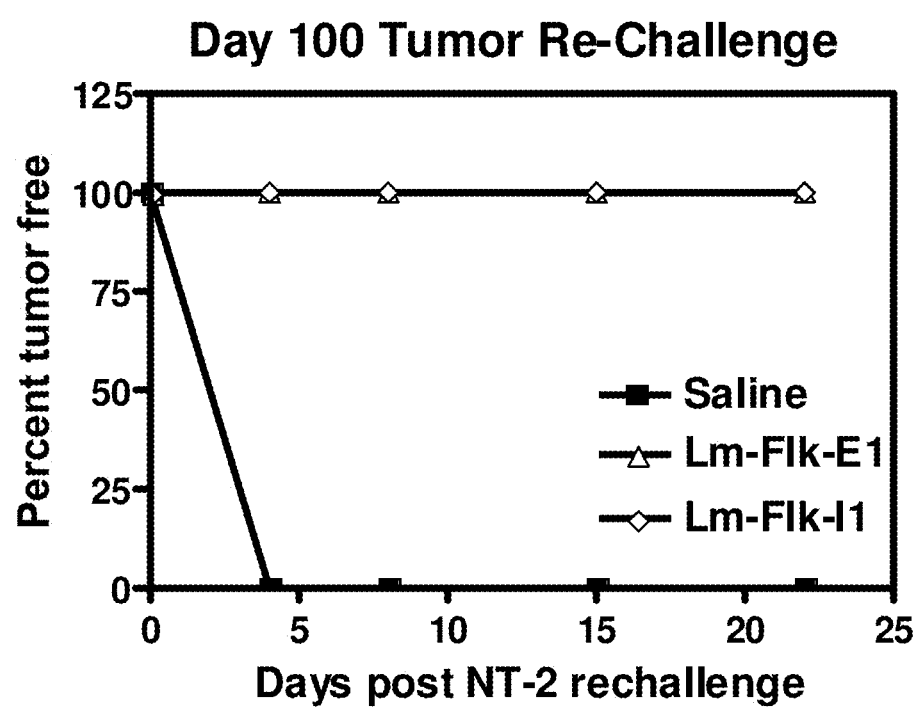
FIGS. 4A-4B. Mice with fully regressed tumors show long-term memory to tumor re-challenge.
Figure 4B:
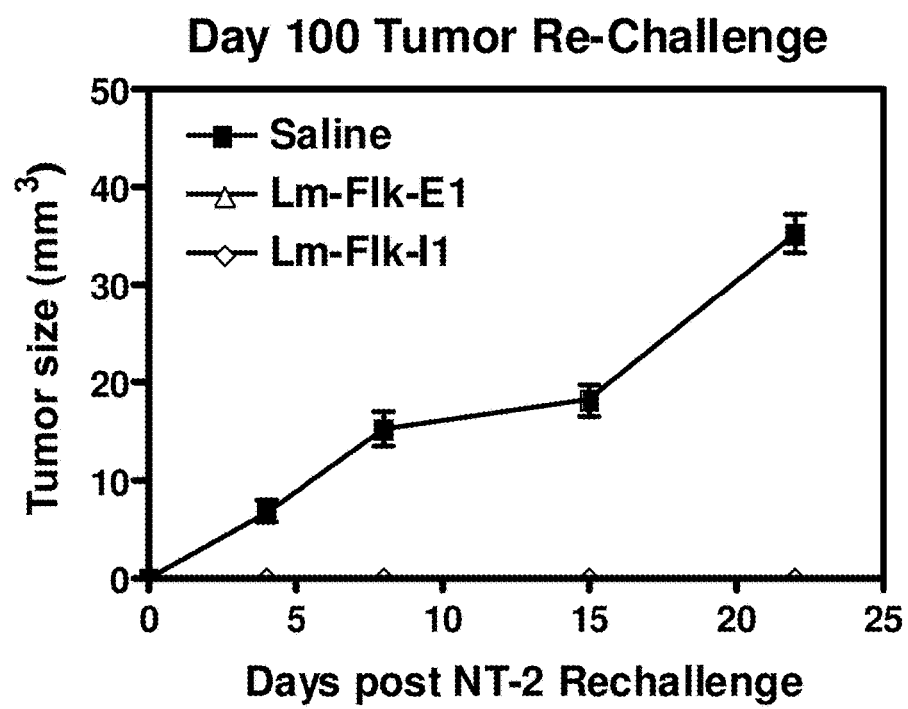

Therapeutic Efficacy of Lm-LLO-Flk-1 Vaccines in a Her-2/Neu-Expressing Tumor Model To test the ability of our vaccines to induce the regression of Her-2/neu+ breast tumors, we used the NT-2 tumor model, which overexpresses the rat Her-2/neu as a transgene and was originally derived from a spontaneous mammary tumor in the FVB/N Her-2/neu transgenic mouse. The NT-2 cell line does not express the Flk-1 molecule, and thus our antigen of interest is only located on the host vasculature. Cells were grown in vitro and transplanted subcutaneously into the flank of FVB/N mice. On day 4, when palpable (~4-5 mm in diameter) tumors had formed, mice were vaccinated and then boosted weekly for a total of three vaccinations. Vaccines Flk-E1 and Flk-I1 were able to induce regression, and in some mice complete eradication (Flk-E1: 2/8; Flk-I1: 2/8) of transplanted tumors by day 64 post-inoculation (FIG. 3A). However, Flk-E2 was unable to control tumor growth, which was similar to the group treated with the control Lm. Mice with completely regressed tumors were re-challenged with NT-2 on the contra-lateral side at 100 days post-tumor inoculation and re-growth of the new tumor was not observed suggesting long-lived anti-tumor immunity (FIGS. 4A & 4B).

Figure 3B:
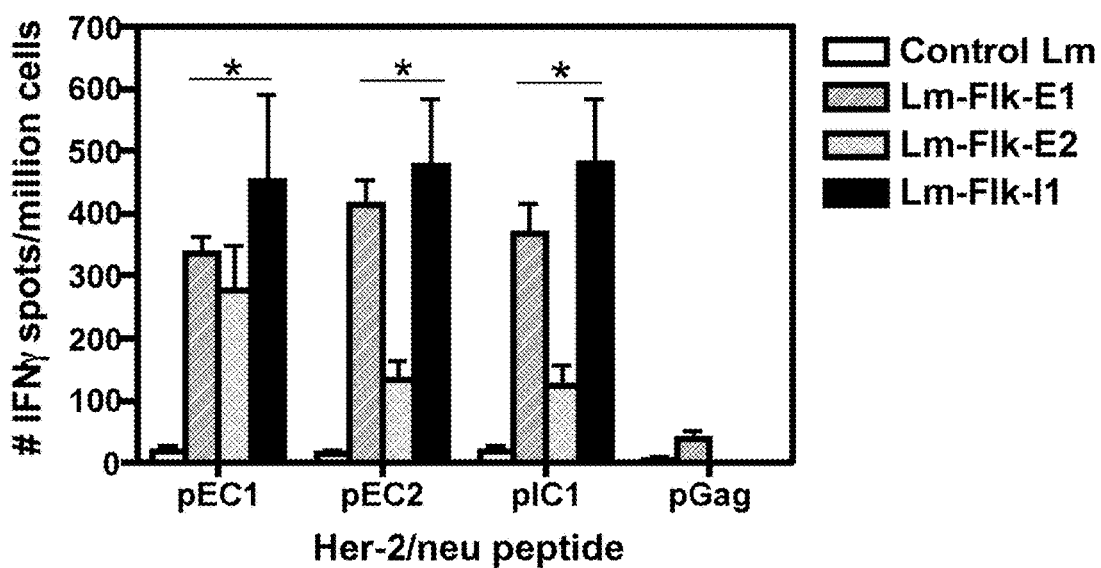
Figures 3C, 3D, 3E, 3F:
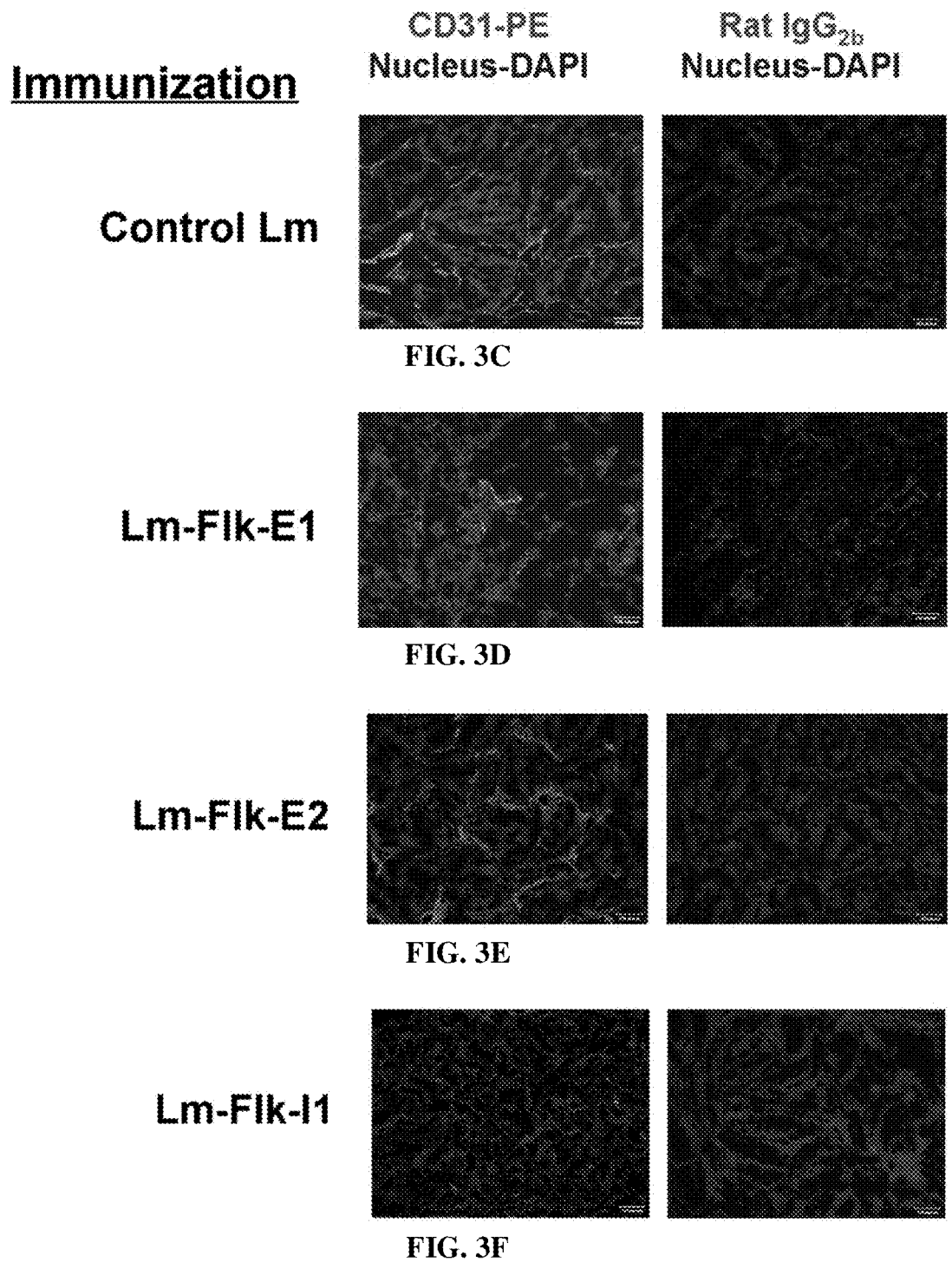
Figure 3G:
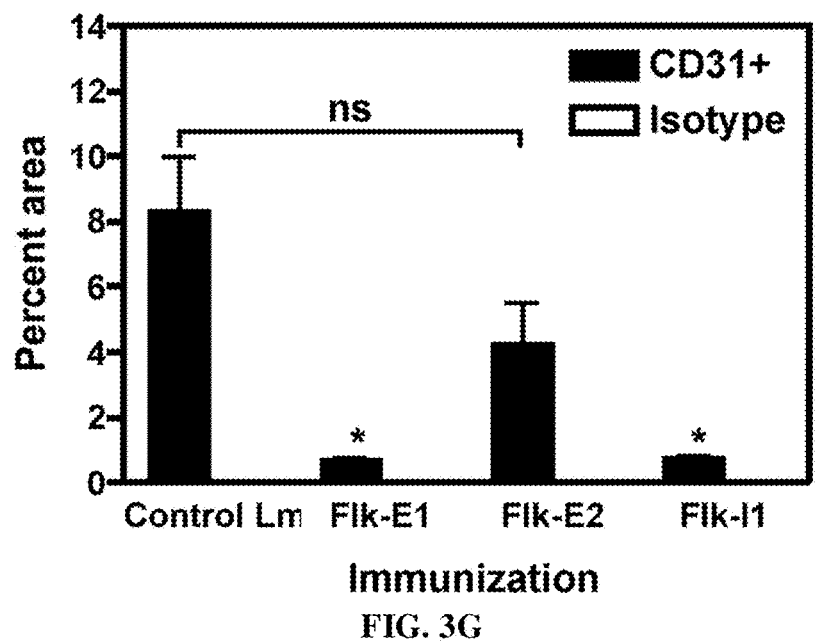
Figure 3H:
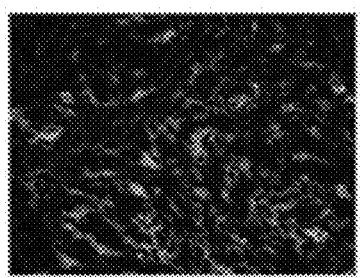
Figure 3I:
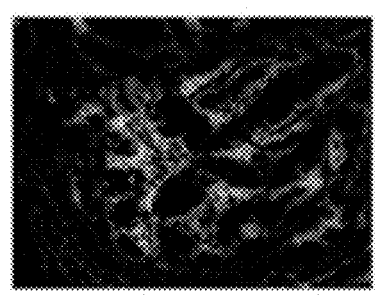
Figure 3J:
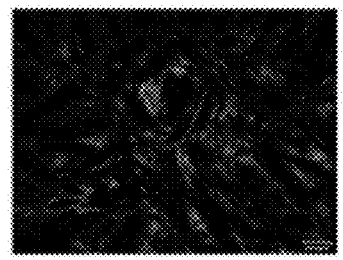

Microvascular density (MVD) of day 64 tumors was assessed by staining with the pan-endothelial cell marker CD31 and counterstained with the nuclear marker DAPI. As expected, MVD in tumors from the Flk-E2 treated group resembled those from control treated mice. However, a reduction in the density of $CD31^+$ vessels was seen in Flk-I1 treated mice and a further reduction was observed using the Flk-E1 vaccination (FIGS. 3C-3G). This reduction in $CD31^+$ vessels correlated with an increase in staining for the nuclear hypoxic marker, Hypoxia Inducible Factor-la (HIF-1α) in the Flk-E1 and Flk-I1 treated groups, but not for the control group (FIGS. 3H-3J). It is possible to hypothesize that regression of these Her-2/neu+ tumors, in addition to the reduction of tumor MVD, was due to anti-VEGFR2 cytotoxic T cells killing endothelial cells involved in tumor angiogenesis, possibly leading to tumor damage or growth restriction resulting in the observed regression. Subsequently, phagocytosed tumor debris could be cross-presented by local dendritic cells in draining lymph nodes and presented to anti-Her-2/neu CTLs, whose epitopes have been previously mapped in the FVB/N mouse. If this intermolecular epitope spreading occurred, we would expect that mice that exhibited the greatest regression would also have a high frequency of anti-Her-2/neu $CD8^+$ T cells. To test this hypothesis, we harvested splenocytes from day 64 mice, and performed an IFN-g ELISpot, re-challenging with three known epitopes from three different regions of Her-2/neu. We decided to use an ELISpot assay to measure anti-Her-2/neu responses because we had previously mapped CTL epitopes for different regions of the Her-2/neu molecule and the ELISpot assay is sensitive enough to detect a low frequency of specific T cells, unlike several cytotoxic assays that require in vitro stimulation and expansion. We found that Flk-E1 and Flk-I1 showed the greatest epitope spreading, while Flk-E2 showed the least (FIG. 3B, $*p<0.0^5$), strongly correlating with the extent of tumor regression found in vivo (FIG. 3A).

Example 3

Figure 5A:
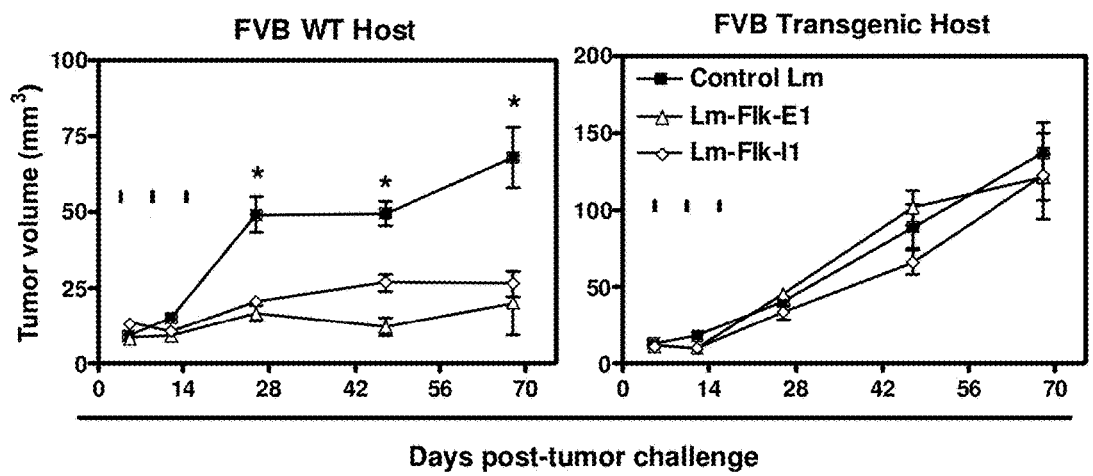
FIGS. 5A-5D shows anti-angiogenesis vaccines are not effective in mice tolerant to HER-2/neu.
Figure 5B:
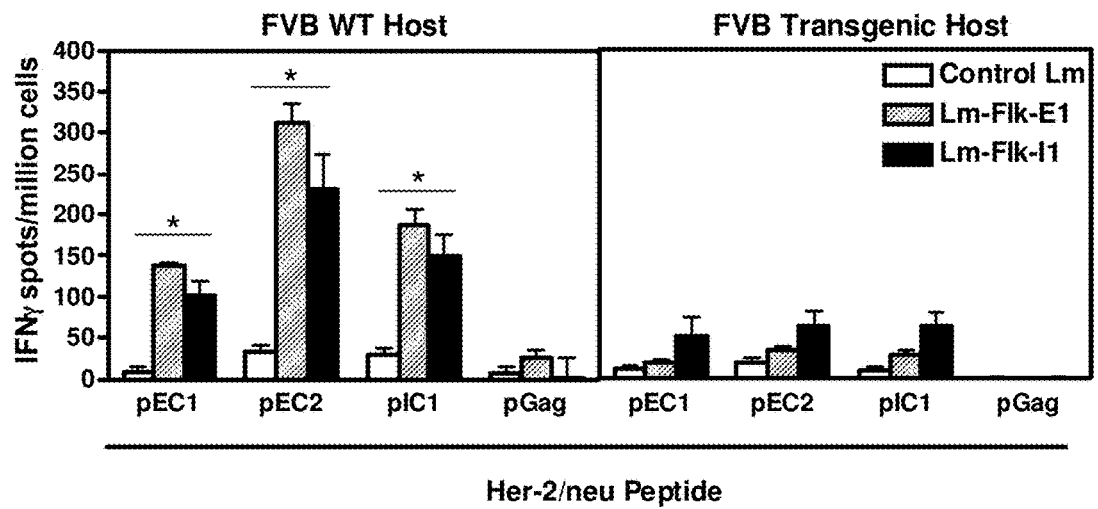
Figure 5C:
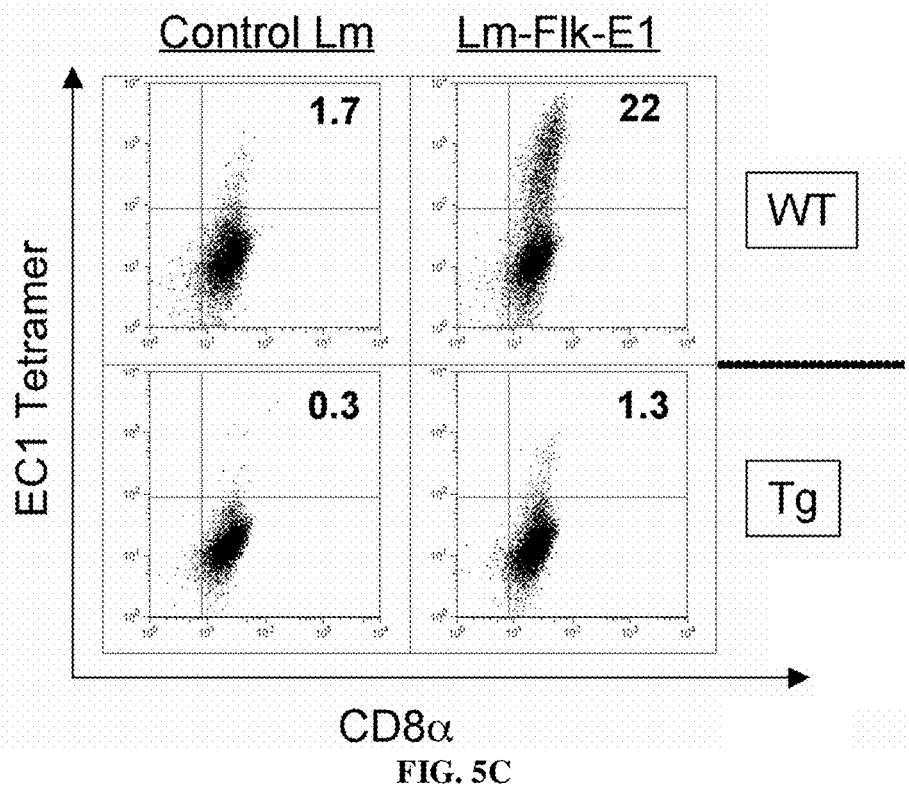
Figure 5D:
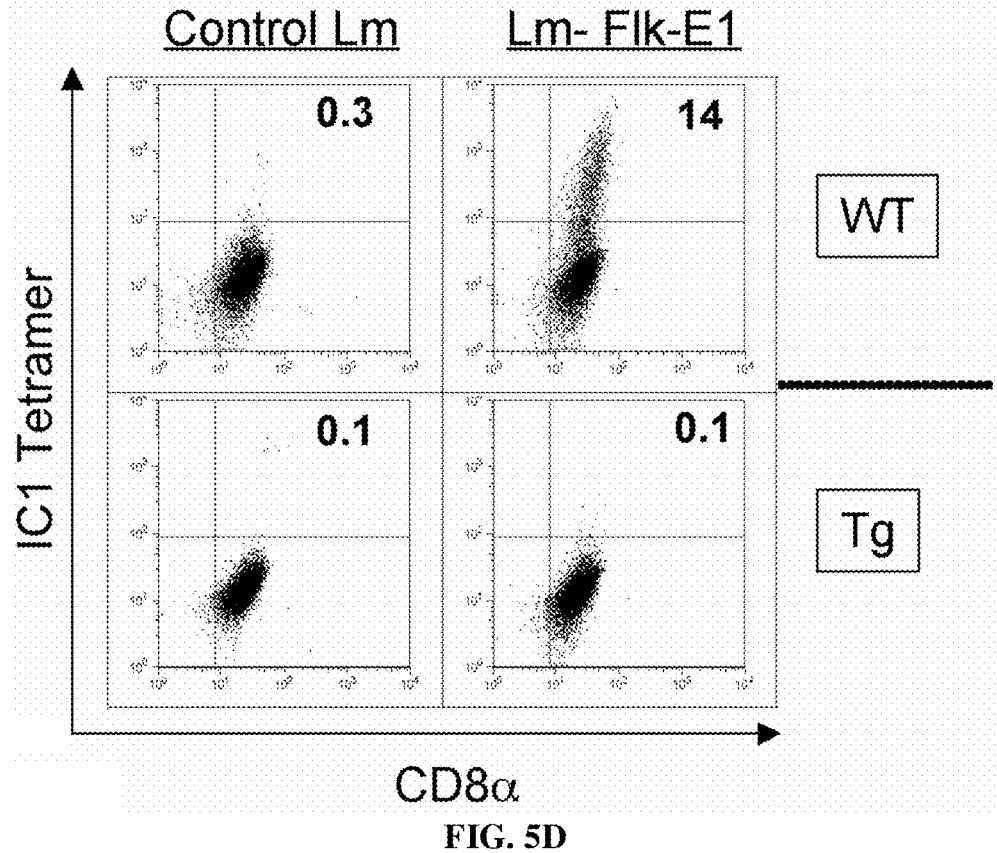

Anti-Angiogenesis Induced Tumor Regression is Dependent on Epitope Spreading to an Endogenous Tumor Antigen The presence of Her-2/neu epitope spreading suggested that tumor regression may not solely depend on anti-vascular events, but also on the immune response to the tumor antigen HER-2/neu. To test this hypothesis we repeated the same experiment using the two most potent vaccines, Flk-E1 and Flk-I1 but, in addition to inoculation of wild-type FVB/N mice, we also injected the NT-2 cells subcutaneously into its syngeneic progenitor strain, FVB/N Her-2/neu transgenic, which exhibits profound tolerance to the rat Her-2/neu molecule. Again, Flk-E1 and Flk-I1 slowed the growth of the NT-2 tumors in wild type FVB/N mice, as previously demonstrated (FIG. 5A, left panel). However, in the transgenic host where anti-HER-2/neu responses are limited by tolerance, we observed outgrowth of all tumors (FIG. 5A, right panel). Both these results reflected the epitope spreading observed towards the endogenous Her-2/neu protein demonstrated in the spleen (FIG. 5B) and at the tumor site as shown for the Flk-E1 vaccination (FIGS. 5C-5D). This suggests that anti-vascular events are not enough for tumor regression, but rather the combined effect on both the tumor's vasculature and directly on tumor cells is required for tumor death and ultimately regression.

Example 4

Vaccination with Lm-LLO-Flk-1 Vaccine Fragments can Prevent the Growth of Experimental Metastases An important use for anti-angiogenesis vaccines could be for the treatment or prevention of breast cancer metastasis. Tumor cells that metastasize are highly dependent on the development of new vessels, although smaller tumors do not completely rely on new vasculature. However, it has been hypothesized that once they have grown beyond a certain size, tumors become highly dependent on the formation of new vessels and thus become a possible target for anti-VEGFR2 CTLs. To test if our vaccines could protect against breast tumor dissemination we used an experimental metastasis system involving the direct inoculation of in vitro cultured tumor cells into the tail vein of mice allowing for rapid colonization of several downstream organs, especially the lung. Since after tail vein vaccination, the NT-2 model does not well colonize the lung (data not shown) we used 4T1, which is an aggressive, mouse breast carcinoma cell line from the Balb/c mouse. Balb/c mice were immunized thrice over the course of three weeks with either Lm-LLO-Flk-E1, or Lm-LLO-Flk-I1 or a control Lm vaccine. Mice were then injected with 50,000 4T1 cells i.v. and also s.c. within the same animal. The s.c. site injection was performed so that we could measure primary tumor growth, while the i.v. injection mimicked metastasis. Mice treated with the Flk-1 vaccines had prolonged tumor growth, slowed primary s.c. tumor size, increased survival, and reduced morbidity as compared to control mice (FIGS. 6A-6D). Unlike the poor responses seen against the primary 4T1 tumor, the rate of seeding and total metastases found in each animal was significantly lower in treated animals compared to control mice (FIGS. 7A-7E). A low level of epitope spreading to Her-2/neu was observed (FIG. 7F), probably because 4T1 weakly expresses the mouse Her-2/neu.

Figure 6A:
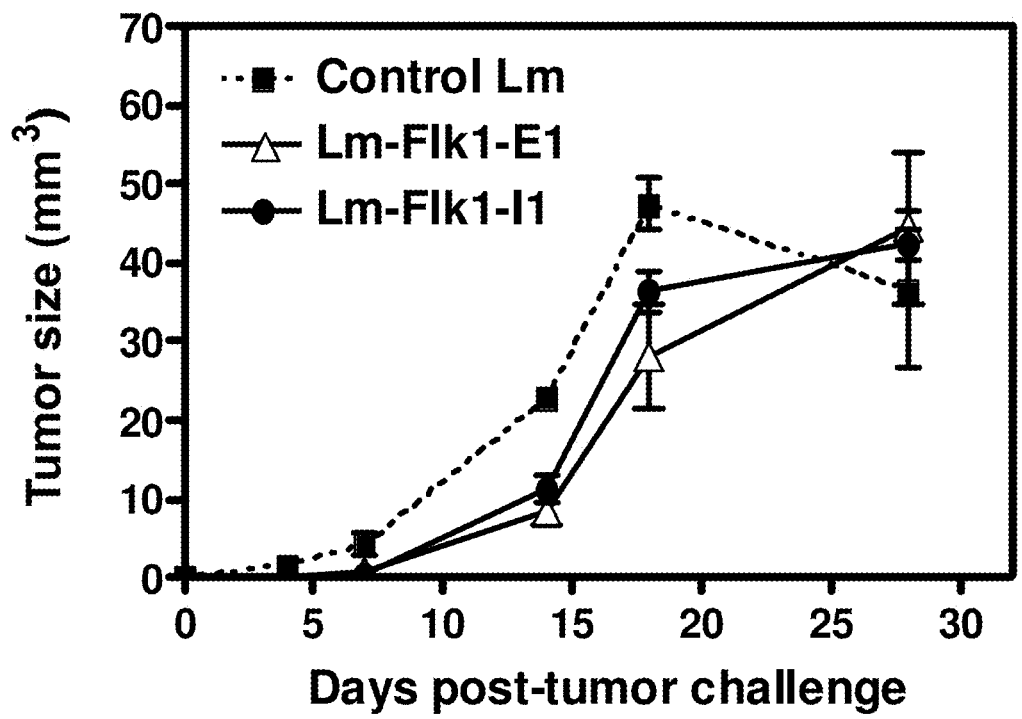
FIGS. 6A-D show mice protected with anti-Flk-1 Lm-vaccines show reduced primary tumor growth, tumor burden, and reduced morbidity and mortality when challenged with 4T1 experimental metastases.
Figure 6B:
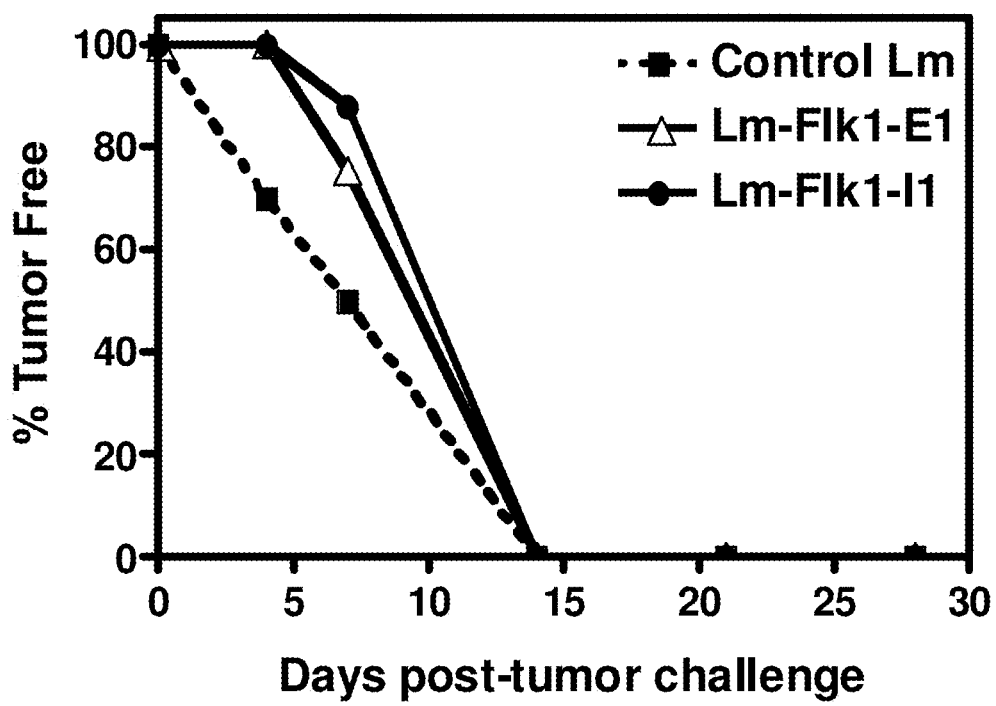
Figure 6C:
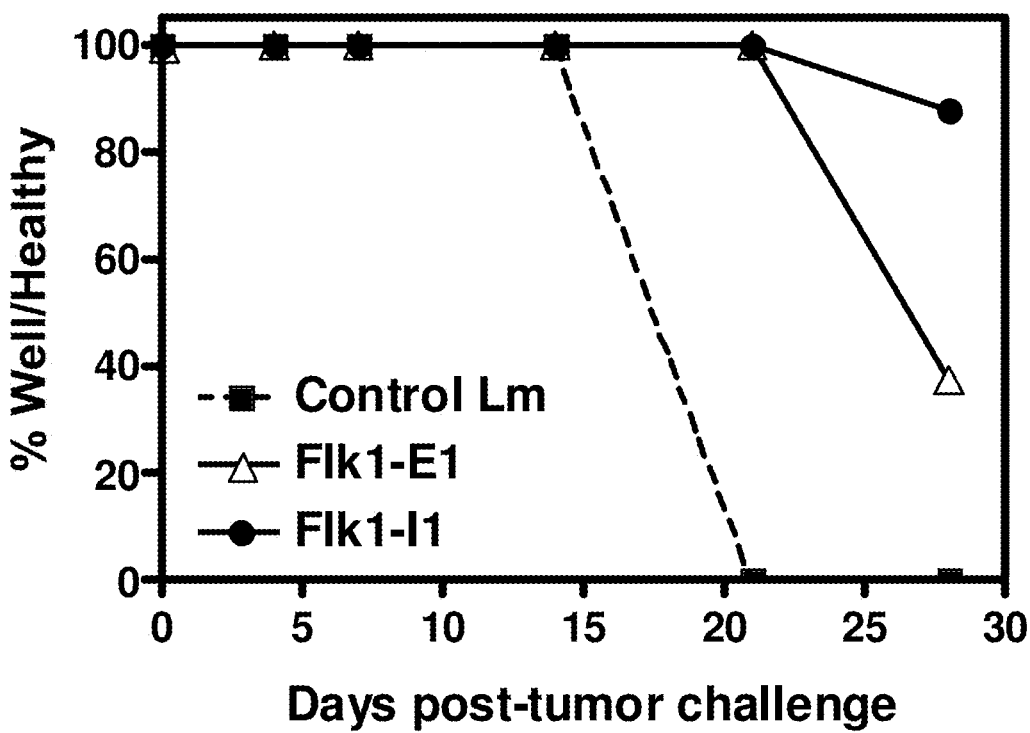
Figure 6D:
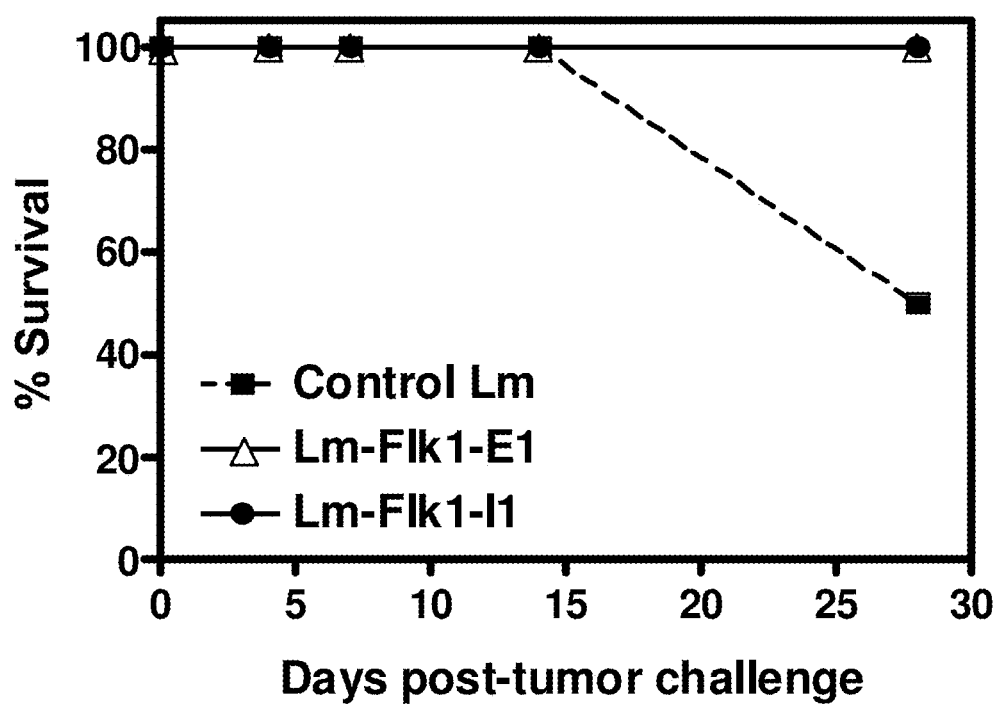
Figures 7A, 7B, 7C:
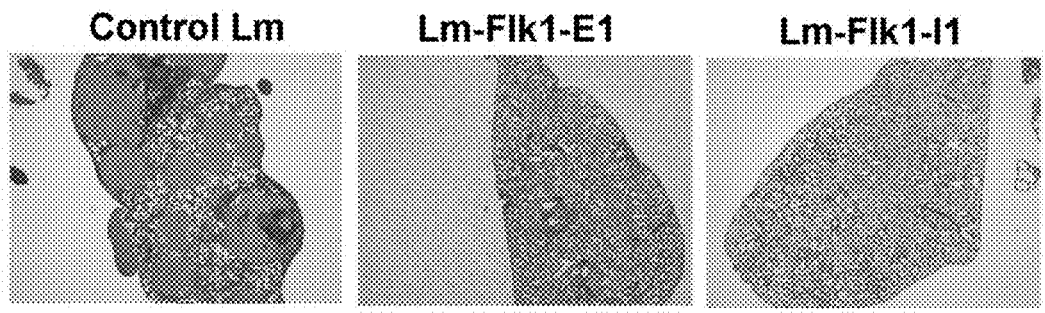
FIGS. 7A-7G. Flk-1 vaccines can protect mice from experimental metastases and induce weak Her-2/neu epitope spreading in a more aggressive tumor model for breast cancer.
Figure 7D:
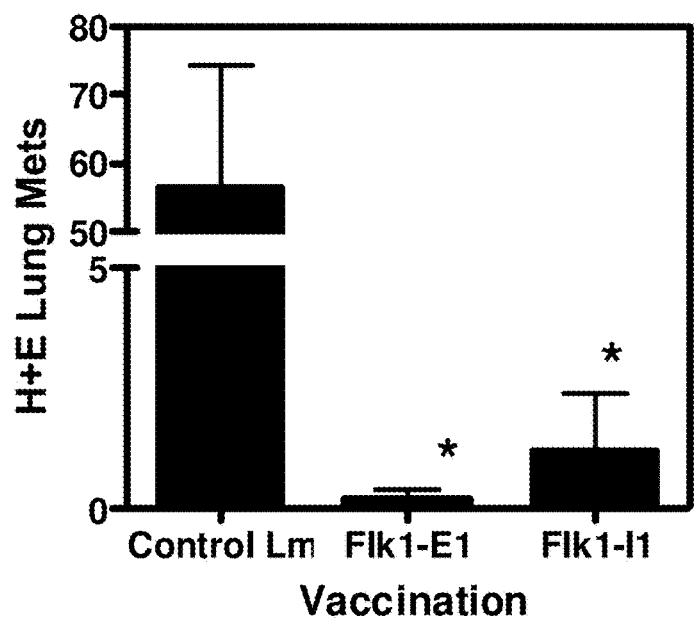
Figure 7E:
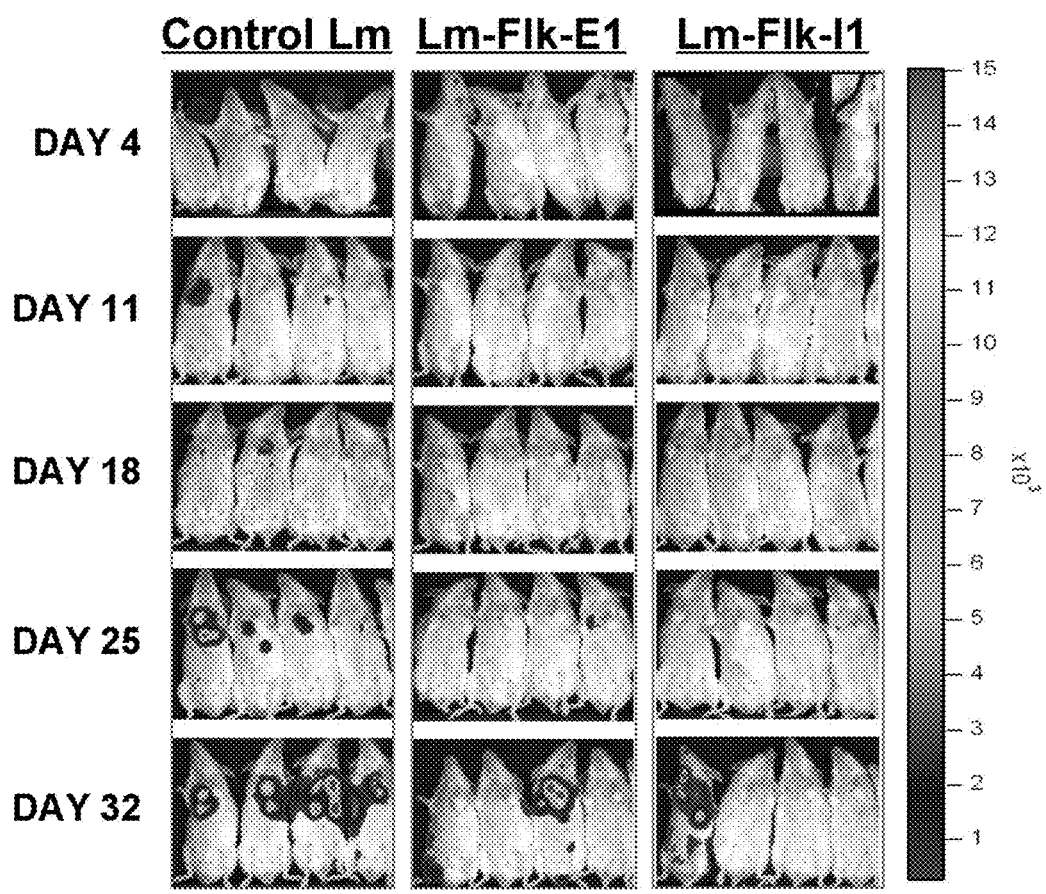
Figure 7F:
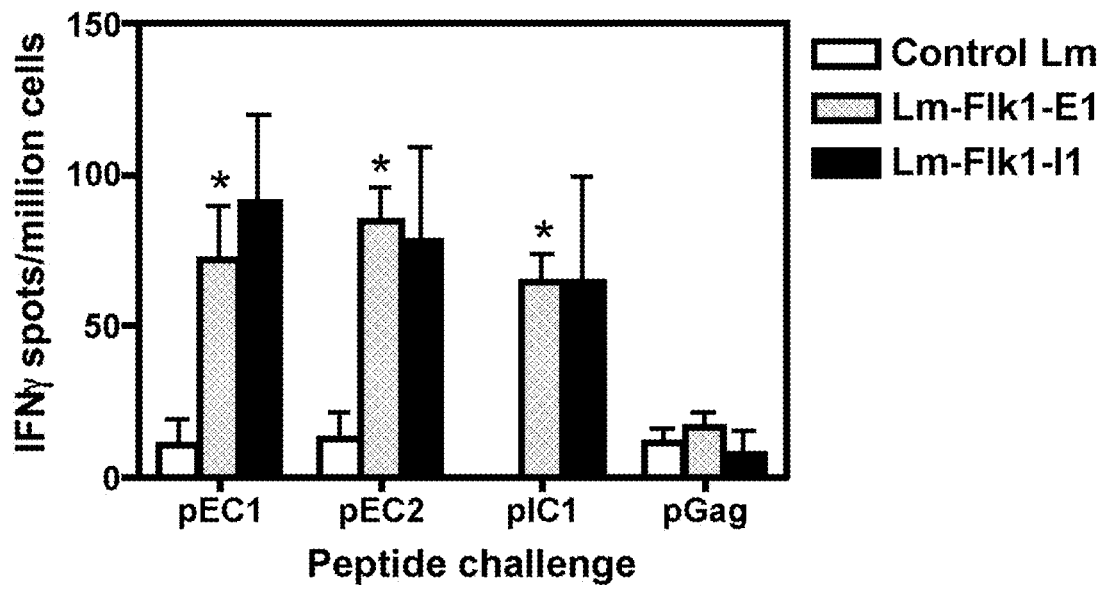
Figure 7G:
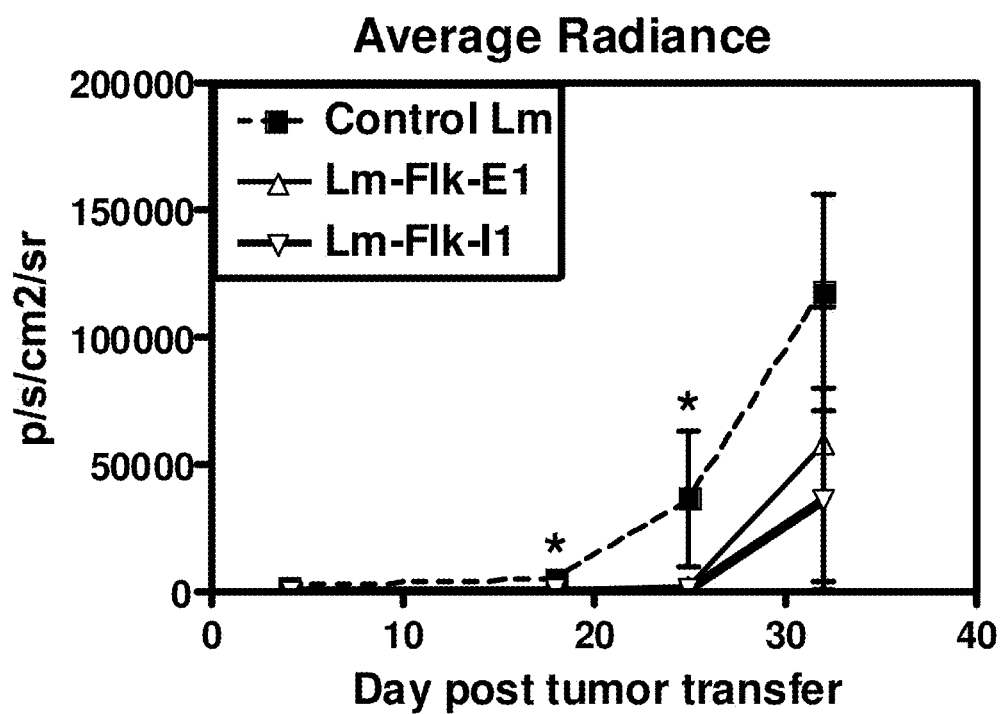

To more stringently test the hypothesis that immunizing against Flk-1 can prevent the seeding of lung tissue with experimental metastases, we used a bioluminescent model where individual tumor cells and masses can be visualized using non-invasive imaging. Mice were injected i.v. with 50,000 4T1 cells expressing the firefly luciferase gene (4T1-Luc) after several rounds of vaccination with the Lm-Flk-E1 and -I1 vaccines. On a weekly basis, mice were anesthetized and injected with a luciferase substrate (D-Luciferin) and imaged. Lung seeding was apparent by day 11 and control treated mice rapidly become colonized with 4T1-Luc cells by day 25 whereas none of the Lm-LLO-Flk-E1 and Lm-LLO-Flk-I1 treated mice showed any signs of lung seeding until at least day 32 at which point the control treated mice had become ill and were sacrificed (FIG. 7E). At day 32, only 25% of the Flk-1 vaccinated mice showed any lung tumors. It is possible that tumor masses were undetectable at this time point by this bioluminescent method since a signal for tumor cells was observed on day 25 but not day 32 for the Lm-Flk-E1 treated group. This very small signal on day 25 is below the 1000 cell threshold and may have lost some cellular mass within the following week to fall below the limit of detection for the system. Mice immunized with the control Lm rapidly became diseased by lung tumors, but the Flk-E1 and Flk-I1 Lm vaccinations delayed tumor burden, time to progression (day 25 for control treated versus day 32 for Flk-1 treated), and eventual disease (reduced morbidity as shown in FIG. 6D).

Example 5

Figure 8A:
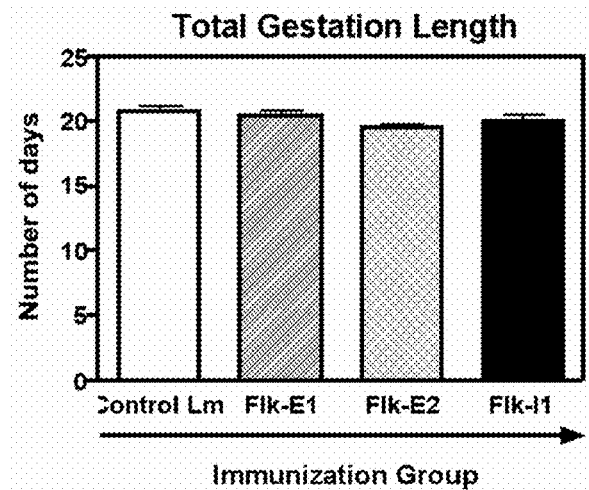
FIGS. 8A-8E show safety studies using the anti-angiogenesis Flk-1 vaccines. Mice were immunized thrice as performed in all previous experiments then were allowed to either mate or entered into wound-healing studies.
Figure 8B:
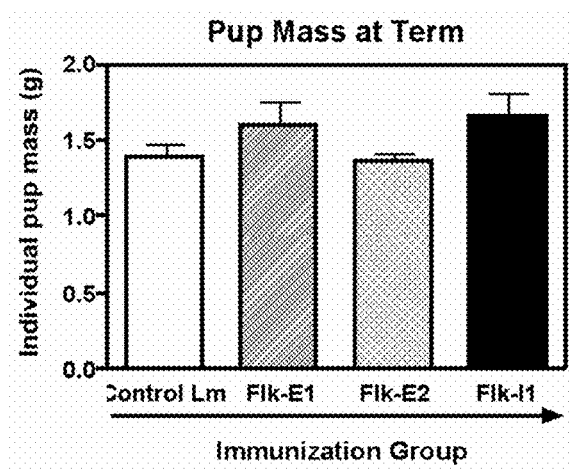
Figure 8C:
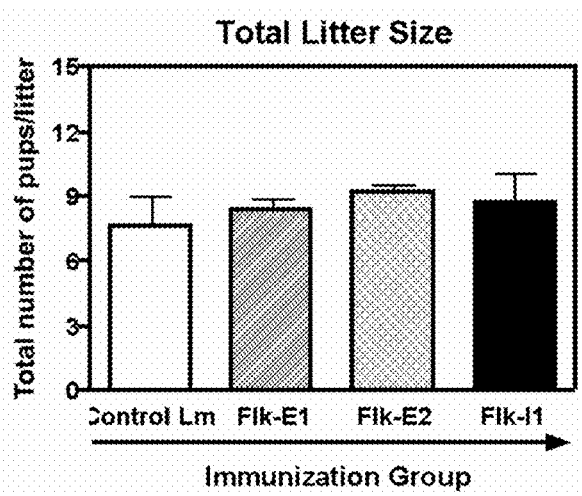
Figure 8D:
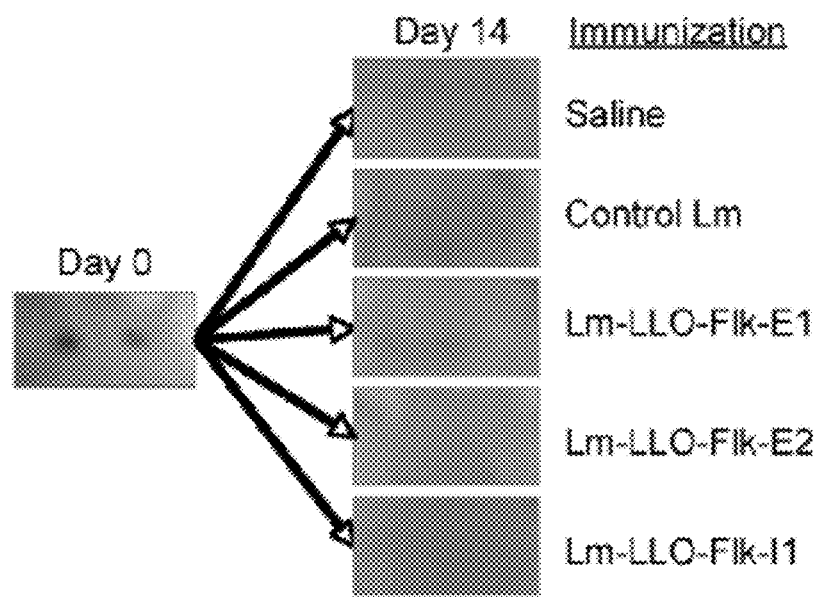
Figure 8E:
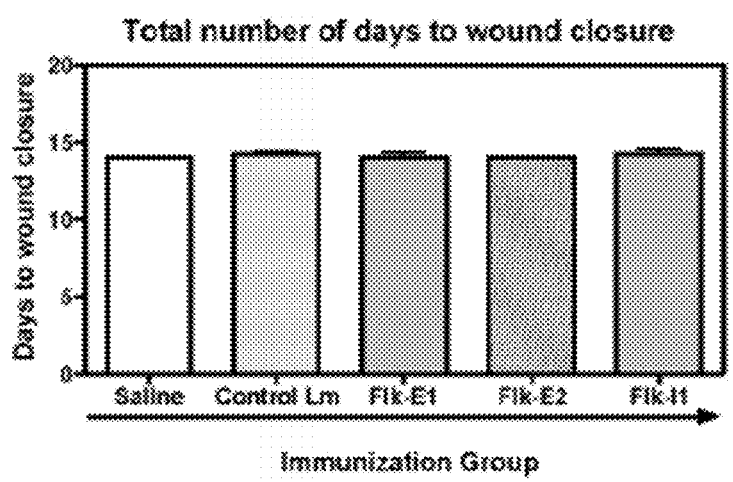

Immunization with Flk-1 has No Impact on Wound Healing, Pregnancy or Fertility in Mice To evaluate whether Lm-LLO-Flk-1 vaccines cause toxicity that is associated with angiogenesis inhibition, we studied wound healing, pregnancy and fertility in immunized mice. Mice were immunized thrice with Lm-LLO-Flk-E1, Lm-LLO-Flk-E2, Lm-LLO-Flk-I1, control Lm or saline alone before being mated or given sterile wound punches. We observed mice that were mated for length of gestation from coitus, mean pup mass at term, and total litter size. Wound punches were sterile but mice were caged together. Wound healing technique was followed according to previously described methods. Five mice from each immunization group were shaved and given sterile wound punches, two per animal then allowed to heal over time. Time to wound closure was measured. Full wound healing was considered complete, no scabs were left at time of wound closure. Immunization with Lm-LLO-Flk-E1, Lm-LLO-Flk-E2, or Lm-LLO-Flk-I1 had no impact on fertility, gestation length or pup mass at birth (FIGS. 8A-8C). Similarly, immunization had no significant impact on the time required for wound closure (FIGS. 8D-8E).

Figure 9:
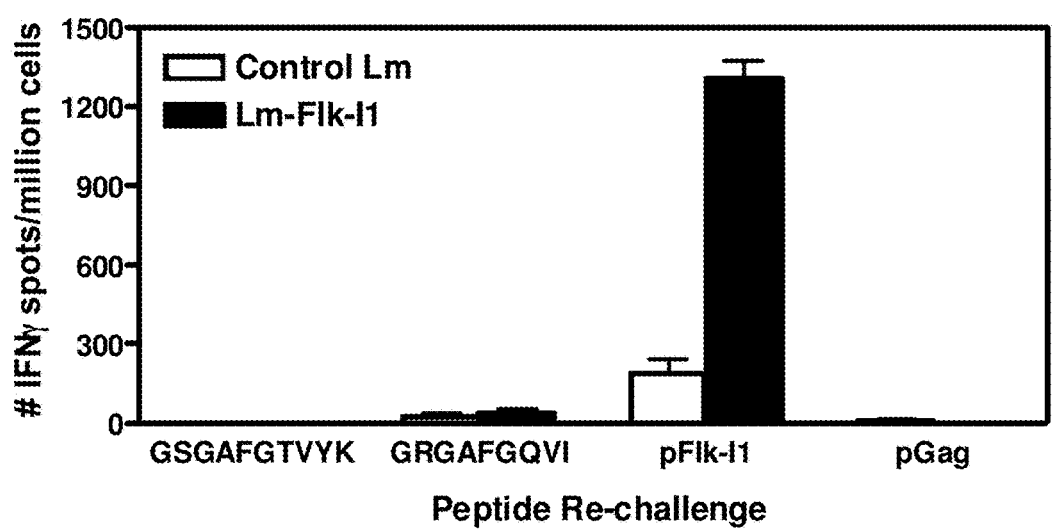
FIG. 9. Flk-1 vaccine induced epitope spreading may not be due to cross reactivity between Flk-1 and Her-2/neu shared domains Mice were immunized thrice with either control Lm or Flk-I1 vaccine. Splenocytes were processed and re-challenged ex vivo for the secretion of IFN-g in response to peptide challenge. Peptides included were the previously mapped pFlk-I1 epitope (PGGPLMVIV; SEQ ID NO: 1), a putative pIC1 epitope for Her-2/neu (GSGAFGT-VYK; SEQ ID NO: 2) or the epitope in question, a putative shared epitope between the Her-2/neu and Flk-1 kinase domains (GRGAFGQVI; SEQ ID NO: 3), and a third party epitope used as a negative control (pGag). Graph shows Mean±SEM, N=3/group.

To evaluate if the immune responses to Her-2/neu observed after Flk-I1 immunization was due to cross-reactivity between shared epitopes between Flk-1 and Her-2/neu, FVB/N mice immunized with Flk-I1 vaccine were evaluated for immunity to FLK-I1$_{839-848}$, which is cross-reactive to the rat Her-2/neu epitope G$\underline{S}$GAFG$\underline{TV}$Y$\underline{K}$ (SEQ ID NO: 2). Vaccination of mice with Lm-LLO-Flk-I1 lead to excellent responses against the previously mapped Flk-I1 epitope PGGPLMVIV (SEQ ID NO: 1). However no significant responses were seen against either the mouse Flk-I1$_{839-848}$ epitope or the homologous rat Her-2/neu IC1$_{732-741}$ epitope (FIG. 9). Thus the immune responses to Her-2/neu observed after Flk-I1 immunization were most likely due to epitope spreading and not due to cross-reactivity between shared epitopes.

Taken together, Lm-LLO-Flk-1 vaccines were able to eradicate some established breast tumors, reduce microvascular density in the remaining tumors, protect against tumor re-challenge and experimental metastases and induce epitope spreading to various regions of the tumor-associated antigen Her-2/neu. Tumor eradication was found to be dependent on epitope spreading to HER-2/neu and was not solely due to the reduction of tumor vasculature. However, vaccine efficacy did not affect normal wound healing nor have toxic side effects on pregnancy. Thus, an anti-angiogenesis vaccine can overcome tolerance to the host vasculature driving epitope spreading to an endogenous tumor protein and drive active tumor regression. Therefore, presented herein is a novel method of targeting both the tumor vasculature and an endogenous tumor antigen (Her-2/neu) using a single vaccine.

Example 6

Mutations Arise in Escape Mutants

Mice

The FVB/N Her-2/neu transgenic mice were housed and bred at the animal core facility at the University of Pennsylvania. Mice were six to eight weeks old when used at the start of the experiments, which were done in accordance with regulations by the Institutional Animal Care and Use Committee of the University of Pennsylvania.

Listeria Vaccine Strains.

Strains used were Lm-LLO-Flk-E1 and Lm-LLO-Flk-I1. The strain Lm-LLO-NYESO1 was used as a third party control vaccine for antigen specificity. Bacteria were selected on Brain Heart Infusion (BHI, Difco) plates supplemented with 34 μg/ml of chloramphenicol and 250 μg/ml of streptomycin, then grown in liquid culture and frozen in 1 ml aliquots at −80° C. For injection, the vaccines were washed twice with sterile PBS before administration.

Autochthonous Tumor Protection.

To test the ability of the anti-Flk-1 Listeria vaccines to impact on spontaneously arising tumors we used the FVB/N rat Her-2/neu transgenic female mouse which overexpresses the rat Her-2/neu molecule and spontaneously develops mammary tumors. For these long-term protection studies, we immunized female mice (N=15) a total of six times starting at 6 weeks of age and immunizing i.p. every three weeks until 21 weeks of age. Vaccines Lm-LLO-Flk-E1, Lm-LLO-Flk-I1, or Lm-LLO-NYESO-1 were injected at 0.1 LD50 suspended in PBS. Tumor burden was followed on a weekly basis. Once tumors were beyond 10 mm in size the animals were sacrificed and tumors were removed for analysis. Statistical analysis of differences in autochthonous tumor growth was done using the Kaplan-Meier log-rank test using GraphPad Prism Software, comparing the time of onset of tumor growth between each vaccine group and control groups.

Analysis and Mapping of Mutations.

Tumors were excised fresh and placed into RNAlater solution, stored at 4° C. for less than 2 weeks. We extracted mRNA from stored tumors using a Qiagen mRNA kit (Invitrogen), then generated cDNA via PCR. Individual PCR samples were further divided to allow sequencing of each individual fragment of Her-2/neu in stretches of 500-800 bp each (EC1, EC2, EC3, IC1, IC2) as was described elsewhere (Singh, 2007). Sequencing wss done by the Children's Hospital of Philadelphia (CHOP) Sequencing Facility and then analyzed using 4Peaks software 1.7.2. Mutations that did not occur in four or more individual PCR and sequencing reactions were discarded as PCR-induced mutations. Molecular modeling was done using MacPyMol.

PCR primer sequences:
EC1 FP:
(SEQ ID NO: 37)
AGGGCTGTCAGGTAGTGC

EC1 RP:
(SEQ ID NO: 38)
TGACCTCTTGGTTATTCG

EC2 FP:
(SEQ ID NO: 39)
ACCTGCCCCTACAACTAC

EC2 RP:
(SEQ ID NO: 40)
GACGCCCTCTACAGTTGC

EC3 FP:
(SEQ ID NO: 41)
GTGGATTGGCTCTGATTC

EC3 RP:
(SEQ ID NO: 42)
TGAGTTACAGACCAAGCC

IC1 FP:
(SEQ ID NO: 43)
CAAACGAAGGAGACAGAAG

IC1 RP:
(SEQ ID NO: 44)
CACCATCAAACACATCGG

IC2 FP:
(SEQ ID NO: 45)
CACTGCTGGAAGATGATG

IC2 RP:
(SEQ ID NO: 46)
TTTGTGGCGATGGAGACC

Figure 10A:
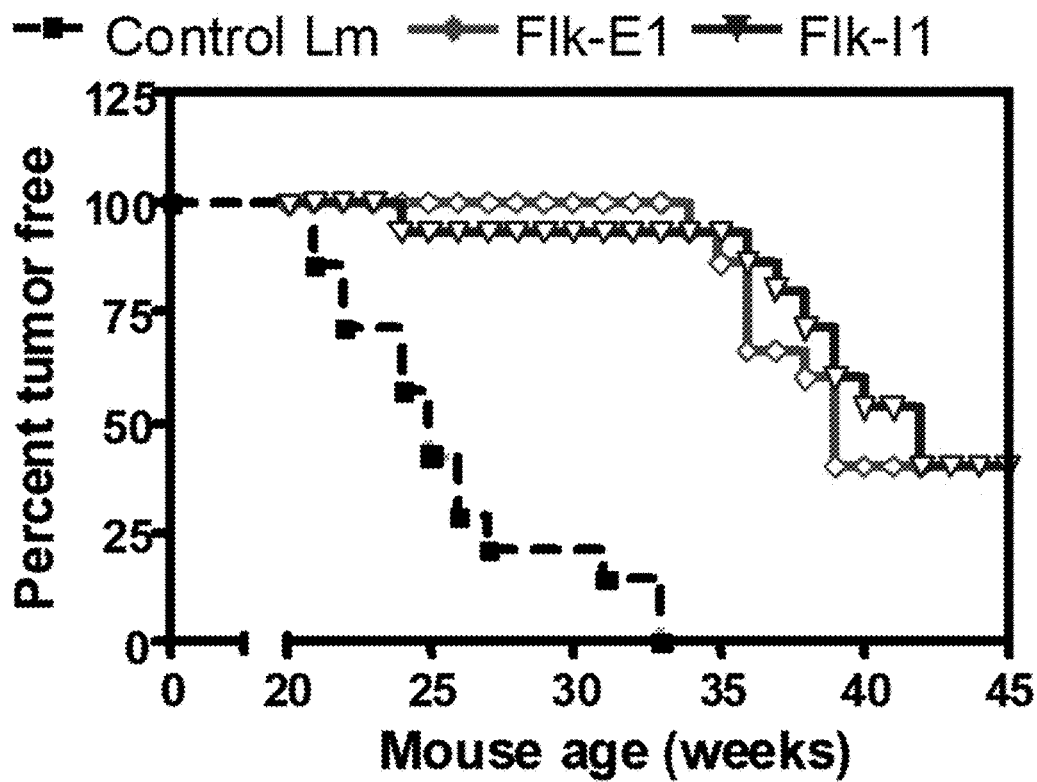
Figure 10E:
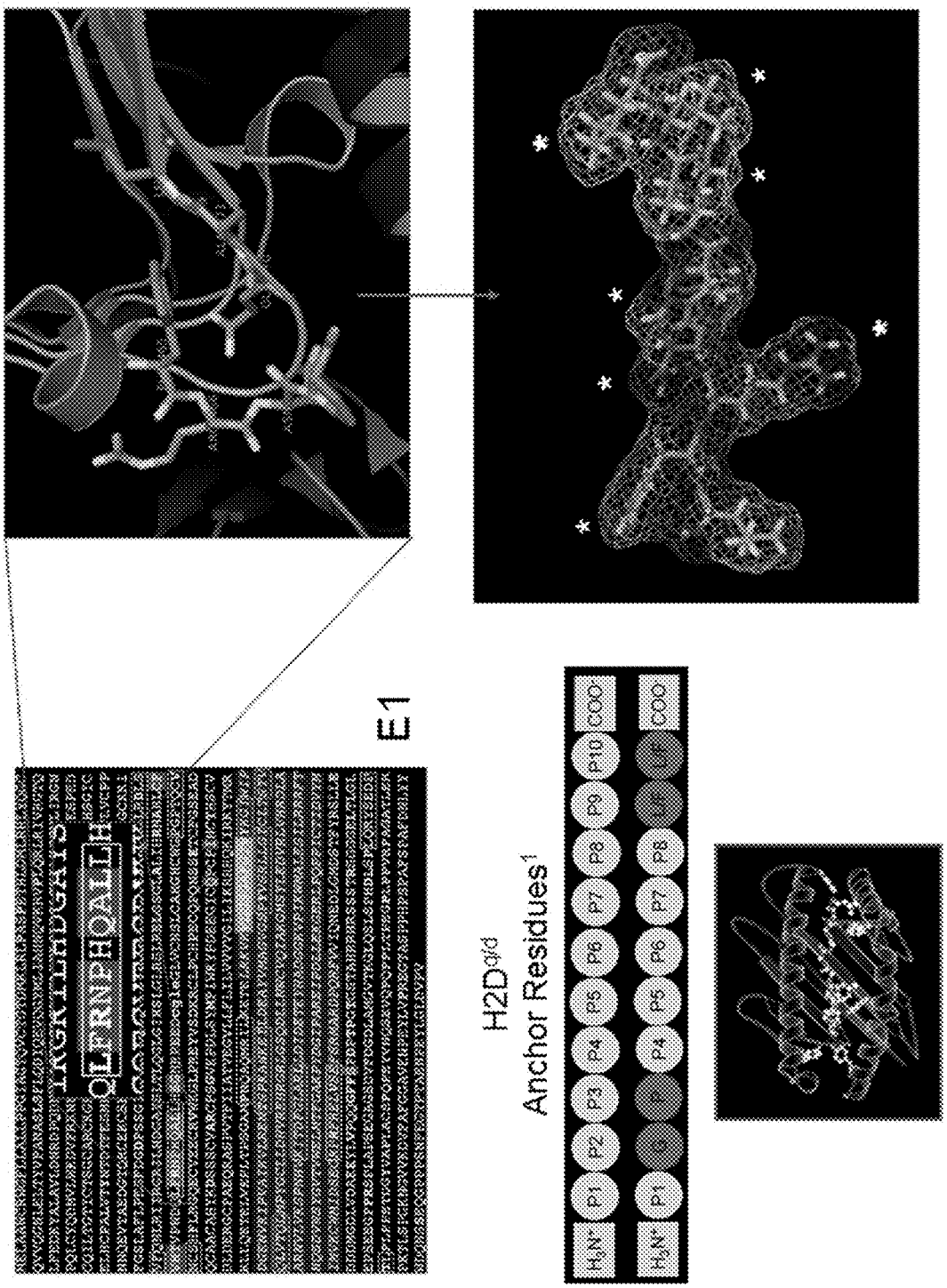
FIG. 10E. Tumor outgrowth is due to mutations arising in key CTL epitopes responsible keeping the tumor in check. Looking closer at "hot-spots" or strings of mutated residues, we found that several mutated residues are found within previously mapped (Singh, 2005 and 2007) CTL epitopes. One such epitope shows mutations in key amino acids responsible for anchoring the epitope to the H2Dq MHC I molecule. Other "hot-spots" are being investigated for new CTL epitopes.

Transgenic FVB/N mice expressing rat Her-2/neu were vaccinated with Flk-E1, Flk-I1, or control Lm every 3 weeks starting at 6 weeks old, and tumors were measured weekly after the final vaccination. Vaccination with Flk-E1 and Flk-I1 increased the percentage of tumor-free mice compared to control Lm-vaccination. Between week 35 and 40, there were a number of mice in the Flk-E1 and Flk-I1-vaccinated mice that developed tumors. Tumors from each mouse were examined for mutated Her-2/neu message. Message RNA was collected, cDNA synthesized and sequenced. The resulting sequence was paired alongside the wild-type sequence to determine mutated residues. Only mutations that arose 4 times or more were considered true mutations (FIGS. 10A-10D). Several of the mutated residues within the "hot-spots" or strings of mutated residues were within previously mapped CTL epitopes. One such epitope shows mutations in key amino acids responsible for anchoring the epitope to the H2Dq MHC I molecule (FIG. 10E).

Example 7

Targeting of Breast and Melanoma Brain Metastases

Experiments were performed using the methods as described hereinabove.

Balb/c mice were immunized thrice with each vaccine, either anti-human Her-2/neu or control vaccination NYESO1. Murine breast carcinoma cells stably expressing the firefly luciferase gene (EMT6-Luc cells from John Ohlfest's lab at University of Minnesota) were grown in vitro then injected into the brain of anesthetized mice at 5,000 cell per mouse. EMT6-Luc cells express low levels of mouse Her-2/neu (data not shown) Cells were allowed to grow before being imaged on the indicated days. While brain metastases were clearly seen in NYESO1-vaccinated mice, anti-human Her-2/neu vaccination controlled brain tumors on days 3, 8 and 11 after experimental induction of metastases (FIG. 11A).

C57Bl/6 mice were immunized thrice with each vaccine, either anti-human HMWMAA-C or control vaccination NYESO1. B16F10-Luc mouse melanoma cells (from Jeff Miller's lab at UCSF) were grown in vitro then injected into the brain of anesthetized mice at 5,000 cells per mouse. B16F10 parental line do not express HMWMAA (personal communication), thus the only source of HMWMAA is on pericytes and glial cells. Vaccination of mice with anti-human HMW-MAA-C reduced brain tumors on days 11 and 15 after experimental induction of metastases (FIG. 11B). Thus, vaccination with either HMW-MAAC or Her-2/neu is protective against brain metastases, even if the tumor cells do not express HMW-MAA.

Example 8

Construction of Novel Anti-CD105/Endoglin Listeria-Based Vaccine-Therapeutic

Figure 14:
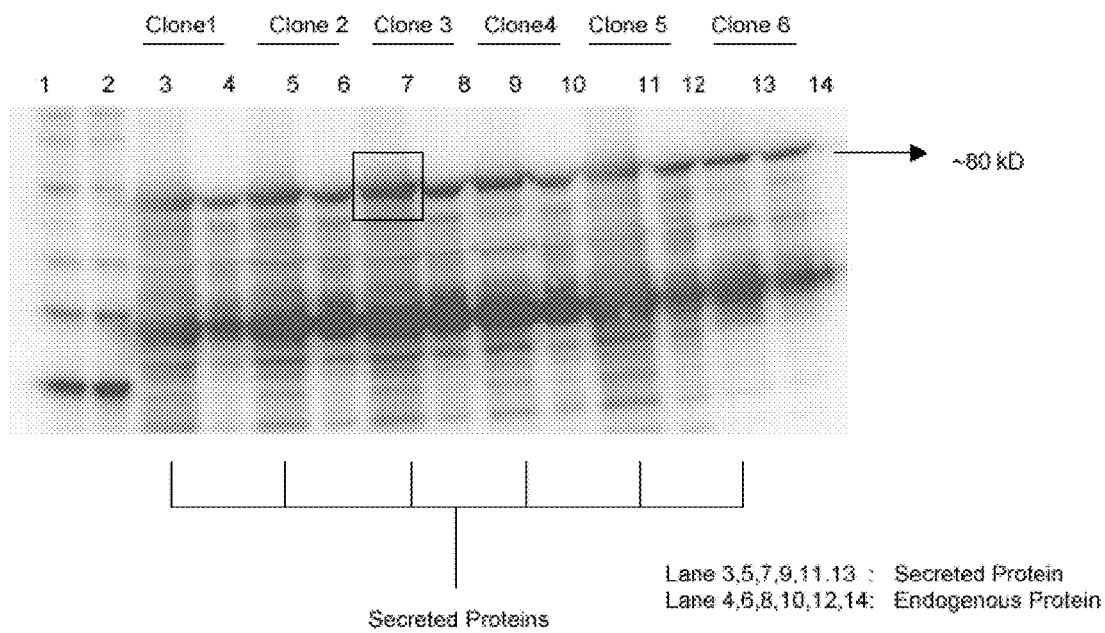
FIG. 14. Lm-LLO-CD105A expresses and secretes a protein of appropriate size (~80 kD) detected by an anti-LLO antibody and Western blotting: The XFL7 strains were transformed with CD105A plasmid using electroporation. The transformed XFL7 cells were plated on 37 ug/mL and 250 ug/uL of chloramphenicol and streptomycin. The colonies that formed during the two day incubation period were grown in LB media, spun down and the supernatantand cell lysate were subjected to Western blotting to detect the fusion fusion protein either as a secreted protein in the supernatant or n endogenous protein trapped within the bacterial cell.
Figure 15:
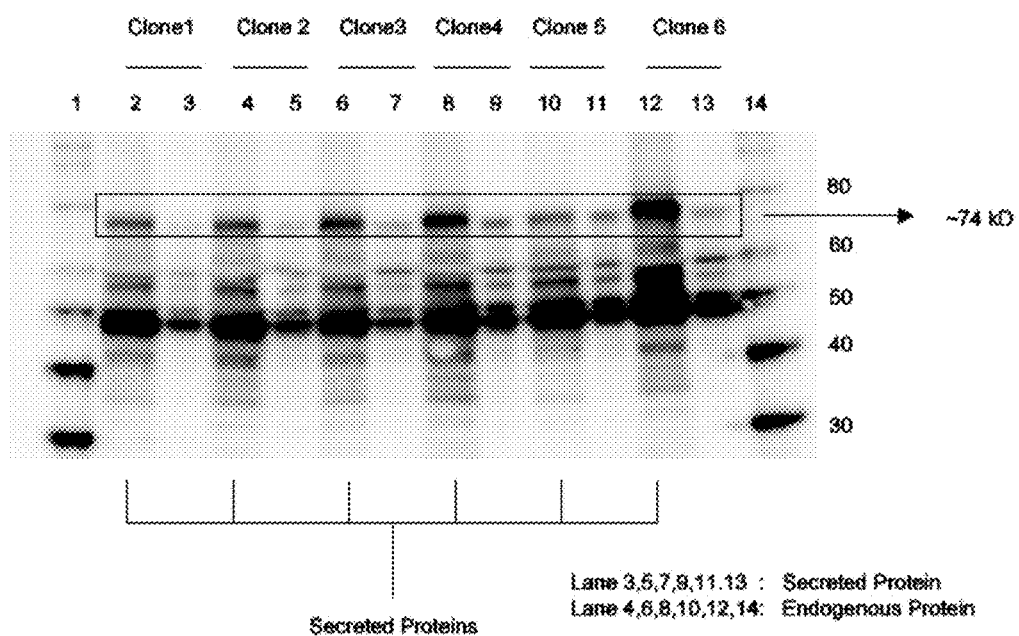
FIG. 15. Lm-LLO-CD105B expresses and secretes a protein of appropriate size (~74 kD) detected by an anti-LLO antibody and Western blotting: The XFL7 strains were transformed with CD105A plasmid using electroporation. The transformed XFL7 cells were plated on 37 ug/mL and 250 ug/uL of chloraphenicol and streptomycine. The colonies that formed during the two day incubation period were grown in LB media, spun down and the supernatant and cell lysate were subjected to Western blotting to detect the fusion fusion protein either as a secreted protein in the supernatant or n endogenous protein trapped within the bacterial cell.

A construct of an Lm strain that expressed a rather large fragment of endoglin (FIG. 12) did not secrete the fragment when fused to LLO, therefore it was redesigned to two novel Lm constructs, Lm-LLO-CD105A (aa17-319) and Lm-LLO-CD105B (359-588) that span nearly the entire endoglin gene (FIG. 13A; SEQ ID NO: 55) and include putative CTL epitopes, determined using RANKpep, that lie outside the region of endoglin that had been previously targeted (FIG. 12). By potentially including more immunodominant epitopes within these novel constructs expansion of the pool of CTL epitopes were used to enhance vaccine efficacy. Further by making the fusion proteins smaller and removing regions of high hydrophobicity from the constructs, these fusion proteins were better secreted by Lm. Genes encoding these fragment were cloned into CD105pGG-34 (FIG. 13B). Both Lm-LLO-CD105A (FIG. 14) and Lm-LLO-CD105B (FIG. 15) expressed and secreted fragments of the appropriate size.

Example 9

Figure 16A:
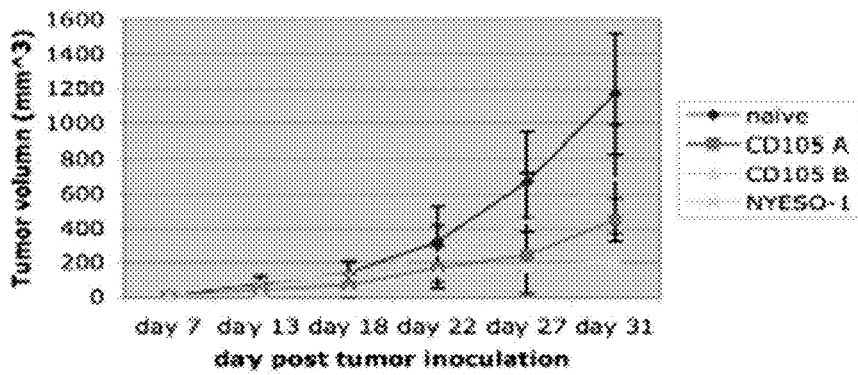
FIGS. 16A-B. Growth of 4T1 tumors (2×105 cells implanted in the mammary fat pad) in Balb/c mice immunized with Lm-LLO-CD105 A and B compared to a control vaccine Lm-LLO-NY-ESO-1.
Figure 16B:
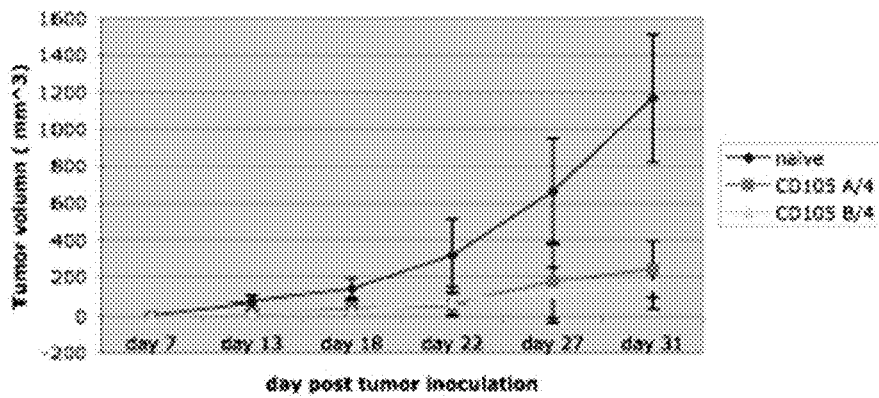
Figure 17:
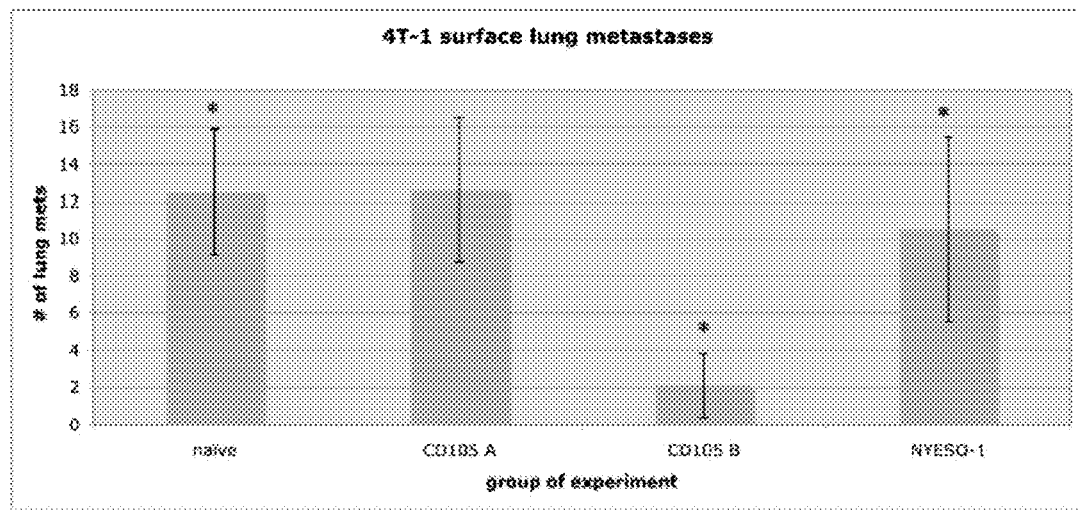
FIG. 17. Mice from the experiment shown in FIG. 5B were sacrificed on day 32 and lungs were removed and inflated with PBS. The visible surface metastases were counted under a dissecting microscope. A significant decrease was observed only for Lm-LLO-CD105B compared to naive (p<0.01) or Lm-LLO-NY-ESO1 (p<0.05).

Lm-LLO-CD105A and B Impact on Primary and Metastatic Growth of Breast Tumor 4T1 in the Balb/C Mouse The BALB/c mouse 4T1 breast tumor, the more malignant of our breast tumor models since it rapidly metastasizes when implanted into the mammary gland, was chosen as the first test of the vaccines shown in Example 8. $2 \times 10^5$ 4T1 cells were implanted in the mammary fat pad in Balb/c mice. Mice were vaccinated with $2 \times 10^8$ cfu of each vaccine on either day 1, 8 and 15 or on days 4, 11 and 18. Both vaccine regimens showed a significant slowing of tumor growth compared with naive or control vaccinated mice (FIGS. 16A-16B). On day 32, the mice were sacrificed and their lungs were removed and examined for metastatic spread. Interestingly, only Lm-LLO-CD105B showed a statistically significant reduction in surface lung metastases (FIG. 17).

Next, CTL responses in these mice were examined. As an initial attempt to determine the immunogenic regions of the endoglin molecule that could be recognized by CD8$^+$ T cells, the two fragments were subjected to analysis by RANKpep (http://bio.dfci.harvard.edu/RANKPEP/) and SYFPEITHI (http://www.syfpeithi.de/). From this the two most promising peptides for CD105A: AGPRTVTVM (SEQ ID NO: 52) (a $D^d$ binder) and for CD105B: AYSSCGMKV (SEQ ID NO: 53) (a $K^d$ binder) were selected Their positions in the endoglin sequence are underlined in FIG. 13A.

These two peptides were used in ELISpot analyses to stimulate splenocytes taken from mice shown in FIG. 16B, that had been vaccinated on days 4, 11 and 18, four days following their last vaccination. However they did not stimulate T cells to secrete interferon-gamma, compared to a control H-$2^d$ restricted peptide from HIV Gag, which suggests that they are not CTL epitopes (FIG. 7). Epitope spreading to two endogenous tumor antigens expressed at low levels by 4T1 was also analyzed. The first is an envelope glycoprotein, gp70, from the endogenous ecotropic murine leukemia virus. An epitope, designated AH1, SPSYVYHQF (SEQ ID NO: 54), frpm gp70, with $L^d$ restriction, has been mapped for the BALB/c mouse. Interestingly it was found that both Lm-LLO-CD105A and B induced epitope spreading to this antigen. Epitope spreading to HER-2/neu, was also investigated. Two known epitopes in the extracellular domain of HER-2/neu, EC1 and EC2 and one from the intracellular domain were used. Although no significant increase in IFN-gamma ELISpots against IC1 for either endoglin vaccine compared to the control vaccine Lm-LLO-NY-ESO-1 was observed, spreading to EC1 and EC2 using the Lm-LLO-CD105A vaccine was witnessed (FIG. 17).

Figure 18:
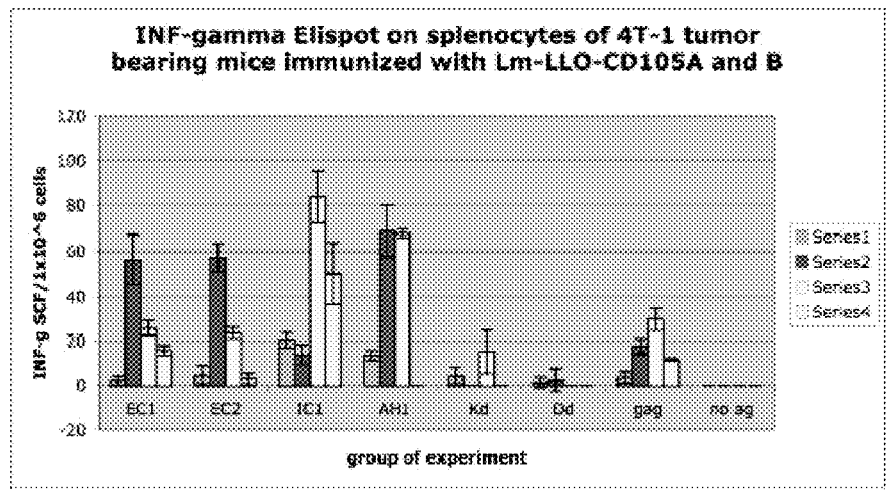
FIG. 18. Immunization with Lm-LLO-CD105A and B induces epitope spreading to endogenous antigens HER-2/neu and gp70 and the induction of antigen-specific T cells in the spleen. On day 22 post tumor implantation in the experiment shown in FIG. 5B, spleens were removed from 3 mice, pooled, and a single cell suspension was analyzed by ELISpot after stimulation with the peptides shown. Note that Kd and Dd are two peptides from the endoglin sequence that were predicted to bind to these MHC class I molecules. They reside in CD105A: AGPRTVTVM (Dd) and in CD105B AYSSCGMKV (Kd).

Tumors from the mice were examined for antigen-specific infiltrating T-cells, from which the splenocytes were harvested for HER-2/neu and gp70 specific T cells using FACS and tetramer analysis. Significant increases in EC1, EC2 and AH1 specific T cells in tumors were observed, and modest increases in IC1 specific T cells, from Lm-LLO-CD105 vaccinated mice compared to those vaccinated with Lm-LLO-NY-ESO-1 were also observed (FIG. 18).

Example 10

Figure 19A:
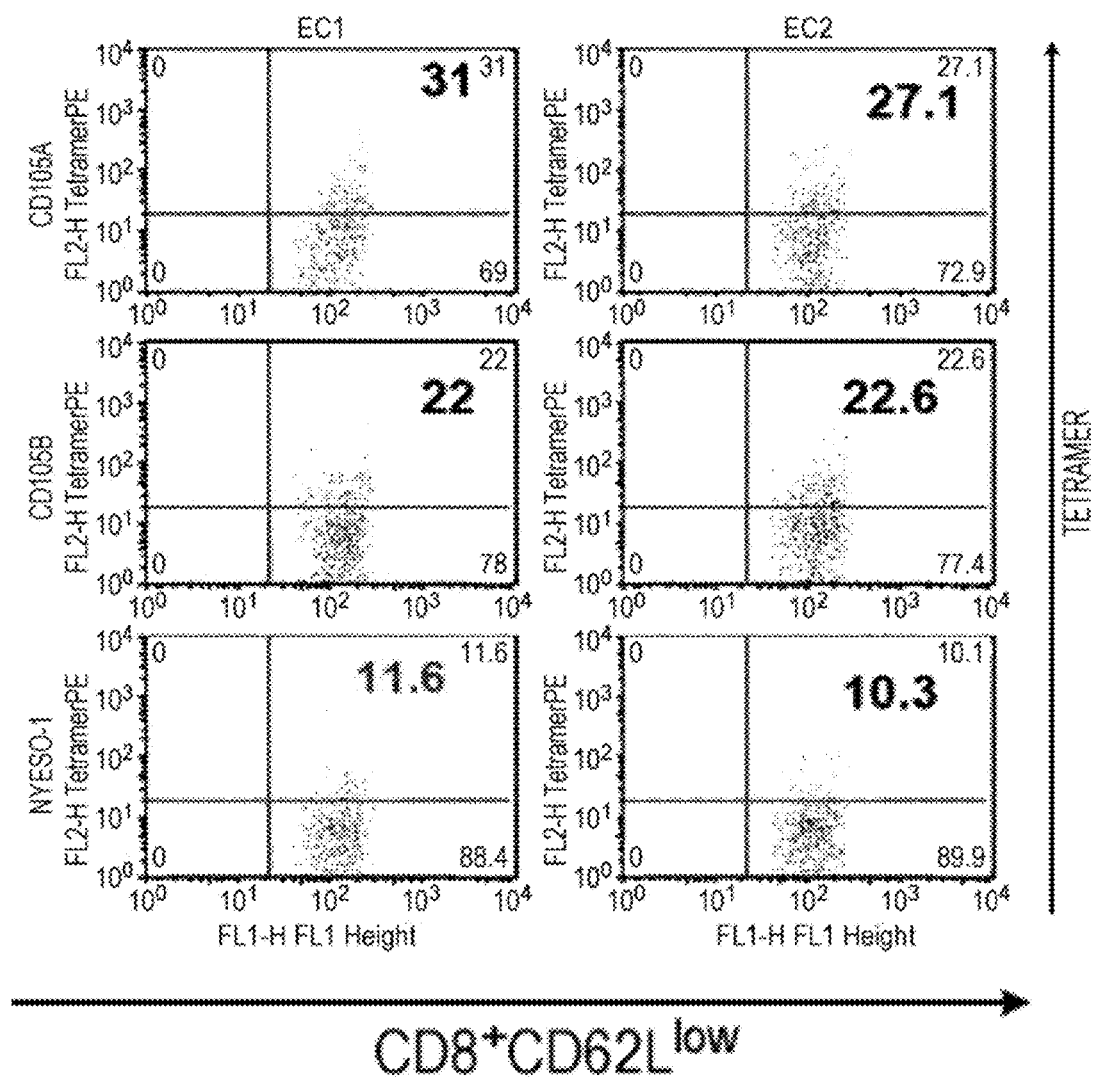
FIGS. 19A-19B. Immunization with Lm-LLO-CD105A and B induces epitope spreading to endogenous antigens HER-2/neu and gp70 and the induction of antigen-specific T cells that infiltrate the tumor. On day 22 post tumor implantation in the experiment shown in FIG. 5B, tumors were removed from 3 mice, pooled and processed for FACS analysis and stained with EC1 (FIG. 19A), EC2 (FIG. 19A), IC1 (FIG. 19B) and AH1 (FIG. 19B) tetramers, anti CD8 and CD62L, CD11B. The CD11B– population was gated on CD8+, CD62Llow and analyzed for antigen specificity using the tetramers shown.
Figure 19B:
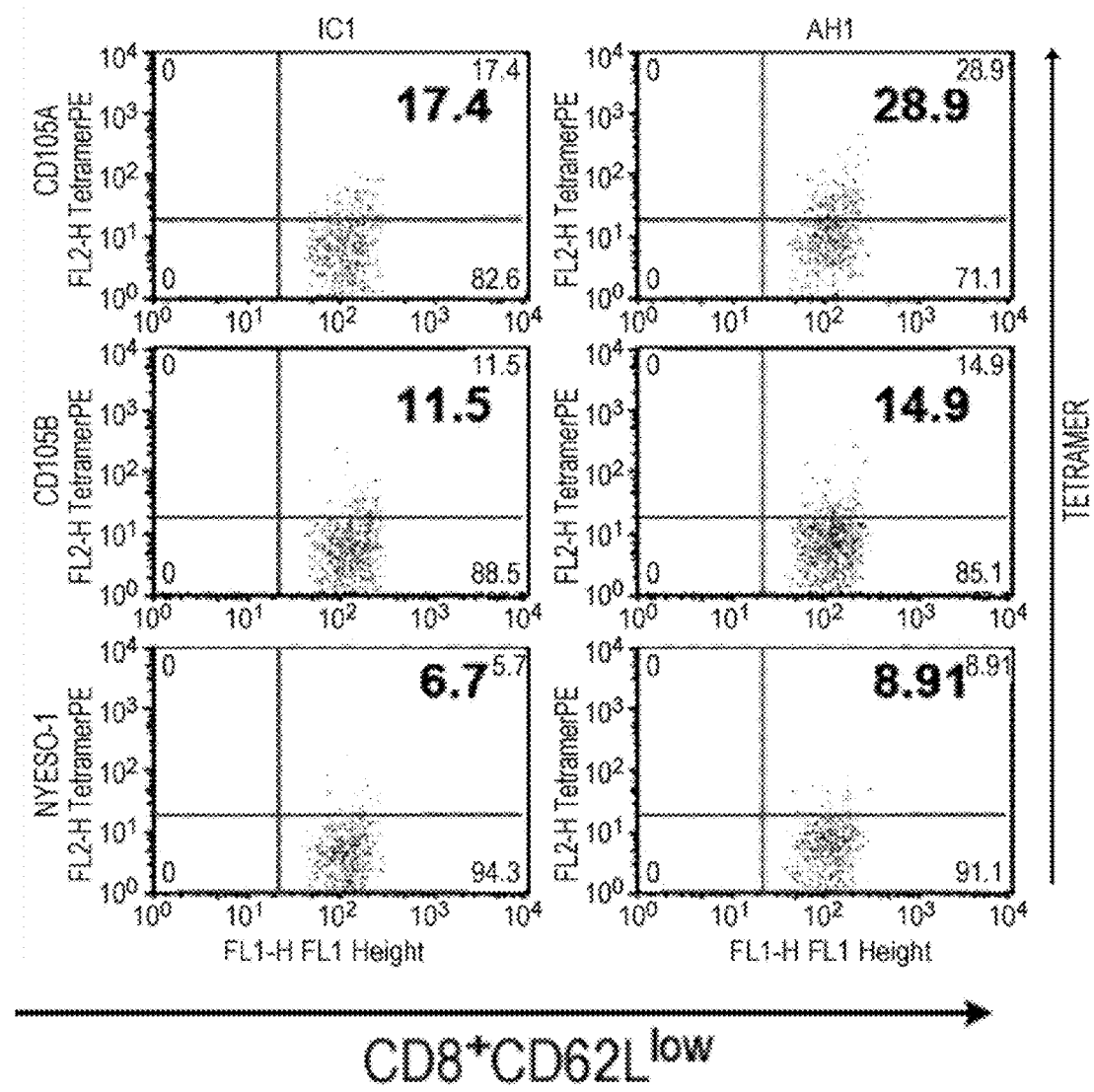
Figure 20:
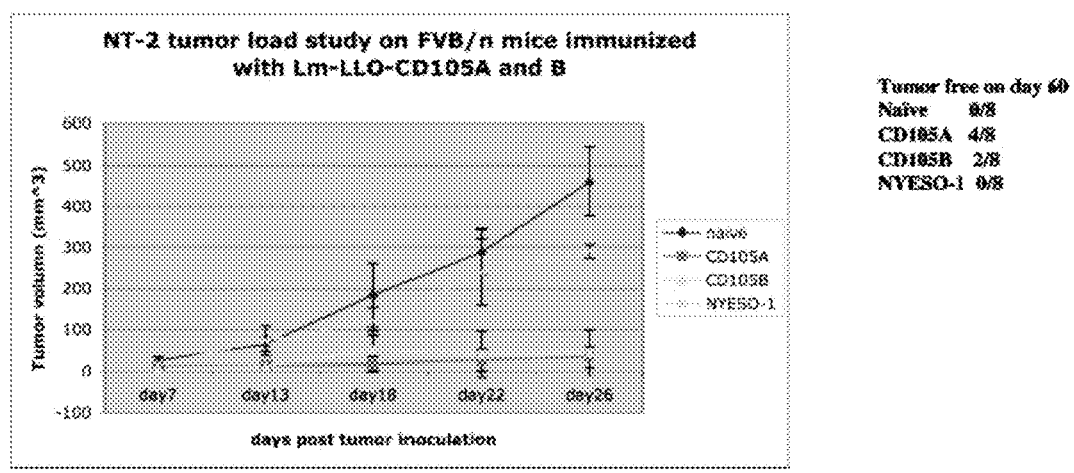
FIG. 20. Growth of NT-2 (1×106 cells) tumors implanted sub-cutaneously in FVB mice, which were subsequently immunized with Lm-LLO-CD105 A and B or a control vaccine Lm-LLO-NY-ESO-1 on days 4, 11 and 18, with 2×108 cfu of each vaccine.

Studies on the Use of Lm-LLO-CD105A and B to Impact on the Growth of the Her-2/Neu Positive Breast Tumor NT2 Derived from the FVB Her-2/Neu Transgenic Mouse The endoglin vaccines were tested in other breast tumor model in the FVB mouse using the transplantable HER-2/neu tumor NT2. Further, $1 \times 10^6$ tumor cells were implanted sub-cutaneously in FVB mice and they were immunized with Lm-LLO-CD105 A and B on days 4, 11 and 18, with $2 \times 10^8$ cfu of each vaccine. Lm-LLO-NY-ESO-1 was used as the control vaccine. Both vaccines significantly impacted tumor growth (FIGS. 19A-19B) and at day 60, 50% of the mice immunized with Lm-LLO-CD105A were tumor free and 25% of the mice vaccinated with Lm-LLO-CD105B were tumor free compared to none in the unvaccinated group or the group vaccinated with Lm-LLO-NYESO1.

What is claimed is:

1. A method for treating a metastatic tumor or cancer in the brain of a subject, the method comprising the step of administering to said subject a recombinant *Listeria* strain expressing an immunogenic fragment of an angiogenic factor, wherein said angiogenic factor is associated with a vasculature of said tumor or cancer in said subject, wherein said angiogenic factor is a high molecular weight melanoma associated antigen (HMW-MAA)-C, wherein said immunogenic fragment is fused to an additional polypeptide, wherein said additional polypeptide is selected from the group consisting of an N-terminal ActA and a PEST amino acid sequence, wherein said subject mounts an immune response against said angiogenic factor or against said vasculature, and wherein said treating reduces growth of said tumor or cancer, or reduces the size of said tumor or cancer.

2. The method of claim 1, wherein said method elicits protection against metastasizing of a breast tumor or cancer, a gastric tumor or cancer, an ovarian tumor or cancer, a melanoma, or a Her-2/neu-expressing tumor or cancer to the brain.

3. The method of claim 1, wherein said subject mounts an immune response against said immunogenic fragment or against said tumor associated-vasculature.

4. The method of claim 3, wherein said immune response comprises a therapeutic immune response useful in treating, inhibiting, or suppressing said tumor in said subject.

5. The method of claim 1, wherein said HMW-MAA-C immunogenic fragment comprises the amino acid sequence at positions 2160-2258 of the HMW-MAA protein.

6. The method claim 1, wherein said immunogenic fragment is expressed from an hly promoter, a prfA promoter, an actA promoter, or a p60 promoter.

7. The method of claim 1, wherein said immunogenic fragment is expressed from an episomal vector or from the *Listeria* chromosome.

8. The method of claim 1, wherein said additional polypeptide enhances the immunogenicity of said immunogenic fragment.

9. The method of claim 1, wherein said recombinant *Listeria* strain is a recombinant *Listeria monocytogenes* strain.

10. The method of claim 1, wherein said recombinant *Listeria* strain has been passaged through an animal host.

11. The method of claim 1, wherein said recombinant *Listeria* strain induces the release of one or more anti-angiogenic factors.

12. The method of claim 11, wherein said anti-angiogenic factor is interferon-gamma.

13. The method of claim 1, wherein said metastatic tumor or cancer in the brain comprises a metastatic tumor or cancer of a breast tumor or cancer, a gastric tumor or cancer, an ovarian tumor or cancer, a melanoma, or a Her-2/neu-expressing tumor or cancer.

14. A method for reducing the incidence of a metastasis of a tumor or cancer to the brain of a subject diagnosed with a primary tumor or cancer, the method comprising the step of administering to said subject a recombinant *Listeria* strain expressing an immunogenic fragment of an angiogenic factor, wherein said angiogenic factor is associated with a vasculature of said tumor or cancer in said subject, wherein said angiogenic factor is a high molecular weight melanoma associated antigen (HMW-MAA)-C, wherein said immunogenic fragment is fused to an additional polypeptide, wherein said additional polypeptide is selected from the group consisting of an N-terminal ActA and a PEST amino acid sequence, wherein said subject mounts an immune response against said angiogenic factor or against said vasculature, and wherein said reducing the incidence of a metastasis reduces the number of metastatic tumors or cancer in the brain or reduces growth or size of a metastatic tumor or cancer in the brain as compared with an untreated subject diagnosed with a primary tumor or cancer or a subject diagnosed with a primary tumor or cancer and treated with a control.

15. The method of claim 14, wherein said method elicits protection against a metastasis of a breast tumor or cancer, a gastric tumor or cancer, an ovarian tumor or cancer, a melanoma, or a Her-2/neu-expressing tumor or cancer to the brain.

16. The method of claim 14, wherein said method elicits protection against a metastasis of a melanoma to the brain.

17. A method for reducing the incidence of a metastasis of a tumor or cancer to the brain of a subject diagnosed with a primary tumor or cancer, the method comprising the step of administering to said subject a recombinant *Listeria* strain expressing an immunogenic fragment of an angiogenic factor, wherein said angiogenic factor is associated with a vasculature of said tumor or cancer in said subject, wherein said angiogenic factor is a high molecular weight melanoma associated antigen (HMW-MAA)-C, wherein said immunogenic fragment is fused to an additional polypeptide, wherein said additional polypeptide is selected from the group consisting of an N-terminal ActA and a PEST amino acid sequence, wherein said subject mounts an immune response against said angiogenic factor or against said vasculature, wherein said metastatic tumor or cancer in the brain comprises a metastatic tumor or cancer of a melanoma, wherein said reducing the incidence of a metastasis reduces the number of metastatic tumors or cancer in the brain or reduces growth or size of a metastatic tumor or cancer in the brain as compared with an untreated subject diagnosed with a primary tumor or cancer or a subject diagnosed with a primary tumor or cancer and treated with a control.

18. The method of claim 17, wherein said method elicits protection against a metastasis of a melanoma to the brain.

19. The method of claim 17, wherein said subject mounts an immune response against said immunogenic fragment or against said tumor-associated vasculature.

20. The method of claim 19, wherein said immune response comprises a therapeutic immune response useful in treating, inhibiting, or suppressing said tumor in said subject.

* * * * *

SEQUENCE LISTING

<160> NUMBER OF SEQ ID NOS: 56

<210> SEQ ID NO 1
<211> LENGTH: 9
<212> TYPE: PRT
<213> ORGANISM: Artificial Sequence
<220> FEATURE:
<223> OTHER INFORMATION: pFlk-I1 epitope

<400> SEQUENCE: 1

Pro Gly Gly Pro Leu Met Val Ile Val
1               5

<210> SEQ ID NO 2
<211> LENGTH: 10
<212> TYPE: PRT
<213> ORGANISM: Artificial Sequence
<220> FEATURE:
<223> OTHER INFORMATION: pIC1 Her-2/neu epitope

<400> SEQUENCE: 2

Gly Ser Gly Ala Phe Gly Thr Val Tyr Lys
1               5                   10

<210> SEQ ID NO 3
<211> LENGTH: 9
<212> TYPE: PRT
<213> ORGANISM: Artificial Sequence
<220> FEATURE:
<223> OTHER INFORMATION: shared epitope between the Her-2/neu and Flk-1
      kinase domains

<400> SEQUENCE: 3

Gly Arg Gly Ala Phe Gly Gln Val Ile
1               5

<210> SEQ ID NO 4
<211> LENGTH: 1345
<212> TYPE: PRT
<213> ORGANISM: Mus musculus

<400> SEQUENCE: 4

Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
                20                  25                  30

Lys Leu Ser Thr Gln Lys Asp Ile Leu Thr Ile Leu Ala Asn Thr Thr
            35                  40                  45

Leu Gln Ile Thr Cys Arg Gly Gln Arg Asp Leu Asp Trp Leu Trp Pro
        50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
                100                 105                 110

Ala Ser Thr Val Tyr Val Tyr Val Arg Asp Tyr Arg Ser Pro Phe Ile
            115                 120                 125

Ala Ser Val Ser Asp Gln His Gly Ile Val Tyr Ile Thr Glu Asn Lys
        130                 135                 140

Asn Lys Thr Val Val Ile Pro Cys Arg Gly Ser Ile Ser Asn Leu Asn
145                 150                 155                 160

-continued

Val Ser Leu Cys Ala Arg Tyr Pro Glu Lys Arg Phe Val Pro Asp Gly
            165                 170                 175

Asn Arg Ile Ser Trp Asp Ser Glu Ile Gly Phe Thr Leu Pro Ser Tyr
        180                 185                 190

Met Ile Ser Tyr Ala Gly Met Val Phe Cys Glu Ala Lys Ile Asn Asp
    195                 200                 205

Glu Thr Tyr Gln Ser Ile Met Tyr Ile Val Val Val Gly Tyr Arg
210                 215                 220

Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
            260                 265                 270

Lys Ile Val Asn Arg Asp Val Lys Pro Phe Pro Gly Thr Val Ala Lys
        275                 280                 285

Met Phe Leu Ser Thr Leu Thr Ile Glu Ser Val Thr Lys Ser Asp Gln
    290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Gly Met Lys Ser Leu Val Glu Ala Thr Val Gly Ser Gln Val Arg Ile
            340                 345                 350

Pro Val Lys Tyr Leu Ser Tyr Pro Ala Pro Asp Ile Lys Trp Tyr Arg
        355                 360                 365

Asn Gly Arg Pro Ile Glu Ser Asn Tyr Thr Met Ile Val Gly Asp Glu
    370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
            420                 425                 430

Pro Met Asp Ser Tyr Gln Tyr Gly Thr Met Gln Thr Leu Thr Cys Thr
        435                 440                 445

Val Tyr Ala Asn Pro Pro Leu His His Ile Gln Trp Tyr Trp Gln Leu
    450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
                485                 490                 495

Val Thr Lys Asn Gln Tyr Ala Leu Ile Glu Gly Lys Asn Lys Thr Val
            500                 505                 510

Ser Thr Leu Val Ile Gln Ala Ala Asn Val Ser Ala Leu Tyr Lys Cys
        515                 520                 525

Glu Ala Ile Asn Lys Ala Gly Arg Gly Glu Arg Val Ile Ser Phe His
    530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

-continued

```
Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655

Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
        675                 680                 685

Ser Gly Asn Pro Thr Pro His Ile Thr Trp Phe Lys Asp Asn Glu Thr
690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
                725                 730                 735

Ala Cys Asn Val Leu Gly Cys Ala Arg Ala Glu Thr Leu Phe Ile Ile
            740                 745                 750

Glu Gly Ala Gln Glu Lys Thr Asn Leu Glu Val Ile Ile Leu Val Gly
        755                 760                 765

Thr Ala Val Ile Ala Met Phe Phe Trp Leu Leu Leu Val Ile Val Leu
770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
                805                 810                 815

Arg Leu Pro Tyr Asp Ala Ser Lys Trp Glu Phe Pro Arg Asp Arg Leu
            820                 825                 830

Lys Leu Gly Lys Pro Leu Gly Arg Gly Ala Phe Gly Gln Val Ile Glu
        835                 840                 845

Ala Asp Ala Phe Gly Ile Asp Lys Thr Ala Thr Cys Lys Thr Val Ala
850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
                885                 890                 895

Val Asn Leu Leu Gly Ala Cys Thr Lys Pro Gly Gly Pro Leu Met Val
            900                 905                 910

Ile Val Glu Phe Cys Lys Phe Gly Asn Leu Ser Thr Tyr Leu Arg Gly
        915                 920                 925

Lys Arg Asn Glu Phe Val Pro Tyr Lys Ser Lys Gly Ala Arg Phe Arg
930                 935                 940

Gln Gly Lys Asp Tyr Val Gly Glu Leu Ser Val Asp Leu Lys Arg Arg
945                 950                 955                 960

Leu Asp Ser Ile Thr Ser Ser Gln Ser Ser Ala Ser Ser Gly Phe Val
                965                 970                 975

Glu Glu Lys Ser Leu Ser Asp Val Glu Glu Glu Glu Ala Ser Glu Glu
            980                 985                 990

Leu Tyr Lys Asp Phe Leu Thr Leu  Glu His Leu Ile Cys  Tyr Ser Phe
```

Gln Val Ala Lys Gly Met Glu Phe Leu Ala Ser Arg Lys Cys Ile
          1010                1015                1020

His Arg Asp Leu Ala Ala Arg Asn Ile Leu Leu Ser Glu Lys Asn
          1025                1030                1035

Val Val Lys Ile Cys Asp Phe Gly Leu Ala Arg Asp Ile Tyr Lys
          1040                1045                1050

Asp Pro Asp Tyr Val Arg Lys Gly Asp Ala Arg Leu Pro Leu Lys
          1055                1060                1065

Trp Met Ala Pro Glu Thr Ile Phe Asp Arg Val Tyr Thr Ile Gln
          1070                1075                1080

Ser Asp Val Trp Ser Phe Gly Val Leu Leu Trp Glu Ile Phe Ser
          1085                1090                1095

Leu Gly Ala Ser Pro Tyr Pro Gly Val Lys Ile Asp Glu Glu Phe
          1100                1105                1110

Cys Arg Arg Leu Lys Glu Gly Thr Arg Met Arg Ala Pro Asp Tyr
          1115                1120                1125

Thr Thr Pro Glu Met Tyr Gln Thr Met Leu Asp Cys Trp His Glu
          1130                1135                1140

Asp Pro Asn Gln Arg Pro Ser Phe Ser Glu Leu Val Glu His Leu
          1145                1150                1155

Gly Asn Leu Leu Gln Ala Asn Ala Gln Gln Asp Gly Lys Asp Tyr
          1160                1165                1170

Ile Val Leu Pro Met Ser Glu Thr Leu Ser Met Glu Glu Asp Ser
          1175                1180                1185

Gly Leu Ser Leu Pro Thr Ser Pro Val Ser Cys Met Glu Glu Glu
          1190                1195                1200

Glu Val Cys Asp Pro Lys Phe His Tyr Asp Asn Thr Ala Gly Ile
          1205                1210                1215

Ser His Tyr Leu Gln Asn Ser Lys Arg Lys Ser Arg Pro Val Ser
          1220                1225                1230

Val Lys Thr Phe Glu Asp Ile Pro Leu Glu Glu Pro Glu Val Lys
          1235                1240                1245

Val Ile Pro Asp Asp Ser Gln Thr Asp Ser Gly Met Val Leu Ala
          1250                1255                1260

Ser Glu Glu Leu Lys Thr Leu Glu Asp Arg Asn Lys Leu Ser Pro
          1265                1270                1275

Ser Phe Gly Gly Met Met Pro Ser Lys Ser Arg Glu Ser Val Ala
          1280                1285                1290

Ser Glu Gly Ser Asn Gln Thr Ser Gly Tyr Gln Ser Gly Tyr His
          1295                1300                1305

Ser Asp Asp Thr Asp Thr Thr Val Tyr Ser Ser Asp Glu Ala Gly
          1310                1315                1320

Leu Leu Lys Met Val Asp Ala Ala Val His Ala Asp Ser Gly Thr
          1325                1330                1335

Thr Leu Arg Ser Pro Pro Val
          1340                1345

<210> SEQ ID NO 5
<211> LENGTH: 210
<212> TYPE: PRT
<213> ORGANISM: Artificial Sequence
<220> FEATURE:
<223> OTHER INFORMATION: VEGFR2 protein fragment

<400> SEQUENCE: 5

```
Arg Asp Ser Glu Glu Arg Val Leu Val Thr Glu Cys Gly Gly Gly Asp
1               5                   10                  15
Ser Ile Phe Cys Lys Thr Leu Thr Ile Pro Arg Val Val Gly Asn Asp
            20                  25                  30
Thr Gly Ala Tyr Lys Cys Ser Tyr Arg Asp Val Asp Ile Ala Ser Thr
        35                  40                  45
Val Tyr Val Tyr Val Arg Asp Tyr Arg Ser Pro Phe Ile Ala Ser Val
    50                  55                  60
Ser Asp Gln His Gly Ile Val Tyr Ile Thr Glu Asn Lys Asn Lys Thr
65                  70                  75                  80
Val Val Ile Pro Cys Arg Gly Ser Ile Ser Asn Leu Asn Val Ser Leu
                85                  90                  95
Cys Ala Arg Tyr Pro Glu Lys Arg Phe Val Pro Asp Gly Asn Arg Ile
            100                 105                 110
Ser Trp Asp Ser Glu Ile Gly Phe Thr Leu Pro Ser Tyr Met Ile Ser
        115                 120                 125
Tyr Ala Gly Met Val Phe Cys Glu Ala Lys Ile Asn Asp Glu Thr Tyr
    130                 135                 140
Gln Ser Ile Met Tyr Ile Val Val Val Gly Tyr Arg Ile Tyr Asp
145                 150                 155                 160
Val Ile Leu Ser Pro Pro His Glu Ile Glu Leu Ser Ala Gly Glu Lys
                165                 170                 175
Leu Val Leu Asn Cys Thr Ala Arg Thr Glu Leu Asn Val Gly Leu Asp
            180                 185                 190
Phe Thr Trp His Ser Pro Ser Lys Ser His His Lys Lys Ile Val
        195                 200                 205
Asn Arg
    210
```

<210> SEQ ID NO 6
<211> LENGTH: 186
<212> TYPE: PRT
<213> ORGANISM: Artificial Sequence
<220> FEATURE:
<223> OTHER INFORMATION: VEGFR2 protein fragment

<400> SEQUENCE: 6

```
Val Ile Arg Gly Pro Glu Ile Thr Val Gln Pro Ala Ala Gln Pro Thr
1               5                   10                  15
Glu Gln Glu Ser Val Ser Leu Leu Cys Thr Ala Asp Arg Asn Thr Phe
            20                  25                  30
Glu Asn Leu Thr Trp Tyr Lys Leu Gly Ser Gln Ala Thr Ser Val His
        35                  40                  45
Met Gly Glu Ser Leu Thr Pro Val Cys Lys Asn Leu Asp Ala Leu Trp
    50                  55                  60
Lys Leu Asn Gly Thr Met Phe Ser Asn Ser Thr Asn Asp Ile Leu Ile
65                  70                  75                  80
Val Ala Phe Gln Asn Ala Ser Leu Gln Asp Gln Gly Asp Tyr Val Cys
                85                  90                  95
Ser Ala Gln Asp Lys Lys Thr Lys Lys Arg His Cys Leu Val Lys Gln
            100                 105                 110
Leu Ile Ile Leu Glu Arg Met Ala Pro Met Ile Thr Gly Asn Leu Glu
        115                 120                 125
Asn Gln Thr Thr Thr Ile Gly Glu Thr Ile Glu Val Thr Cys Pro Ala
```

```
                     130               135                 140
Ser Gly Asn Pro Thr Pro His Ile Thr Trp Phe Lys Asp Asn Glu Thr
145                 150                 155                 160

Leu Val Glu Asp Ser Gly Ile Val Leu Arg Asp Gly Asn Arg Asn Leu
                165                 170                 175

Thr Ile Arg Arg Val Arg Lys Glu Asp Gly
            180                 185

<210> SEQ ID NO 7
<211> LENGTH: 290
<212> TYPE: PRT
<213> ORGANISM: Artificial Sequence
<220> FEATURE:
<223> OTHER INFORMATION: VEGFR2 protein fragment

<400> SEQUENCE: 7

Glu Gly Glu Leu Lys Thr Gly Tyr Leu Ser Ile Val Met Asp Pro Asp
1               5                   10                  15

Glu Leu Pro Leu Asp Glu Arg Cys Glu Arg Leu Pro Tyr Asp Ala Ser
                20                  25                  30

Lys Trp Glu Phe Pro Arg Asp Arg Leu Lys Leu Gly Lys Pro Leu Gly
            35                  40                  45

Arg Gly Ala Phe Gly Gln Val Ile Glu Ala Asp Ala Phe Gly Ile Asp
        50                  55                  60

Lys Thr Ala Thr Cys Lys Thr Val Ala Val Lys Met Leu Lys Glu Gly
65                  70                  75                  80

Ala Thr His Ser Glu His Arg Ala Leu Met Ser Glu Leu Lys Ile Leu
                85                  90                  95

Ile His Ile Gly His His Leu Asn Val Val Asn Leu Leu Gly Ala Cys
            100                 105                 110

Thr Lys Pro Gly Gly Pro Leu Met Val Ile Val Glu Phe Cys Lys Phe
        115                 120                 125

Gly Asn Leu Ser Thr Tyr Leu Arg Gly Lys Arg Asn Glu Phe Val Pro
    130                 135                 140

Tyr Lys Ser Lys Gly Ala Arg Phe Arg Gln Gly Lys Asp Tyr Val Gly
145                 150                 155                 160

Glu Leu Ser Val Asp Leu Lys Arg Arg Leu Asp Ser Ile Thr Ser Ser
                165                 170                 175

Gln Ser Ser Ala Ser Ser Gly Phe Val Glu Lys Ser Leu Ser Asp
            180                 185                 190

Val Glu Glu Glu Glu Ala Ser Glu Glu Leu Tyr Lys Asp Phe Leu Thr
        195                 200                 205

Leu Glu His Leu Ile Cys Tyr Ser Phe Gln Val Ala Lys Gly Met Glu
    210                 215                 220

Phe Leu Ala Ser Arg Lys Cys Ile His Arg Asp Leu Ala Ala Arg Asn
225                 230                 235                 240

Ile Leu Leu Ser Glu Lys Asn Val Val Lys Ile Cys Asp Phe Gly Leu
                245                 250                 255

Ala Arg Asp Ile Tyr Lys Asp Pro Asp Tyr Val Arg Lys Gly Asp Ala
            260                 265                 270

Arg Leu Pro Leu Lys Trp Met Ala Pro Glu Thr Ile Phe Asp Arg Val
        275                 280                 285

Tyr Thr
    290
```

```
<210> SEQ ID NO 8
<211> LENGTH: 529
<212> TYPE: PRT
<213> ORGANISM: Listeria monocytogenes

<400> SEQUENCE: 8

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380
```

```
Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
            435                 440                 445

Gln His Lys Asn Trp Ser Glu Asn Asn Lys Ser Lys Leu Ala His Phe
            450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
            485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
            515                 520                 525

Glu

<210> SEQ ID NO 9
<211> LENGTH: 441
<212> TYPE: PRT
<213> ORGANISM: Listeria monocytogenes

<400> SEQUENCE: 9

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
            35                  40                  45

Pro Lys Thr Pro Ile Glu Lys Lys His Ala Asp Glu Ile Asp Lys Tyr
50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
            85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
            165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
            210                 215                 220
```

```
Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
            245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
        290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
        420                 425                 430

Ile Ser Trp Asp Glu Val Asn Tyr Asp
            435                 440

<210> SEQ ID NO 10
<211> LENGTH: 416
<212> TYPE: PRT
<213> ORGANISM: Listeria monocytogenes

<400> SEQUENCE: 10

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160
```

Met Thr Asn Gln Asp Asn Lys Ile Val Val Lys Asn Ala Thr Lys Ser
            165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
            210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
            245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
            290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
            370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

<210> SEQ ID NO 11
<211> LENGTH: 390
<212> TYPE: PRT
<213> ORGANISM: Listeria monocytogenes

<400> SEQUENCE: 11

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
            35                  40                  45

Val Asn Thr Gly Pro Arg Tyr Glu Thr Ala Arg Glu Val Ser Ser Arg
        50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His

|     |     |     | 115 |     |     |     | 120 |     |     |     | 125 |     |     |
| --- | --- | --- | --- | --- | --- | --- | --- | --- | --- | --- | --- | --- | --- |

Pro Gly Leu Pro Ser Asp Ser Ala Ala Glu Ile Lys Lys Arg Arg Lys
130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
                180                 185                 190

Ser Ser Pro Gln Pro Leu Lys Ala Asn Gln Gln Pro Phe Phe Pro Lys
                195                 200                 205

Val Phe Lys Lys Ile Lys Asp Ala Gly Lys Trp Val Arg Asp Lys Ile
210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
                260                 265                 270

Pro Glu Thr Pro Met Leu Leu Gly Phe Asn Ala Pro Ala Thr Ser Glu
                275                 280                 285

Pro Ser Ser Phe Glu Phe Pro Pro Pro Thr Asp Glu Glu Leu Arg
290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
                340                 345                 350

Thr Arg Gly Asp Leu Ala Ser Leu Arg Asn Ala Ile Asn Arg His Ser
                355                 360                 365

Gln Asn Phe Ser Asp Phe Pro Pro Ile Pro Thr Glu Glu Leu Asn
370                 375                 380

Gly Arg Gly Gly Arg Pro
385                 390

<210> SEQ ID NO 12
<211> LENGTH: 1170
<212> TYPE: DNA
<213> ORGANISM: Listeria monocytogenes

<400> SEQUENCE: 12

| | | |
|---|---|---|
| atgcgtgcga tgatggtggt tttcattact gccaattgca ttacgattaa ccccgacata | 60 |
| atatttgcag cgacagatag cgaagattct agtctaaaca cagatgaatg ggaagaagaa | 120 |
| aaaacagaag agcaaccaag cgaggtaaat acgggaccaa gatacgaaac tgcacgtgaa | 180 |
| gtaagttcac gtgatattaa agaactagaa aaatcgaata agtgagaaa tacgaacaaa | 240 |
| gcagacctaa tagcaatgtt gaaagaaaaa gcagaaaaag gtccaaatat caataataac | 300 |
| aacagtgaac aaaactgagaa tgcggctata atgaagagg cttcaggagc cgaccgacca | 360 |
| gctatacaag tggagcgtcg tcatccagga ttgccatcgg atagcgcagc ggaaattaaa | 420 |
| aaaagaagga agccatagc atcatcggat agtgagcttg aaagccttac ttatccggat | 480 |
| aaaccaacaa agtaaataa gaaaaagtg gcgaaagagt cagttgcgga tgcttctgaa | 540 |

```
agtgacttag attctagcat gcagtcagca gatgagtctt caccacaacc tttaaaagca      600
aaccaacaac catttttccc taaagtattt aaaaaaataa agatgcggg gaaatgggta       660 cgtgataaaa tcgacgaaaa tcctgaagta aagaaagcga ttgttgataa aagtgcaggg     720
ttaattgacc aattattaac caaaaagaaa agtgaagagg taaatgcttc ggacttcccg     780
ccaccaccta cggatgaaga gttaagactt gctttgccag agacaccaat gcttcttggt   840
tttaatgctc ctgctacatc agaaccgagc tcattcgaat tccaccacc acctacggat     900 gaagagttaa gacttgcttt gccagagacg ccaatgcttc ttggttttaa tgctcctgct     960
acatcggaac cgagctcgtt cgaatttcca ccgcctccaa cagaagatga actagaaatc    1020
atccgggaaa cagcatcctc gctagattct agttttacaa gaggggattt agctagtttg     1080
agaaatgcta ttaatcgcca tagtcaaaat ttctctgatt tcccaccaat cccaacagaa    1140
gaagagttga acgggagagg cggtagacca                                      1170
```

<210> SEQ ID NO 13
<211> LENGTH: 32
<212> TYPE: PRT
<213> ORGANISM: Listeria monocytogenes

<400> SEQUENCE: 13

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 14
<211> LENGTH: 19
<212> TYPE: PRT
<213> ORGANISM: Listeria monocytogenes

<400> SEQUENCE: 14

Lys Glu Asn Ser Ile Ser Ser Met Ala Pro Pro Ala Ser Pro Pro Ala
1               5                   10                  15

Ser Pro Lys

<210> SEQ ID NO 15
<211> LENGTH: 14
<212> TYPE: PRT
<213> ORGANISM: Listeria monocytogenes

<400> SEQUENCE: 15

Lys Thr Glu Glu Gln Pro Ser Glu Val Asn Thr Gly Pro Arg
1               5                   10

<210> SEQ ID NO 16
<211> LENGTH: 28
<212> TYPE: PRT
<213> ORGANISM: Listeria monocytogenes

<400> SEQUENCE: 16

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 17
<211> LENGTH: 20
<212> TYPE: PRT
<213> ORGANISM: Listeria monocytogenes

```
<400> SEQUENCE: 17

Lys Asn Glu Glu Val Asn Ala Ser Asp Phe Pro Pro Pro Thr Asp
1               5                  10                  15

Glu Glu Leu Arg
            20

<210> SEQ ID NO 18
<211> LENGTH: 33
<212> TYPE: PRT
<213> ORGANISM: Listeria monocytogenes

<400> SEQUENCE: 18

Arg Gly Gly Ile Pro Thr Ser Glu Glu Phe Ser Ser Leu Asn Ser Gly
1               5                  10                  15

Asp Phe Thr Asp Asp Glu Asn Ser Glu Thr Thr Glu Glu Glu Ile Asp
            20                  25                  30

Arg

<210> SEQ ID NO 19
<211> LENGTH: 28
<212> TYPE: PRT
<213> ORGANISM: Listeria monocytogenes

<400> SEQUENCE: 19

Lys Glu Ser Val Val Asp Ala Ser Glu Ser Asp Leu Asp Ser Ser Met
1               5                  10                  15

Gln Ser Ala Asp Glu Ser Thr Pro Gln Pro Leu Lys
            20                  25

<210> SEQ ID NO 20
<211> LENGTH: 20
<212> TYPE: PRT
<213> ORGANISM: Listeria monocytogenes

<400> SEQUENCE: 20

Lys Ser Glu Glu Val Asn Ala Ser Asp Phe Pro Pro Pro Thr Asp
1               5                  10                  15

Glu Glu Leu Arg
            20

<210> SEQ ID NO 21
<211> LENGTH: 33
<212> TYPE: PRT
<213> ORGANISM: Listeria monocytogenes

<400> SEQUENCE: 21

Arg Gly Gly Arg Pro Thr Ser Glu Glu Phe Ser Ser Leu Asn Ser Gly
1               5                  10                  15

Asp Phe Thr Asp Asp Glu Asn Ser Glu Thr Thr Glu Glu Glu Ile Asp
            20                  25                  30

Arg

<210> SEQ ID NO 22
<211> LENGTH: 19
<212> TYPE: PRT
<213> ORGANISM: Listeria monocytogenes

<400> SEQUENCE: 22

Arg Ser Glu Val Thr Ile Ser Pro Ala Glu Thr Pro Glu Ser Pro Pro
1               5                  10                  15
```

Ala Thr Pro

<210> SEQ ID NO 23
<211> LENGTH: 17
<212> TYPE: PRT
<213> ORGANISM: Streptococcus pyogenes

<400> SEQUENCE: 23

Lys Gln Asn Thr Ala Ser Thr Glu Thr Thr Thr Thr Asn Glu Gln Pro
1               5                   10                  15

Lys

<210> SEQ ID NO 24
<211> LENGTH: 17
<212> TYPE: PRT
<213> ORGANISM: Streptococcus equisimilis

<400> SEQUENCE: 24

Lys Gln Asn Thr Ala Asn Thr Glu Thr Thr Thr Thr Asn Glu Gln Pro
1               5                   10                  15

Lys

<210> SEQ ID NO 25
<211> LENGTH: 10
<212> TYPE: PRT
<213> ORGANISM: Artificial Sequence
<220> FEATURE:
<223> OTHER INFORMATION: Her-2/neu EC1

<400> SEQUENCE: 25

Ala Ser Pro Glu Thr His Leu Asp Met Leu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: her-2/neu EC2

<400> SEQUENCE: 26

Pro Asp Ser Leu Arg Asp Leu Ser Val Phe
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Flk-E1

<400> SEQUENCE: 27

Thr Tyr Gln Ser Ile Met Tyr Ile Val
1               5

<210> SEQ ID NO 28
<211> LENGTH: 9
<212> TYPE: PRT
<213> ORGANISM: Artificial Sequence
<220> FEATURE:
<223> OTHER INFORMATION: Flk-E2

<400> SEQUENCE: 28

Met Phe Ser Asn Ser Thr Asn Asp Ile

<210> SEQ ID NO 29
<211> LENGTH: 9
<212> TYPE: PRT
<213> ORGANISM: Artificial Sequence
<220> FEATURE:
<223> OTHER INFORMATION: Her2-pEC1 302-310

<400> SEQUENCE: 29

Pro Tyr Asn Tyr Leu Ser Thr Glu Val
1               5

<210> SEQ ID NO 30
<211> LENGTH: 9
<212> TYPE: PRT
<213> ORGANISM: Artificial Sequence
<220> FEATURE:
<223> OTHER INFORMATION: HIV-pGag

<400> SEQUENCE: 30

Ala Met Gln Met Leu Lys Glu Thr Ile
1               5

<210> SEQ ID NO 31
<211> LENGTH: 32
<212> TYPE: DNA
<213> ORGANISM: Artificial Sequence
<220> FEATURE:
<223> OTHER INFORMATION: Flk-E1 primer (F)

<400> SEQUENCE: 31
gggctcgagc gtgattctga ggaaagggta tt                          32

<210> SEQ ID NO 32
<211> LENGTH: 33
<212> TYPE: DNA
<213> ORGANISM: Artificial Sequence
<220> FEATURE:
<223> OTHER INFORMATION: Flk-E1 (R)

<400> SEQUENCE: 32
gggactagtt tacccggttt acaatcttct tat                         33

<210> SEQ ID NO 33
<211> LENGTH: 31
<212> TYPE: DNA
<213> ORGANISM: Artificial Sequence
<220> FEATURE:
<223> OTHER INFORMATION: Flk-E2 (F)

<400> SEQUENCE: 33
gggctcgagg tgatcagggg tcctgaaatt a                           31

<210> SEQ ID NO 34
<211> LENGTH: 30
<212> TYPE: DNA
<213> ORGANISM: Artificial Sequence
<220> FEATURE:
<223> OTHER INFORMATION: Flk-E2 (R)

<400> SEQUENCE: 34
gggactagtt tagcctccat cctccttcct                             30

<210> SEQ ID NO 35
<211> LENGTH: 30

```
<210> SEQ ID NO 35
<211> LENGTH: 30
<212> TYPE: DNA
<213> ORGANISM: Artificial Sequence
<220> FEATURE:
<223> OTHER INFORMATION: Flk-I1 (F)

<400> SEQUENCE: 35
gggctcgagg aagggggaact gaagacagcc                                      30

<210> SEQ ID NO 36
<211> LENGTH: 39
<212> TYPE: DNA
<213> ORGANISM: Artificial Sequence
<220> FEATURE:
<223> OTHER INFORMATION: Flk-I1 (R)

<400> SEQUENCE: 36
gggactagtt tatgtgtata ctctgtcaaa aatggtttc                             39

<210> SEQ ID NO 37
<211> LENGTH: 18
<212> TYPE: PRT
<213> ORGANISM: Artificial Sequence
<220> FEATURE:
<223> OTHER INFORMATION: EC1FP  FP =reverse primer RP= reverse primer

<400> SEQUENCE: 37

Ala Gly Gly Gly Cys Thr Gly Thr Cys Ala Gly Gly Thr Ala Gly Thr
 1               5                  10                  15

Gly Cys

<210> SEQ ID NO 38
<211> LENGTH: 18
<212> TYPE: PRT
<213> ORGANISM: Artificial Sequence
<220> FEATURE:
<223> OTHER INFORMATION: EC1RP

<400> SEQUENCE: 38

Thr Gly Ala Cys Cys Thr Cys Thr Thr Gly Gly Thr Thr Ala Thr Thr
 1               5                  10                  15

Cys Gly

<210> SEQ ID NO 39
<211> LENGTH: 18
<212> TYPE: PRT
<213> ORGANISM: Artificial Sequence
<220> FEATURE:
<223> OTHER INFORMATION: EC2FP

<400> SEQUENCE: 39

Ala Cys Cys Thr Gly Cys Cys Cys Thr Cys Ala Ala Cys Thr
 1               5                  10                  15

Ala Cys

<210> SEQ ID NO 40
<211> LENGTH: 18
<212> TYPE: PRT
<213> ORGANISM: Artificial Sequence
<220> FEATURE:
<223> OTHER INFORMATION: EC3 FP

<400> SEQUENCE: 40

Gly Ala Cys Gly Cys Cys Cys Thr Cys Thr Ala Cys Ala Gly Thr Thr
 1               5                  10                  15
```

Gly Cys

<210> SEQ ID NO 41
<211> LENGTH: 18
<212> TYPE: PRT
<213> ORGANISM: Artificial Sequence
<220> FEATURE:
<223> OTHER INFORMATION: EC2 RP

<400> SEQUENCE: 41

Gly Thr Gly Gly Ala Thr Thr Gly Gly Cys Thr Cys Thr Gly Ala Thr
1               5                   10                  15

Thr Cys

<210> SEQ ID NO 42
<211> LENGTH: 18
<212> TYPE: PRT
<213> ORGANISM: Artificial Sequence
<220> FEATURE:
<223> OTHER INFORMATION: EC3RP

<400> SEQUENCE: 42

Thr Gly Ala Gly Thr Thr Ala Cys Ala Gly Ala Cys Cys Ala Ala Gly
1               5                   10                  15

Cys Cys

<210> SEQ ID NO 43
<211> LENGTH: 19
<212> TYPE: PRT
<213> ORGANISM: Artificial Sequence
<220> FEATURE:
<223> OTHER INFORMATION: IC1FP

<400> SEQUENCE: 43

Cys Ala Ala Ala Cys Gly Ala Ala Gly Gly Ala Gly Ala Cys Ala Gly
1               5                   10                  15

Ala Ala Gly

<210> SEQ ID NO 44
<211> LENGTH: 18
<212> TYPE: PRT
<213> ORGANISM: Artificial Sequence
<220> FEATURE:
<223> OTHER INFORMATION: IC1 RP

<400> SEQUENCE: 44

Cys Ala Cys Cys Ala Thr Cys Ala Ala Ala Cys Ala Cys Ala Thr Cys
1               5                   10                  15

Gly Gly

<210> SEQ ID NO 45
<211> LENGTH: 18
<212> TYPE: PRT
<213> ORGANISM: Artificial Sequence
<220> FEATURE:
<223> OTHER INFORMATION: IC2 FP

<400> SEQUENCE: 45

Cys Ala Cys Thr Gly Cys Thr Gly Gly Ala Ala Gly Ala Thr Gly Ala
1               5                   10                  15

Thr Gly

<210> SEQ ID NO 46

```
<211> LENGTH: 18
<212> TYPE: PRT
<213> ORGANISM: Artificial Sequence
<220> FEATURE:
<223> OTHER INFORMATION: IC2 RP

<400> SEQUENCE: 46

Thr Thr Thr Gly Thr Gly Gly Cys Gly Ala Thr Gly Gly Ala Gly Ala
1               5                   10                  15

Cys Cys

<210> SEQ ID NO 47
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 47

Ile Ile Leu Val Gly Thr Ala Val Ile
1               5

<210> SEQ ID NO 48
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 48

Leu Leu Val Ile Ile Leu Arg Thr Val
1               5

<210> SEQ ID NO 49
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 49

Ile Leu Leu Ser Glu Lys Asn Val Val
1               5

<210> SEQ ID NO 50
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 50

Thr Ile Phe Asp Arg Val Tyr Thr Ile
1               5

<210> SEQ ID NO 51
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 51

Val Leu Leu Trp Glu Ile Phe Ser Leu
1               5
```

```
<210> SEQ ID NO 52
<211> LENGTH: 9
<212> TYPE: PRT
<213> ORGANISM: Artificial Sequence
<220> FEATURE:
<223> OTHER INFORMATION: CD105A peptide

<400> SEQUENCE: 52

Ala Gly Pro Arg Thr Val Thr Val Met
1               5

<210> SEQ ID NO 53
<211> LENGTH: 9
<212> TYPE: PRT
<213> ORGANISM: Artificial Sequence
<220> FEATURE:
<223> OTHER INFORMATION: Cd105B peptide

<400> SEQUENCE: 53

Ala Tyr Ser Ser Cys Gly Met Lys Val
1               5

<210> SEQ ID NO 54
<211> LENGTH: 9
<212> TYPE: PRT
<213> ORGANISM: Artificial Sequence
<220> FEATURE:
<223> OTHER INFORMATION: AH1 peptide

<400> SEQUENCE: 54

Ser Pro Ser Tyr Val Tyr His Gln Phe
1               5

<210> SEQ ID NO 55
<211> LENGTH: 654
<212> TYPE: PRT
<213> ORGANISM: Mus musculus

<400> SEQUENCE: 55

Met Asp Arg Gly Val Leu Pro Leu Pro Ile Thr Leu Leu Leu Phe Glu
1               5                   10                  15

Ile Tyr Ser Phe Glu Pro Thr Thr Gly Leu Ala Glu Arg Val Gly Cys
            20                  25                  30

Asp Leu Gln Pro Val Asp Pro Thr Arg Gly Glu Val Thr Phe Thr Thr
        35                  40                  45

Ser Gln Val Ser Glu Gly Cys Val Ala Gln Ala Ala Asn Ala Val Arg
    50                  55                  60

Glu Val His Val Leu Phe Leu Asp Phe Pro Gly Met Leu Ser His Leu
65                  70                  75                  80

Glu Leu Thr Leu Gln Ala Ser Lys Gln Asn Gly Thr Glu Thr Arg Glu
                85                  90                  95

Val Phe Leu Val Leu Val Ser Asn Lys Asn Val Phe Val Lys Phe Gln
            100                 105                 110

Ala Pro Glu Ile Pro Leu His Leu Ala Tyr Asp Ser Ser Leu Val Ile
        115                 120                 125

Phe Gln Gly Gln Pro Arg Val Asn Ile Thr Val Leu Pro Ser Leu Thr
    130                 135                 140

Ser Arg Lys Gln Ile Leu Asp Trp Ala Ala Thr Lys Gly Ala Ile Thr
145                 150                 155                 160

Ser Ile Ala Ala Leu Asp Asp Pro Gln Ser Ile Val Leu Gln Leu Gly
                165                 170                 175
```

```
Gln Asp Pro Lys Ala Pro Phe Leu Cys Leu Pro Glu Ala His Lys Asp
            180                 185                 190

Met Gly Ala Thr Leu Glu Trp Gln Pro Arg Ala Gln Thr Pro Val Gln
            195                 200                 205

Ser Cys Arg Leu Glu Gly Val Ser Gly His Lys Glu Ala Tyr Ile Leu
            210                 215                 220

Arg Ile Leu Pro Gly Ser Glu Ala Gly Pro Arg Thr Val Thr Val Met
225                 230                 235                 240

Met Glu Leu Ser Cys Thr Ser Gly Asp Ala Ile Leu Ile Leu His Gly
            245                 250                 255

Pro Pro Tyr Val Ser Trp Phe Ile Asp Ile Asn His Ser Met Gln Ile
            260                 265                 270

Leu Thr Thr Gly Glu Tyr Ser Val Lys Ile Phe Pro Gly Ser Lys Val
            275                 280                 285

Lys Gly Val Glu Leu Pro Asp Thr Pro Gln Gly Leu Ile Ala Glu Ala
            290                 295                 300

Arg Lys Leu Asn Ala Ser Ile Val Thr Ser Phe Val Glu Leu Pro Leu
305                 310                 315                 320

Val Ser Asn Val Ser Leu Arg Ala Ser Ser Cys Gly Gly Val Phe Gln
            325                 330                 335

Thr Thr Pro Ala Pro Val Val Thr Thr Pro Pro Lys Asp Thr Cys Ser
            340                 345                 350

Pro Val Leu Leu Met Ser Leu Ile Gln Pro Lys Cys Gly Asn Gln Val
            355                 360                 365

Met Thr Leu Ala Leu Asn Lys Lys His Val Gln Thr Leu Gln Cys Thr
            370                 375                 380

Ile Thr Gly Leu Thr Phe Trp Asp Ser Ser Cys Gln Ala Glu Asp Thr
385                 390                 395                 400

Asp Asp His Leu Val Leu Ser Ser Ala Tyr Ser Ser Cys Gly Met Lys
            405                 410                 415

Val Thr Ala His Val Val Ser Asn Glu Val Ile Ser Phe Pro Ser
            420                 425                 430

Gly Ser Pro Pro Leu Arg Lys Lys Val Gln Cys Ile Asp Met Asp Ser
            435                 440                 445

Leu Ser Phe Gln Leu Gly Leu Tyr Leu Ser Pro His Phe Leu Gln Ala
            450                 455                 460

Ser Asn Thr Ile Glu Leu Gly Gln Gln Ala Phe Val Gln Val Ser Val
465                 470                 475                 480

Ser Pro Leu Thr Ser Glu Val Thr Val Gln Leu Asp Ser Cys His Leu
            485                 490                 495

Asp Leu Gly Pro Glu Gly Asp Met Val Glu Leu Ile Gln Ser Arg Thr
            500                 505                 510

Ala Lys Gly Ser Cys Val Thr Leu Leu Ser Pro Ser Pro Glu Gly Asp
            515                 520                 525

Pro Arg Phe Ser Phe Leu Leu Arg Val Tyr Met Val Pro Thr Pro Thr
            530                 535                 540

Ala Gly Thr Leu Ser Cys Asn Leu Ala Leu Arg Pro Ser Thr Leu Ser
545                 550                 555                 560

Gln Glu Val Tyr Lys Thr Val Ser Met Arg Leu Asn Val Val Ser Pro
            565                 570                 575

Asp Leu Ser Gly Lys Gly Leu Val Leu Pro Ser Val Leu Gly Ile Thr
            580                 585                 590

Phe Gly Ala Phe Leu Ile Gly Ala Leu Leu Thr Ala Ala Leu Trp Tyr
```

```
              595                 600                 605
Ile Tyr Ser His Thr Arg Gly Pro Ser Lys Arg Glu Pro Val Val Ala
            610                 615                 620

Val Ala Pro Ala Ser Ser Glu Ser Ser Thr Asn His Ser Ile
625                 630                 635                 640

Gly Ser Thr Gln Ser Thr Pro Cys Ser Thr Ser Met Ala
                    645                 650

<210> SEQ ID NO 56
<211> LENGTH: 653
<212> TYPE: PRT
<213> ORGANISM: Mus musculus

<400> SEQUENCE: 56

Met Asp Arg Gly Val Leu Pro Leu Pro Ile Thr Leu Leu Phe Val Ile
1               5                   10                  15

Tyr Ser Phe Val Pro Thr Thr Gly Leu Ala Glu Arg Val Gly Cys Asp
                20                  25                  30

Leu Gln Pro Val Asp Pro Thr Arg Gly Glu Val Thr Phe Thr Thr Ser
            35                  40                  45

Gln Val Ser Glu Gly Cys Val Ala Gln Ala Ala Asn Ala Val Arg Glu
        50                  55                  60

Val His Val Leu Phe Leu Asp Phe Pro Gly Met Leu Ser His Leu Glu
65                  70                  75                  80

Leu Thr Leu Gln Ala Ser Lys Gln Asn Gly Thr Glu Thr Arg Glu Val
                85                  90                  95

Phe Leu Val Leu Val Ser Asn Lys Asn Val Phe Val Lys Phe Gln Ala
                100                 105                 110

Pro Glu Ile Pro Leu His Leu Ala Tyr Asp Ser Ser Leu Val Ile Phe
            115                 120                 125

Gln Gly Gln Pro Arg Val Asn Ile Thr Val Leu Pro Ser Leu Thr Ser
        130                 135                 140

Arg Lys Gln Ile Leu Asp Trp Ala Ala Thr Lys Gly Ala Ile Thr Ser
145                 150                 155                 160

Ile Ala Ala Leu Asp Asp Pro Gln Ser Ile Val Leu Gln Leu Gly Gln
                165                 170                 175

Asp Pro Lys Ala Pro Phe Leu Cys Leu Pro Glu Ala His Lys Asp Met
            180                 185                 190

Gly Ala Thr Leu Glu Trp Gln Pro Arg Ala Gln Thr Pro Val Gln Ser
        195                 200                 205

Cys Arg Leu Glu Gly Val Ser Gly His Lys Glu Ala Tyr Ile Leu Arg
    210                 215                 220

Ile Leu Pro Gly Ser Glu Ala Gly Pro Arg Thr Val Thr Val Met Met
225                 230                 235                 240

Glu Leu Ser Cys Thr Ser Gly Asp Ala Ile Leu Ile Leu His Gly Pro
                245                 250                 255

Pro Tyr Val Ser Trp Phe Ile Asp Ile Asn His Ser Met Gln Ile Leu
            260                 265                 270

Thr Thr Gly Glu Tyr Ser Val Lys Ile Phe Pro Gly Ser Lys Val Lys
        275                 280                 285

Gly Val Glu Leu Pro Asp Thr Pro Gln Gly Leu Ile Ala Glu Ala Arg
    290                 295                 300

Gln Leu Asn Ala Ser Ile Val Thr Ser Phe Val Glu Leu Pro Leu Val
305                 310                 315                 320
```

```
Ser Asn Val Ser Leu Arg Ala Ser Ser Cys Gly Gly Val Phe Gln Thr
                325             330             335

Thr Pro Ala Pro Val Val Thr Thr Pro Pro Lys Asp Thr Cys Ser Pro
            340             345             350

Val Leu Leu Met Ser Leu Ile Gln Pro Lys Cys Gly Asn Gln Val Met
                355             360             365

Thr Leu Ala Leu Asn Lys Lys His Val Gln Thr Leu Gln Cys Thr Ile
        370             375             380

Thr Gly Leu Thr Phe Trp Asp Ser Ser Cys Gln Ala Glu Asp Thr Asp
385             390             395             400

Asp His Leu Val Leu Ser Ser Ala Tyr Ser Ser Cys Gly Met Lys Val
                405             410             415

Thr Ala His Val Val Ser Asn Glu Val Ile Ile Ser Phe Pro Ser Gly
                420             425             430

Ser Pro Pro Leu Arg Lys Lys Val Gln Cys Ile Asp Met Asp Ser Leu
            435             440             445

Ser Phe Gln Leu Gly Leu Tyr Leu Ser Pro His Phe Leu Gln Ala Ser
    450             455             460

Asn Thr Ile Glu Leu Gly Gln Gln Ala Phe Val Gln Val Ser Val Ser
465             470             475             480

Pro Leu Thr Ser Glu Val Thr Val Gln Leu Asp Ser Cys His Leu Asp
                485             490             495

Leu Gly Pro Glu Gly Asp Met Val Glu Leu Ile Gln Ser Arg Thr Ala
            500             505             510

Lys Gly Ser Cys Val Thr Leu Leu Ser Pro Ser Pro Glu Gly Asp Pro
            515             520             525

Arg Phe Ser Phe Leu Leu Arg Val Tyr Met Val Pro Thr Pro Thr Ala
    530             535             540

Gly Thr Leu Ser Cys Asn Leu Ala Leu Arg Pro Ser Thr Leu Ser Gln
545             550             555             560

Glu Val Tyr Lys Thr Val Ser Met Arg Leu Asn Val Val Ser Pro Asp
                565             570             575

Leu Ser Gly Lys Gly Leu Val Leu Pro Ser Val Leu Gly Ile Thr Phe
            580             585             590

Gly Ala Phe Leu Ile Gly Ala Leu Leu Thr Ala Ala Leu Trp Tyr Ile
        595             600             605

Tyr Ser His Thr Arg Gly Pro Ser Lys Arg Glu Pro Val Val Ala Val
        610             615             620

Ala Ala Pro Ala Ser Ser Glu Ser Ser Ser Thr Asn His Ser Ile Gly
625             630             635             640

Ser Thr Gln Ser Thr Pro Cys Ser Thr Ser Ser Met Ala
                645             650
```